United States Patent
Maier-Hein et al.

(10) Patent No.: US 12,329,491 B2
(45) Date of Patent: Jun. 17, 2025

(54) METHOD AND SYSTEM FOR AUGMENTED IMAGING IN OPEN TREATMENT USING MULTISPECTRAL INFORMATION

(71) Applicant: DEUTSCHES KREBSFORSCHUNGSZENTRUM STIFTUNG DES ÖFFENTLICHEN RECHTS, Heidelberg (DE)

(72) Inventors: Lena Maier-Hein, Heidelberg (DE); Sebastian Josef Wirkert, Heidelberg (DE); Anant Suraj Vemuri, Heidelberg (DE); Leonardo Antonio Ayala Menjivar, Heidelberg (DE); Silvia Seidlitz, Heidelberg (DE); Thomas Kirchner, Heidelberg (DE); Tim Adler, Heidelberg (DE)

(73) Assignee: DEUTSCHES KREBSFORSCHUNGSZENTRUM STIFTUNG DES ÖFFENTLICHEN RECHTS, Heidelberg (DE)

( * ) Notice: Subject to any disclaimer, the term of this patent is extended or adjusted under 35 U.S.C. 154(b) by 1024 days.

(21) Appl. No.: 17/263,850

(22) PCT Filed: Jul. 31, 2019

(86) PCT No.: PCT/EP2019/070649
§ 371 (c)(1),
(2) Date: Jan. 27, 2021

(87) PCT Pub. No.: WO2020/025684
PCT Pub. Date: Feb. 6, 2020

(65) Prior Publication Data
US 2022/0008157 A1    Jan. 13, 2022

(30) Foreign Application Priority Data
Jul. 31, 2018  (EP) .................................... 18186670

(51) Int. Cl.
*A61B 5/00* (2006.01)
*A61B 5/02* (2006.01)
(Continued)

(52) U.S. Cl.
CPC .......... *A61B 5/0037* (2013.01); *A61B 5/0002* (2013.01); *A61B 5/02042* (2013.01);
(Continued)

(58) Field of Classification Search
CPC ... A61B 5/0037; A61B 90/361; A61B 5/0002; A61B 5/02042; A61B 5/0205;
(Continued)

(56) References Cited

U.S. PATENT DOCUMENTS

| 7,620,242 B2 | 11/2009 | Enomoto et al. |
| 2002/0065468 A1* | 5/2002 | Utzinger ............ A61B 1/00186 356/327 |

(Continued)

FOREIGN PATENT DOCUMENTS

| EP | 3013045 A1 | 4/2016 |
| WO | WO-2014/203453 A1 | 12/2014 |

(Continued)

OTHER PUBLICATIONS

Schlegl et al., "Unsupervised Anomaly Detection with Generative Adversarial Networks to Guide Marker Discovery," Proceedings of IPMI, 12 pages (2017).

(Continued)

*Primary Examiner* — Sean A Frith
(74) *Attorney, Agent, or Firm* — MARSHALL, GERSTEIN & BORUN LLP

(57) ABSTRACT

Disclosed herein is a method of generating augmented images of tissue of a patient undergoing open treatment, in particular open surgery, wherein each augmented image associates at least one tissue parameter with a region or pixel (Continued)

of the image of the tissue, said method comprising the following steps: estimating a spectral composition of light illuminating a region of interest of the tissue, obtaining one or more multispectral images of the region of interest, applying a machine learning based regressor or classifier to the one or more multispectral images, or an image derived from said multispectral image, to thereby derive one or more tissue parameters associated with image regions or pixels of the corresponding multispectral image, wherein said regressor or classifier has been trained to predict the one or more tissue parameters from a multispectral image under a given spectral composition of illumination, wherein the regressor or classifier employed is made to match the estimated spectral composition of light illuminating said region of interest of the tissue.

24 Claims, 20 Drawing Sheets

(51) Int. Cl.

| | | |
|---|---|---|
| *A61B 5/0205* | (2006.01) | |
| *A61B 5/145* | (2006.01) | |
| *A61B 5/1455* | (2006.01) | |
| *A61B 90/00* | (2016.01) | |
| *G06F 18/2413* | (2023.01) | |
| *G06T 7/00* | (2017.01) | |
| *G06V 10/141* | (2022.01) | |
| *G06V 10/46* | (2022.01) | |
| *G06V 10/60* | (2022.01) | |
| *G06V 10/764* | (2022.01) | |
| *G16H 20/40* | (2018.01) | |
| *G16H 30/40* | (2018.01) | |
| *G16H 50/20* | (2018.01) | |
| *G16H 50/70* | (2018.01) | |

(52) U.S. Cl.
CPC ........ *A61B 5/0205* (2013.01); *A61B 5/14546* (2013.01); *A61B 5/14551* (2013.01); *A61B 5/443* (2013.01); *A61B 5/4547* (2013.01); *A61B 5/4875* (2013.01); *A61B 5/489* (2013.01); *A61B 5/4893* (2013.01); *A61B 5/7275* (2013.01); *A61B 5/749* (2013.01); *A61B 90/361* (2016.02); *G06F 18/2413* (2023.01); *G06T 7/0012* (2013.01); *G06V 10/141* (2022.01); *G06V 10/60* (2022.01); *G06V 10/764* (2022.01); *G16H 20/40* (2018.01); *G16H 30/40* (2018.01); *G16H 50/20* (2018.01); *G16H 50/70* (2018.01); *A61B 2090/365* (2016.02); *G06T 2207/20081* (2013.01); *G06V 10/467* (2022.01); *G06V 2201/031* (2022.01)

(58) Field of Classification Search
CPC . A61B 5/14546; A61B 5/14551; A61B 5/443; A61B 5/4547; A61B 5/4875; A61B 5/489; A61B 5/4893; A61B 5/7275; A61B 5/749; A61B 2090/365; G16H 20/40; G16H 50/70; G16H 50/20; G16H 30/40; G06V 10/141; G06V 10/60; G06V 10/764; G06V 10/467; G06V 2201/031; G06F 18/2413; G06T 7/0012; G06T 2207/20081
See application file for complete search history.

(56) References Cited

U.S. PATENT DOCUMENTS

| | | | |
|---|---|---|---|
| 2013/0080134 A1* | 3/2013 | Donovan | G16H 50/50 703/11 |
| 2014/0012135 A1* | 1/2014 | Freeman | A61B 5/445 600/407 |
| 2016/0078317 A1 | 3/2016 | Gu et al. | |
| 2017/0367580 A1* | 12/2017 | DiMaio | A61B 5/445 |

FOREIGN PATENT DOCUMENTS

| | | | |
|---|---|---|---|
| WO | WO-2017/008105 A1 | 1/2017 | |
| WO | WO-2017216585 A1 * | 12/2017 | ......... A61B 1/00009 |

OTHER PUBLICATIONS

International Search Report and Written Opinion from International Application No. PCT/EP2019/070649 dated Oct. 25, 2019.

* cited by examiner (a) Two simulated spectra  (b) Reshaped to mosaic  (c) Expanded to 3x3 and stained $x_i$ with $x_j$ (marked red)

METHOD AND SYSTEM FOR AUGMENTED IMAGING IN OPEN TREATMENT USING MULTISPECTRAL INFORMATION

CROSS-REFERENCE TO RELATED APPLICATIONS

This is a U.S. National Phase of International Application No. PCT/EP2019/070649, filed Jul. 31, 2019, which claims priority to European Application No. 18186670.8 filed Jul. 31, 2018.

FIELD OF THE INVENTION

The present invention is in the field of medical technology. In particular, the present invention relates to a method and system for augmented imaging of tissue using multispectral information.

BACKGROUND OF THE INVENTION

In open or minimally invasive surgery, there is a need for augmented imaging of the tissue under treatment. Augmented imaging as understood herein indicates providing an image of the tissue which indicates additional information other than the film image of the tissue itself. This additional information is generally referred to as "tissue parameter" in the present disclosure.

One important example of such additional information could be functional information, in which information related to the functional state of the tissue is provided. Particularly important functional states to be indicated to the surgeon is the perfusion or the oxygenation of the tissue. Functional images in a broader sense may also comprise images providing information about functional states derived from the functional parameters, for example a metabolic state, or other properties of the tissue derived from such functional parameters, such as cancerous tissue, in particular cancerous lymph node tissue, and in particular the discrimination between benign and malign tumor more tissue. The corresponding information is generally referred to as "tissue parameter" herein.

Oxygen saturation, here also referred to as oxygenation, denotes the fraction of oxygen saturated hemoglobin relative to the total hemoglobin. Since oxygen saturated hemoglobin and oxygen un-saturated hemoglobin have different light absorption properties depending on wavelength, oxygenation can in principle be determined by multispectral imaging.

Perfusion can be defined as the volume of blood that flows through the capillaries of a certain tissue or organ in an interval of time. The stopping or reduction in perfusion is known as "ischemia" and can lead to irreversible damage. Depending on the organ, this damage will occur within minutes to hours. The damage is caused by the imbalance between supply and demand, since cells still consume oxygen and other nutrients, but no new oxygenated blood is arriving. Because of reduced oxygenation and the lower amount of blood in ischemia, multispectral imaging has potential to characterize perfusion as well.

Ischemia can be prompted by several reasons. In some situations, it may be caused by a physician voluntarily. An example for this is partial nephrectomy, where a kidney tumor is surgically removed. To reduce bleeding during the resection, ischemia can be induced by clamping the supplying hilar vessel. In this case, it would be extremely helpful for the surgeon to resort to functional imaging to estimate the ischemia, both at the beginning of the intervention, to confirm that perfusion has been successfully stopped, as well as after the invention, to confirm that the kidney again receives sufficient blood flow.

Ischemia can also be an unwanted side effect after surgery. Two prominent examples are organ transplants and anastomosis, i.e. the reconnection of two tubular sections. In this case too, it would be extremely helpful for surgeons to judge the perfusion state during and after the intervention.

Visualizing perfusion may also be helpful in identifying tumors. Detectable changes related to perfusion can in some cases be attributed to cancer, because important hallmarks of cancer such as hypoxia (deprivation of oxygenated blood) and angiogenesis (formation of new blood vessels) are characterized by changes in oxygenation and blood volume fraction.

While it is in principle known that oxygenation can be detected using multispectral imaging, known methods suffer from severe drawbacks. One deficiency in existing methods is that they are not able to provide "live" augmented images, i.e. images created in real time at a rate of e.g. 25 Hz or above, such as to give immediate feedback to the surgeon and to avoid motion artefacts or blurring.

A further deficiency is the lack of precision in the functional information conveyed by the images. Most systems for interventional in vivo multispectral imaging use linear estimation approaches based on the modified Beer-Lambert law, as described in *A. Sassaroli* and *S. Fantini. Comment on the modified Beer-Lambert law for scattering media. PhysMed Biol,* 49(14):N255-257 (2004). However, while these methods are fast, they are restricted to estimating oxygenation, but no perfusion, they require small multispectral bandwidths and they also rely on a number of unrealistic assumptions regarding tissue composition that lead to imprecise results. More sophisticated ex vivo tissue analysis methods employ highly accurate Monte Carlo methods for more accurate assessment of physiological parameters.

The drawback of these methods is that they are too slow for real-time estimation of tissue parameters when dealing with high-resolution multispectral images; they are thus not suited for application during surgery or interventional procedures.

Finally, known methods for functional imaging using multispectral information require illumination of the tissue under highly specified illumination conditions. So far, it has been difficult to apply this technique under varying lighting conditions, which currently limits the versatility and practical applicability of the method. Varying light conditions may for example occur in an operating room setting, where different light sources with different spectra are simultaneously in use, and where a composition of light on the tissue changes when the patient or one of the light sources is moved.

SUMMARY OF THE INVENTION

The problem underlying the invention is to provide a method and a system for functional imaging that overcomes one or more of the above-mentioned deficiencies. This problem is solved by a method according to the claims and a system according to the claims. Preferred embodiments are defined in the dependent claims.

According to one aspect of the invention, a method of generating one or more augmented images of tissue of a patient undergoing open surgery is provided, wherein each augmented image associates at least one tissue parameter with a region or pixel of the image of the tissue. The method comprising the following steps:

estimating a spectral composition of light illuminating a region of interest of the tissue, obtaining one or more multispectral images of the region of interest, and applying a machine learning based regressor or classifier to the one or more multispectral images, or to an image derived from said multispectral image, to thereby derive one or more tissue parameters associated with image regions or pixels of the corresponding multispectral image, wherein said regressor or classifier has been trained to predict the one or more tissue parameters from a multispectral image under a given spectral composition of illumination. Note that wherever reference is made to predict one or more tissue parameters from "a multispectral image", it is understood that the tissue parameter can also be predicted or derived based on a plurality of images, in particular a time series of images, also optionally taking in account the time evolution thereof. In other words, wherever applicable, whenever reference is made to deriving a tissue parameter from "an image", it is understood, without further mention, that this could also be derived from a time series of images.

Herein, the regressor or classifier is applied either to the multispectral image itself, or to a processed version thereof, which is referred to as an "image derived from said multispectral image" in the present disclosure. For simplicity, in the following, this distinction is not explicitly made, i.e. whenever reference is made to a regressor or classifier being applied to the "multispectral image", it is to be understood that it is applied either to the multispectral image itself or an image derived therefrom, for example a multispectral image that has been subjected to some sort of segmentation or the like.

Depending on the type of tissue parameter, the method may employ a regressor, which allows for determining tissue parameters from a continuous range, such as an oxygenation value, or a classifier, which could represent for example the recognition of one of a predetermined set of organs to be recognized with the help of the multispectral images. In the following, sometimes reference will be made to a "regressor" only for brevity, but it is to be understood that where applicable, depending on the type of tissue parameter, the respective disclosure also applies to a classifier, without further mention.

In the present invention, the regressor or classifier employed is made to match the estimated spectral composition of light illuminating said region of interest of the tissue by one of three possible variants.

According to a first variant, the regressor or classifier is selected among a plurality of regressors or classifiers that have been previously trained for different training illuminations, such that the spectral composition of the training illumination is the most similar to the estimated spectral composition of said light illuminating said region of interest.

According to a second variant, the obtained multispectral image is transformed based on information derived from the estimated spectral composition of the light illuminating said region of interest, and a standard regressor or classifier is applied to the transformed multispectral image, which has been trained under a standard illumination, wherein the transformation is capable of compensating a change in the multispectral image due to a deviation in the spectral composition of the illumination from the standard illumination.

Finally, in a third variant, an already trained regressor or classifier may be retrained using simulation data that is adapted to the estimated spectral composition of light illuminating said region of interest. Namely, according to preferred embodiments of the invention, the data used for training is obtained by means of simulation in a way described in more detail below, and in this simulated data, some assumption about the spectral composition of the illumination light is made. The estimated spectral composition of the light will generally deviate from the illumination spectrum used in the simulation of training data, but the simulated training data can be adapted to account for this deviation. Based on this adapted simulation data, the regressor or classifier that was previously trained based on a different illumination spectrum can be retrained, such as to provide correct tissue parameters from images with the deviating illumination. The inventors have observed that using efficient ways of retraining, based on so-called transfer learning, this retraining can be carried out in surprisingly short timeframes, which may be acceptable for some practical applications. However, this third variant is still much more time-consuming to carry out than the first two variants, which for this reason are currently preferred.

Accordingly, in all three variants, a suitable regressor or classifier can be applied to the multispectral image, in spite of the fact that the illumination of the tissue in the region of interest may not be known in advance, or can even change over time. This makes the MSI-based augmented imaging suitable for applications in open surgery, where the lighting conditions in the region of interest will typically vary.

Note that in particularly preferred embodiment, two or even all three of these variants can be combined, such that an ensemble of regressors/classifiers is obtained, which can be applied to the multispectral image, and the tissue parameters to be actually used in the augmented image can e.g. be selected from or calculated from the tissue parameters derived based on the individual regressors/classifiers.

While reference is made herein to one region of interest, it is to be understood that there could be plural regions of interest.

In the present disclosure, both the term "augmented imaging" as well as the term "tissue parameter" have a broad meaning. Augmented images are understood herein as images providing information in addition to the image itself, and this information is represented by a tissue parameter. Herein, the term "image" merely expresses the fact that the tissue parameter is associated with a pixel or with a certain region within the multispectral image, but it does not imply that the tissue parameters must be presented to the user as a "visual image".

One example for such additional information is functional information characterizing the functional state of the tissue. Accordingly, one variant of "augmented images" could be referred to as "functional images", and the corresponding "tissue parameter" would then be a "functional parameter". Examples for such "functional parameters" are e.g. the oxygenation or blood volume fraction mentioned in the background section of the application above. Augmented images according to the invention may also provide physiological information, for example a presence or concentration of lipids, or a presence or concentration of melanine, and in this case, the "tissue parameter" could be a "physiological parameter". These functional or physiological parameters may be associated with individual pixels of the multispectral image, where a pixel could however correspond to a "multispectral pixel" comprised of a group of of sensor pixels configured for measuring an intensity of received light in a corresponding spectral range, as will be described below in more detail with reference to a specific embodiment. However, these functional or physiological parameters could likewise be associated with certain regions within the multispectral image, wherein said region may consist of a plurality of multispectral pixels. An example of such regions is a so-called "superpixel" described below. Accordingly, in preferred embodiments, said at least one tissue parameter comprises one or more of the following: an oxygenation, a blood volume fraction, a presence or concentration of lipids, a presence or concentration of melanine, a presence or concentration of bile, a presence or density of collagen or elastin, a presence or concentration of water, a presence of artificial dyes, in particular methylene blue or a parameter derived from any or any combination thereof.

However, the "tissue parameter" may alternatively comprise a tissue classification parameter, representing e.g. morphological information. For example, the tissue classification parameter could designate one out of various organs to be identified in the multispectral image, designate necrotic tissue, designate cancerous tissue, in particular cancerous lymph node tissue, and/or the stage thereof (benign or malign), or designate polyps. In cases where the tissue parameter represents morphological information, the tissue parameter will typically not be associated with individual pixels, but with certain regions within the multispectral image, for example a region corresponding to a given organ identified within the image by means of a suitable classifier. In these examples, applying the machine learning based classifier to the multispectral image may include a step of segmenting the image according to morphological features to be recognized, such as organs or the like. The segmentation may be an inherent step carried out when the classifier is applied to the multispectral image.

In some embodiments, the tissue parameter may be a parameter designating different materials and/or tooth decay in dental applications.

In other embodiments, the tissue parameter may be a landmark-indicating-parameter designating key landmarks, in particular nerves or important vessels, which may assist a surgeon in avoiding to inadvertently injuring the same. Providing such landmark-indicating-parameter associated with pixels of regions within the multispectral image is again a type of morphological imaging, and could involve a step of segmenting the image.

In some embodiments, the additional information in the augmented image may represent an event, for example bleeding, tissue inflammation or the presence of smoke, which would call for immediate action. For example, if smoke is detected in an endoscopic application, this could trigger an automatic ventilation to remove the smoke for clearer vision. Accordingly, the tissue parameter may be an event parameter indicating the presence of bleeding, or a parameter indicating the presence of smoke.

In some embodiments, tissue parameter may be a neurological parameter representing sensory evoked potentials. The inventors have discovered that sensory evoked potentials may lead to chemical/biological process in brain tissue that can be detected by multispectral images.

Finally, in some embodiments, the tissue parameter may be a prediction-of-event parameter, predicting a medical event, for example a kidney failure. Note that with regard to the cases where the tissue parameter represents an event or the prediction of an event, the tissue parameter may be associated with the entire multispectral image, which would be a special case of the "image region" with which the tissue parameter is associated.

In the present disclosure, the step of estimating the spectral composition of illuminating light has a broad meaning, and covers any conceivable way by which the spectral composition can be determined. The typical situation in open treatment, in particular open surgery, is that there is some light for illuminating the patient in the operating room, which is beyond control of the system disclosed herein, and this composition is to be estimated, typically by some type of measurement. In the alternative, there could be embodiments where the spectrum of illumination light is actively controlled, for example by controlling intensities of different light sources with different spectra, or by applying selected filters or the like. In cases like this, the step of "estimating a spectral composition of illuminating light" could amount to computing the spectral composition based on the control parameters determining the spectral composition, i.e. without actually having to measure the spectrum. However, in this case too, it is important to match the regressor or regressors used to the illumination spectrum currently employed, in a manner described above.

In a preferred embodiment, said step of estimating a spectral composition of illuminating light is based on light that is specularly reflected from said region of interest of the tissue, or from a region close to said region of interest of the tissue. This allows for obtaining the spectral composition of the light that is actually used for illuminating the region of interest, obtained at the region of interest. Note that due to the sterility requirement at the region of interest, it would be difficult or even impossible to use a white balance standard or the like.

These difficulties can be avoided by basing the spectral composition estimate on specularly reflected light. Moreover, while it is preferred that the estimation of the spectral composition of illuminating light is based on light that is specularly reflected from said region of interest of the tissue itself, it is also possible to rely on light that is specularly reflected from a region that is only "close" to said region of interest. Herein, "close to" means sufficiently close that it can be reasonably assumed that the spectral composition of the light is the same or practically the same as at the region of interest. In practice, this could for example mean less than 50 cm, preferably less than 30 cm away from said region of interest.

In a preferred embodiment, the method further comprises a step of identifying regions of specular reflection within a multispectral image of said region of interest of the tissue, or a region close to said region of interest of the tissue. In some embodiments, said method further comprises a step of transforming said multispectral image to a lower dimensional color space, in particular HSI (hue, saturation, intensity) color space. The HSI color space is particularly suitable for determining specular image regions, as it separates color from intensity and saturation.

In a preferred embodiment, the method further comprises a step of sorting regions of specular reflection according to size. Some of the spectral regions may be formed by single pixels or a region of few adjacent pixels only, which tend to be outliers and not suitable for reliably estimating the illumination light source spectrum. Accordingly, particularly small specular regions should be discarded. On the other hand, in practice it is found that the largest connected region within the segmented image is often in reality formed by the effusive background, and should therefore likewise be discarded. Accordingly, in a preferred embodiment, the first to n-th largest connected regions of specular pixels are determined, wherein the largest connected region of specular pixels is typically the second largest connected region within the segmented image.

In a preferred embodiment, the method further comprises a step of subjecting identified regions of specular reflection to morphologic dilation to thereby ensure that they include a predetermined number or percentage of non-saturated pixels. In practice, it is seen that specular regions may contain values, which do not give useful information regarding the spectrum, because part of the spectrum is truncated by the saturation of the corresponding pixel sensor element. However, it can be assumed that in the neighborhood of a spectral region, diffusing specular components are mixed, and using morphologic dilatation, these neighborhoods can be incorporated into the region of specular reflection, to thereby decrease the fraction of saturated/overexposed pixels. By applying morphologic dilation, the general shape of the specular region may be maintained.

Preferably, the method further comprises the step of separating, within an identified region of specular reflection within the multispectral image, contributions from specular reflection from contributions from diffused reflection. Namely, in practice, what is identified as "specular regions" will always contain some degree of diffused reflection, which, unlike specular reflection, does not exhibit the same spectral composition as the illumination light. Accordingly, in preferred embodiments, the contributions from specular and diffused reflection are separated, such that the estimate of the spectral composition is based on the truly specular component only. In a preferred embodiment, the separation is done using a blind source separation method, such as principal component analysis (PCA) or independent component analysis (ICA), as explained in more detail below. In alternative embodiments, however, the separation may e.g. be carried out based on multiple linear regression.

For estimating said spectral composition of the illuminating light, in a preferred embodiment, multispectral images of said region of interest are recorded with a lower exposure than the multispectral images to which said regressor or classifier is applied. The inventors have noticed that using lower exposures than those that are optimum for recording the multispectral images for deriving tissue parameters, the spectral composition of the illuminating light source can be determined based on specular highlights with particularly high precision. Herein, the lower exposure multispectral images may e.g. be recorded with a lower exposure time and/or with a smaller aperture opening than the multispectral images to which said regressor or classifier is applied. In preferred embodiments, the exposure time and/or aperture size is chosen such that the intensity is decreased by at least 20%, preferably by at least 40%, and most preferably by at least 60% as compared to the intensity obtained for the exposure used for recording the functional images, i.e. the multispectral image to which said regressor or classifier is applied.

In a preferred embodiment, said spectral composition is estimated based on a selected number of pixels or pixel groups, wherein said pixels or pixel groups are selected from said lower exposure image according to a selection criterion ensuring that the pixel or pixel group has a high, and in particular a highest possible lightness, under the provision that the image detector used for recording the image is not saturated for any of the spectral components of the pixel or pixel group. Herein, the "lightness" is a measure for the average intensity of the pixel or pixel group over all of its spectral components. In this embodiment, a "selection criterion" is used which fulfils two functions. First of all, it ensures that only unsaturated pixels are considered for the spectral composition estimation. Namely, even if lower exposures are used, there may be pixels for which at least some color channels of the corresponding detector are saturated, thereby cutting off part of the spectral intensity and thereby failing to truly represent the actual light spectrum. This is also referred to as "specular highlight segmentation" herein. The specular highlight segmentation may also comprise a step of sorting out pixels having too low intensities, for example intensities only resembling the dark current, since these pixels will not qualify for the spectral composition estimation anyhow, and can be dismissed to reduce the size of pixels or pixel groups to consider in the selection. The second function is to select among the remaining pixels those pixels or pixel groups that have particularly high lightness, because such high lightness is indicative of specular reflection. For example, in one embodiment, the pixels associated with the $N_P$ highest lightness values can be selected among the "valid pixels", i.e. those that were not discarded in a specular highlight segmentation. A suitable value for $N_P$ can be determined empirically, in preferred embodiments, it may be between 50 and 250, preferably between 80 and 170. However, this is just one exemplary selection criterion, and any selection criterion that allows for discarding saturated pixels and for choosing pixels with high lightness, i.e. specular highlights, may be used.

This embodiment can be implemented very efficiently, with moderate computational and structural effort, as will become apparent from the description of a specific example below, and at the same time allows for a very precise estimation of the spectral composition of the illumination, thereby allowing to reliably predict tissue parameters under various and possibly varying illumination conditions.

In a preferred embodiment, said multispectral image comprises a number of k color channels, and the method further comprises a step of transforming the spectral information from said k color channels, or a subset thereof, to a quasi-continuous spectrum. Obtaining a quasi-continuous spectrum is particularly helpful for the second variant of the invention, in which the obtained multispectral image is transformed—based on information derived from the estimated spectral composition of the light illuminating said region of interest—for use with a standard regressor or classifier. For this variant, a transformation is needed which is capable of compensating a change in the multispectral image due to a deviation in the spectral composition of the illumination from the standard illumination. This transformation can be best determined if a continuous or at least quasi-continuous spectrum of the actual illumination light is available. In a preferred embodiment, the wavelengths within said quasi-continuous spectrum are preferably separated by no more than 10 nm, preferably by no more than 5 nm and most preferably by no more than 3 nm.

In a preferred embodiment, the one or more augmented images is a series of augmented images generated consecutively at a rate of 25 Hz or above, preferably at a rate of 75 Hz or above. According to this embodiment, the augmented images can be obtained at what could be considered a "video rate", allowing for immediate feedback to the surgeon. Moreover, such video rate imaging can keep up with motion of the tissue occurring inevitably during surgery and reduce or avoid blurring of the augmented image.

In a preferred embodiment, the multispectral images are obtained using a multispectral sensor, said multispectral sensor comprising multispectral pixels, wherein each multispectral pixel comprises a group of sensor pixels configured for measuring an intensity of received light in a corresponding spectral range, thereby permitting to obtain a multispectral image in a single shot. Using such a multispectral sensor allows for higher imaging speeds as compared for example to a prior art embodiment employing a filter wheel, and also ensures that the various components of the spectrum are recorded precisely at the same point in time, i.e. avoiding any movement of the tissue between the recording of different image components, as can occur when using a filter wheel. Moreover, employing such a multispectral sensor allows for small and lightweight devices which are economically preferable over a device comprising a filter wheel. In a preferred embodiment, each multispectral pixel comprises a group of 3×3 or 4×4 sensor pixels.

In a preferred embodiment, said regressor or classifier is based on a convolutional neural network (CNN). The inventors have confirmed that CNN allows for very rapid calculation of the tissue parameters with moderate hardware expense, which is particularly important for embodiments employing video rate imaging. Moreover, CNN allow for an end-to-end processing of the spectral images and have shown to give very accurate results.

In order to obtain one or more tissue parameters associated with an image region or pixel of the corresponding multispectral image, in a preferred embodiment, said regressor or classifier is applied to a neighborhood covering more than said image region or pixel of said multispectral image. In this embodiment, it is exploited that CNNs provide the possibility to incorporate regions with a spatial extent into the estimation process. In this embodiment, the system can base functional estimation (or the determination of other tissue parameters) not only on one spectral measurement, i.e. one "image region" or "pixel" of the multispectral image, but on a neighborhood. In case of homogeneous tissue, moving from one (noisy) spectral measurement to an area is advantageous because this provides multiple (noisy) measurements to base further reasoning on.

In a preferred embodiment, said image region or pixel of the multispectral image is formed by a multispectral pixel of a multispectral sensor, wherein each multispectral pixel of said sensor comprises a group of sensor pixels configured for measuring an intensity of received light in a corresponding spectral range, and wherein said neighborhood to which the regressor or classifier is applied corresponds to a number of adjacent multispectral pixels of said multispectral sensor.

In a preferred embodiment, said regressor or classifier devised for applying to said neighborhood is trained using a simulated neighborhood, which is derived from copies of a simulated image region or pixel collectively covering said neighborhood, wherein said copies are subjected to individual noise and/or modifications accounting for tissue inhomogeneities.

In a preferred embodiment, said multispectral image comprises a number of k color channels, wherein said step of applying the regressor or classifier to the multispectral image comprises inputting k reflectance values obtained from the color channels of the multispectral image to the regressor or classifier. Herein, said reflectance values may be obtained from light sensor readings by subtracting a dark image recorded in complete darkness from the multispectral image, and preferably further normalizing the image by the difference of a white image obtained or obtainable from a standard white target and the dark image.

In a preferred embodiment, the method further comprises a step of deriving an RGB image from the multispectral image. The RGB image can be helpful for surgeon recognizing the region of interest on a display. In particular, in this embodiment it is not necessary to provide for an additional RGB imaging sensor.

In a preferred embodiment, said regressor or classifier is trained based on a forward model, which comprises a tissue model, a simulation of spectral reflectance that is characteristic for tissue modelled by said tissue model, and an adaption of said spectral reflectance to an imaging system which is used for recording the multispectral images. Herein, the simulation is preferably a Monte Carlo simulation, which gives the most accurate results.

Herein, said tissue model is preferably a layered tissue model comprising a plurality of layers, wherein each layer is characterized by a set of optically relevant tissue parameters, wherein said optically relevant tissue parameters preferably comprise a blood volume fraction, an oxygenation, the presence of a tumor, the presence or concentration of fat, the presence or concentration of melanine, the presence or concentration of bile, the presence or density of collagen or elastin, the presence or concentration of water, or the presence of artificial dyes, in particular methylene blue.

Said set of optically relevant tissue parameters preferably comprises one or more of a parameter quantifying an amount of scattering, a scattering power, which characterizes an exponential wavelength dependence of scattering, an anisotropy factor characterizing a directionality of scattering, a refractive index, and a layer thickness.

In a preferred embodiment, said adaption of said spectral reflectance to the imaging system comprises calculating, from the spectral reflectance of the modelled tissue, an estimate of an intensity associated with each color channel of said imaging system.

In a preferred embodiment, said calculating of said estimate of intensity associated with each color channel is based on one or more of a quantum efficiency of a camera or optical sensor used, information about the spectral composition of the illumination light, transmittance of optical components used, such as spectral filters, a nonlinear camera response function, and camera noise for each color channel.

In a preferred embodiment, for a given task, among a plurality of simulations, a subset of simulations are selected by comparison with measurement on real tissue, wherein the subset of simulations match the measurements better than the remainder of the simulations.

Generally, the training of the regressor or classifier is carried out based on simulated tissue data, because it can be generated in large amounts, allowing for a thorough training of the machine learning regressor/classifier. In contrast to this, obtaining reliable training data from measurements on actual tissue is by far more involved and hence limited in practice. In view of this, some of the present inventors have recently proposed a method called "domain adaption" which is particularly useful in the framework of the present invention, cf. S. J. Wirkert, A. S. Vemuri, H. G. Kenngott, S. Moccia, M. Götz, B. F. B. Mayer, K. H. Maier-Hein, D. S. Elson, and L. Maier-Hein. *Physiological Parameter Estimation from Multispectral Images Unleashed. In Medical Image Computing and Computer-Assisted Intervention—MICCAI 2017, Lecture Notes in Computer Science*, pages 134-141. Springer, Cham (2017). ISBN 978-3-319-66178-0 978-3-319-66179-7. Namely, if the regressor/classifier is intended for a given task, its performance can be improved if the training is carried out only on a subset of simulations which are selected based on a comparison with measurements on real tissue for this task, namely those simulations that match the actual measurements to some predetermined degree. This way, it can be ensured that the training data is indeed relevant for the real tissue to be analyzed.

In preferred embodiments, plural regressors or classifiers are applied to the one or more multispectral images, leading to plural results for possible tissue parameters, and the tissue parameters associated with the region or pixel of the image of the tissue is obtained by combining or selecting from said possible tissue parameters.

In preferred embodiments, said machine learning based regressor or classifier is suitable for providing a confidence value together with said prediction of said one or more tissue parameters, indicating a measure of confidence in the accuracy of the one or more tissue parameters.

In case the confidence value fails to meet a predefined confidence criterion, the method may comprise one or more of the following:
- the tissue parameters are not visualised in the augmented image,
- the tissue parameters are visualized in the augmented image, but together with an indication of the confidence,
- tissue parameters to be used in the augmented imaging are derived by a selection or a combination of values from one of
- different regions within the same image,
- same regions within different multispectral images of the same tissue obtained with different imaging setups, in particular with a different illumination spectrum and/or with different bands selected for the multispectral imaging, and
- same regions within the same multispectral to which different regressors or classifiers are applied.

Further, tissue parameters to be used in the functional imaging can be combined for example by forming an average value over a time series of images, or an average value within an image or a part of the image.

In other words, instead of a single regressor/classifier, an ensemble of regressors/classifiers may be applied to the same multispectral image. Herein, the above-mentioned "combination of values" may be an uncertainty-based aggregation of values, e.g. a weighted mean of inferred values taken from a region of interest, or the like.

In preferred embodiments, said regressor or classifier is capable of deriving a probabilistic distribution of possible tissue parameters. Note that traditional machine learning methods generate a single "hypothesis" given a measurement, e.g. one plausible tissue parameter configuration given a measured spectrum. However, in a preferred embodiment, the machine learning algorithm is directed to deriving multiple "plausible hypotheses" instead, i.e. a probability distribution of possible tissue parameters. Herein, the term "distribution" has a broad meaning, and does not imply any lower boundary on the number of different possible tissue parameters. More detailed description on the underlying methology is described in Simon A. A. Kohl, Bernardino Romera-Paredes, Clemens Meyer, Jeffrey De Fauw, Joseph R. Ledsam, Klaus H. Maier-Hein, S. M. Ali Eslami, Danilo Jimenez Rezende, Qlaf Ronneberger *A Probabilistic U-Net for Segmentation of Ambiguous Images,* 2018, arXiv: 1806.050034v1. However, other probabilistic approaches, e.g. approximate Bayesian computation may be used to tackle inverse problems, whose forward process is well-understood. In such embodiments too, a distribution of plausible parameter configurations (rather than one single estimate) is outputted for a given spectrum. If the distribution is uni-modal (and not too broad), the inversion of the acquired spectrum can be regarded a well-posed problem. Otherwise, the problem is ambiguous and the different modes of the distribution are outputted as alternative hypotheses, or in other words, "multiple plausible solutions".

In case said probability distribution of possible tissue parameters exhibits plural modes and/or is broader than a predetermined threshold, in preferred embodiments, at least one new multispectral image is generated with a different imaging set up, in particular with a different illumination spectrum and/or different bands selected for the multispectral imaging.

It is generally believed that for obtaining meaningful tissue parameters from multispectral images, a large number of bands are needed. Generally, "multispectral images" are understood to be images having more than three wavelength bands, usually much more than three wavelength bands, and at least a few wavelength bands different from the ordinary three wavelengths used for RGB imaging. While a large number of wavelength bands assists in the derivation of tissue parameters, this usually comes at the price of reduced imaging speed (if the wavelength bands are recorded sequentially) or a reduced spatial resolution (if large number of sensor pixels for a correspondingly large number wavelength bands have to be placed next to each other on the image sensor), or both. However, the inventors have determined that for the particular application of oxygenation estimation, very accurate results can be obtained when using a surprisingly small number of wavelength bands, if these bands are properly chosen. The novel method how to determine these most suitable wavelength bands is described in more detail below. Accordingly, in a preferred embodiment, said tissue parameter is related to oxygenation or blood volume fraction, and said multispectral image comprises at least three, preferably at least four spectral components whose center wavelengths fall into one of the following wavelength intervals: 495-505 nm, 535-545 nm, 550-570 nm, 575-585 nm, and 590-610 nm.

If all five wavelength bands are employed in the multispectral imaging, oxygenation results with excellent accuracy can be obtained. Further analysis of the inventors revealed that in fact any combination of 4 out of the 5 proposed bands would give excellent results for oxygenation estimation. This allows e.g. for designing a multispectral sensor where each multispectral pixel is formed by 2×2 single color pixel sensors, detecting light in corresponding four out of the above five bands. Surprisingly, the inventors could confirm that good oxygenation estimates can even be obtained when only three of the above five wavelengths are chosen. This allows for an even higher resolution, if the multispectral image sensor comprises only three single color pixel sensors. This image would still be regarded as "multispectral" in the framework of the present disclosure, because these wavelength bands are different from the bands used for RGB imaging. Moreover, in the multispectral image sensor, three types of single color pixel sensors located in respective three out of the above five bands could be combined with pixel sensors detecting light within different bands that are provided for other imaging purposes In a preferred embodiment, said augmented image is projected into the field of vision of goggles to be worn by a surgeon.

Herein, said goggles preferably further comprise one or more of the following components: a multispectral camera suitable for obtaining said one or more multispectral images of the region of interest, a microphone for receiving speech commands, a wireless data link for exchanging data with a computing device or a database, and a data processing unit suitable for one or more of applying said regressor or classifier to said multispectral image, recognizing gestures, particularly gestures indicating regions of interest for which augmented images are to be created, and controlling the display of augmented images in the field of view of the glasses, particularly in a way that the augmented image is overlaid with the actual scenery seen through the goggles.

In the previous embodiments, it has been shown how machine learning algorithms can be used to convert pixel-wise multispectral reflectance measurement to tissue parameters.

However, the accuracy of these algorithms can only be guaranteed if the multispectral images match the ones that have been seen by the machine learning algorithm during its training. In a preferred embodiment, the method further comprises a step of out of distribution detection (OoD), wherein said OoD detection comprises a step of determining information about the closeness of the multispectral image or parts of said multispectral image to a given training data set. By means of the OoD detection, it can be prevented that the machine learning algorithms present spurious results for tissue parameters caused by a lack of training on the tissue represented by the multispectral image.

In a preferred embodiment, said OoD detection is carried out using an OoD detection algorithm configured for assigning a numerical closeness value to multispectral information associated with said multispectral image or parts thereof, in particular associated with individual pixels or pixel groups. Herein, the multispectral information could for example be the spectrum determined for a certain pixel, but it could also be a quantity that is derived from said spectrum. Moreover, the multispectral information may be associated with single pixels, or groups of pixels, within an image, without accounting for interrelations between the spectra of individual pixels or individual pixel groups. However, in some embodiments, the OoD detection may be carried out on the full multispectral image or at least on regions thereof. Herein, the numerical value indicates the closeness of said spectral information to the corresponding spectral information in said given training data set.

There are various possibilities to assign a closeness of a sample to an underlying dataset, and the OoD detection of the invention is not limited to any specific one of them. However, in a preferred embodiment, said OoD detection algorithm comprises an ensemble of neural networks, and in particular invertible neural networks (INN). Each of said neural networks of the ensemble has been trained, on said given training data set, to transform a training data sample to a transformed data sample, such that the transformed training data matches a predetermined statistical distribution. Moreover, said OoD detection algorithm is configured to determine the numerical closeness value for a data sample by transforming said data sample with each neural network of said ensemble of neural networks to obtain an ensemble of transformed data samples, and determining said numerical closeness value as a measure indicative of the variance of said ensemble of transformed data sets.

Note that the neural networks of the ensemble are per se unrelated to any machine learning based classifier or regressor that is eventually to be used for determining functional parameters, except that it is trained using the same training data. Namely, the neural networks of the ensemble are not intended for predicting any biologically or medically meaningful parameters, but are instead simply trained to map a distribution of data samples to said predetermined statistical distribution, and are only used for this OoD analysis. The rationale behind this approach is that for a data sample that is close to those that have been considered during training, the neural networks of said ensemble will typically transform the data samples to transformed data samples which are similar to each other, and hence leading to a smaller variance, while this cannot be expected for data samples that are very different from anything the ensemble of neural networks have seen in their training.

In a preferred embodiment, said OoD detection algorithm uses the "widely applicable information criterion" (WAIC) to determine said numerical closeness value. References for the use of the WAIC in the literature are given in the more detailed description thereof below.

Herein, the WAIC, or a value derived therefrom, may be used as said numerical closeness value. The WAIC is defined as $$\mathrm{WAIC}(x) = \mathrm{Var}_\theta[\log p(x|\theta)] - E_\theta[\log p(x|\theta)],$$

wherein x is a data sample, θ are the parameters of the neural networks of said ensemble of neural networks, log p(x|θ) corresponds to said predetermined statistical distribution, and $E_\theta[\log p(x|\theta)]$ is an expectation term used for normalization purposes.

In a preferred embodiment, said predetermined distribution is a multivariate standard Gaussian defined as $$\log p(x|\theta) = -\tfrac{1}{2}\|f_\theta(x)\|^2 - n/2 \log(2\pi) + \log|\det Jf_\theta(x)|,$$

where $f_\theta$ represents a network of said ensemble of neural networks with corresponding network parameters θ, x is a data sample and $Jf_\theta$ denotes the Jacobian of the distribution. Note that the multivariate standard Gaussian just one example of a statistical distribution, that is attractive for computational purpose, but that other statistical solutions may likewise be used.

Moreover, note that other approaches to OoD detection may likewise be employed in the context of the present invention. In a preferred embodiment, the OoD detection algorithm is based on a variational autoencoder, as described in An, J., & Cho, S. (2015). *Variational autoencoder based anomaly detection using reconstruction probability. Special Lecture on IE,* 2(1). Simply put, an autoencoder is a neural network that is trained by unsupervised learning, and which is trained to learn reconstructions that are close to its original input. An autoencoder is composed of two parts, an encoder and a decoder. Autoencoder based anomaly detection is a deviation based anomaly detection method using semi-supervised learning. It uses the reconstruction error as the anomaly score. Data points with high reconstruction error are considered to be anomalies. Only data with normal instances are used to train the autoencoder. After training, the autoencoder will reconstruct normal data very well, while failing to do so with anomaly data which the autoencoder has not encountered. While simply speaking, a plain autoencoder only transforms features to a latent space and back, by looking at the reconstruction from the variational autoencoder it is possible to identify specific regions that are "abnormal" in cases where one trains on whole images, which may be particularly helpful.

Prior to or along with applying a regressor or classifier that has been trained with a given training data set, in preferred embodiments, said OoD detection is carried out to determine the closeness of the multispectral image or part of said multispectral image to said given training data set, or to a related training data set, and if the closeness is found to be insufficient, the functional tissue parameter is not determined or is marked as unreliable. This way, it can be avoided that tissue parameters are generated that cannot be relied on due to lack of relevant training. In case the closeness is found to be insufficient, in a related embodiment, it may be further checked whether the closeness with a training dataset associated with another regressor or classifier is better, and given the case, said another regressor or classifier may be applied to said multispectral image or parts of said multispectral image. In other words, in this embodiment, the OoD detection does not only allow for noticing situations where a given regressor or classifier may fail to make reliable predictions due to lack of relevant training for the multispectral images at hand, but also for identifying a regressor or classifier with more appropriate training. In particularly preferred embodiments, the training dataset associated with said another regressor or classifier corresponds to different illumination conditions. Indeed, changing illumination conditions, which may for example arise when a given light source in an operating room is switched on or off, or is moved closer to or further away from the site of intervention, are a scenario where the OoD detection is of particular value, to avoid that changing illumination conditions, such as different spectral compositions provided by different light sources, lead to errors in the prediction of tissue parameters. In other embodiments, the training dataset associated with said another regressor or classifier corresponds to a different tissue type. This way, it can be ensured that the most appropriate regressor or classifier is used for various tissue types. Note that this way, it is also possible to choose suitable regressors or classifiers for different parts of the multispectral image. This may be particularly important if there are different illumination conditions in different parts of the image, for example to different mixtures of contributions from different light sources, or if there there are different tissue types in the same image.

Note that one practical implementation would be to use the exact same training data for the OOD algorithm (i.e. the training data on which the ensemble of neural networks is trained) on the one hand, and the corresponding regressor or classifier on the other hand. However, this is not necessary, as long as the OOD algorithm and the regressor/classifier have been trained on similar training data, which was referred to as a "related dataset" above. Similar training data could for example be two subsets of a larger set of training data, or training data which are generated in silico by different simulations of the same type of tissue model, or obtained by medical images that show the same medical or biological context, for example the very same type of tissue with the same oxygenation value, or same ranges of oxygenation values. In view of this, said OoD detection need not necessarily be carried out to determine the closeness of the multispectral image or part of said multispectral image to said (same) given training data set, but could be carried out to determine the closeness of the multispectral image to a "related training data", as was specified above.

Prior to applying a regressor or classifier to a multispectral image or part thereof, a preferred embodiment comprises a step of using the OoD detection for selecting among a plurality of regressors or classifiers, each associated with a corresponding training data set, the regressor or classifier to whose training data the multispectral image or part of said multispectral image is the closest to. The method further comprises applying said selected regressor or classifier to the multispectral image or part thereof. In this embodiment, the OoD detection is used to automatically determine the most appropriate regressor or classifier for the multispectral images at hand. Again, in preferred embodiments, said training datasets associated with said plurality of regressors or classifiers preferably correspond to different illumination conditions, or to different tissue types.

In a preferred embodiment, said said OoD detection is carried out repeatedly over time, to thereby detect a change in conditions, in particular illumination conditions, by means of a change in closeness of the multispectral image with a given set of training data. This way, changing conditions can be constantly monitored and detected before errors occur. Note that while it can be computationally quite expensive to establish the OoD detection algorithm, for example due to the training of the ensemble of neural networks in the preferred embodiment, applying the OoD detection algorithm is of negligible computational effort, such that it can be carried out continuously or at high frequencies to allow for a close monitoring of a change in conditions.

A further aspect of the present invention relates to a system for generating one or more augmented images of tissue of a patient undergoing open surgery, wherein each augmented image associates at least one tissue parameter with a region or pixel of the image of the tissue, said system comprising:
  an apparatus for estimating a spectral composition of light illuminating a region of interest of the tissue,
  a multispectral camera for obtaining one or more multispectral images of the region of interest,
  a computing device comprising a machine learning module for applying a machine learning based regressor or classifier to the one or more multispectral images or an image derived from said multispectral image, to thereby derive one or more tissue parameters associated with image regions or pixels of the corresponding multispectral image, wherein said regressor or classifier has been trained to predict the one or more tissue parameters from a multispectral image under a given spectral composition of illumination, wherein the computing device is configured to make the regressor or classifier employed to match the estimated spectral composition of light illuminating said region of interest of the tissue by one of
  selecting the regressor or classifier among a plurality regressors or classifiers that have been previously trained for different training illuminations, such that the spectral composition of the training illumination is the most similar to the estimated spectral composition of said light illuminating said region of interest, or
  transforming the obtained multispectral image based on information derived from the estimated spectral composition of the light illuminating said region of interest and applying a standard regressor or classifier to the transformed multispectral image, which has been trained under a standard illumination, wherein the transformation is capable of compensating a change in the multispectral image due to a deviation in the spectral composition of the illumination from the standard illumination, or
  retraining an already trained regressor or classifier using simulation data that is adapted to the estimated spectral composition of light illuminating said region of interest.

Herein, said apparatus for estimating a spectral composition can comprise a computing device, which is programmed to obtain an estimate for the spectral composition of the illumination light, for example based on multispectral images obtained using said multispectral camera of the system. The computing device could be a microprocessor, an FPGA or the like. Moreover, the apparatus could also be formed by the same computing device comprising said machine learning module, which in this case further comprises a module for the estimation of spectral composition.

Preferably, said system further comprises a display device, wherein said system is configured to display said augmented image, wherein said system is in particular configured to display the augmented image together with or in an overlaid fashion with an RGB image of said region of interest.

In another preferred embodiment, the system comprises goggles, wherein said system is configured to project said augmented image into the field of view of said goggles.

In a preferred embodiment, said goggles further comprise one or more of the following components:
- a multispectral camera suitable for obtaining said one or more multispectral images of the region of interest,
- a microphone for receiving speech commands,
- a wireless data link for exchanging data with a computing device or a database, and a data processing unit suitable for one or more of applying said regressor or classifier to said multispectral image, recognizing gestures, particularly gestures indicating regions of interest for which augmented images are to be created, and controlling the display of augmented images in the field of view of the glasses, particular in a way that the augmented image is overlaid with the actual scenery seen through the goggles.

In a preferred embodiment of the system, said at least one tissue parameter comprises one or more of the following: an oxygenation, a blood volume fraction, a presence or concentration of lipids, a presence or concentration of melanine, a presence or concentration of bile, a presence or density of collagen or elastin, a presence or concentration of water, or a presence of artificial dyes, in particular methylene blue, or a parameter derived from any or any combination thereof,
- a tissue classification parameter, in particular a tissue classification parameter designating various organs, designating necrotic tissue, designating cancerous tissue, in particular cancerous lymph node tissue, and/or the stage thereof, or designating polyps,
- a parameter designating different materials and/or tooth decay in dental applications,
- a landmark indicating parameter designating key landmarks, in particular nerves or important vessels;
- an event parameter indicating the presence of bleeding, or a parameter indicating the presence of smoke, a
- a neurological parameter representing sensory evoked potentials, or
- a prediction of event parameter, predicting a medical event.

In a preferred embodiment, said apparatus for estimating a spectral composition of illuminating light is configured for carrying out said estimation based on light that is specularly reflected from said region of interest of the tissue, or from a region close to said region of interest of the tissue.

Preferably, said apparatus for estimating spectral composition is configured for identifying regions of specular reflection within a multispectral image of said region of interest of the tissue, obtained with said multispectral camera, or a region close to said region of interest of the tissue.

Preferably, said apparatus for estimating spectral composition is further configured for transforming said multispectral image to a lower dimensional color space, in particular HSI color space.

In a preferred embodiment, said apparatus is further configured for sorting regions of specular reflection according to size, wherein preferably, the first to n-th largest connected regions of specular pixels are determined, where n is an integer number that is smaller than the total number of regions of connected specular pixels.

In a preferred embodiment, said apparatus is further configured for subjecting identified regions of specular reflection to morphologic dilation to thereby ensure that they include a predetermined number or percentage of non-saturated pixels.

In a preferred embodiment, said apparatus is further configured for separating, within an identified region of specular reflection within the multispectral image, contributions from specular reflection from contributions from diffused reflection, in particular using a principal component analysis or an independent component analysis.

In a preferred embodiment of the system, for estimating said spectral composition of the illuminating light, the system is preferably configured for recording multispectral images of said region of interest with a lower exposure than the multispectral images to which said regressor or classifier is applied.

In a preferred embodiment said system is configured for recording said lower exposure multispectral images with a lower exposure time and/or a smaller aperture opening than the multispectral images to which said regressor or classifier is applied, wherein preferably, the exposure time and/or aperture size is set such that the intensity is decreased by at least 20%, preferably by at least 40%, and most preferably by at least 60% with respect to the intensity obtained for the exposure used for recording the multispectral images to which said regressor or classifier is applied.

In a preferred embodiment, said system is configured for estimating said spectral composition based on a selected number of pixels or pixel groups, wherein said system is configured for selecting said pixels or pixel groups from said lower exposure image according to a selection criterion ensuring that the pixel or pixel group has a high, and in particular a highest possible lightness, under the provision that the image detector used for recording the image is not saturated for any of the spectral components of the pixel or pixel group, wherein the lightness is a measure for the average intensity of the pixel or pixel group over all of its spectral components.

In a preferred embodiment of the system, said multispectral image comprises a number of k color channels, and wherein the apparatus further configured for transforming the spectral information from said k color channels, or a subset thereof, to a quasi-continuous spectrum, wherein the wavelengths within said quasi-continuous spectrum are preferably separated by no more than 10 nm, preferably by no more than 5 nm and most preferably by no more than 3 nm.

In preferred embodiments, the one or more augmented images is a series of augmented images generated consecutively at a rate of 25 Hz or above, preferably at a rate of 75 Hz or above.

In a preferred embodiment of the system, the multispectral camera comprises a multispectral sensor, said multispectral sensor comprising multispectral pixels, wherein each multispectral pixel comprises a group of sensor pixels configured for measuring an intensity of received light in a corresponding spectral range, thereby permitting to obtain a multispectral image in a single shot, wherein preferably, each multispectral pixel comprises a group of 3×3 or 4×4 sensor pixels.

In a preferred embodiment of the system, said regressor or classifier is based on a convolutional neural network.

In order to obtain one or more tissue parameters associated with an image region or pixel of the corresponding multispectral image, said machine learning module is preferably configured for applying said regressor or classifier to a neighborhood covering more than said image region or pixel of said multispectral image.

In a preferred embodiment, said image region or pixel of the multispectral image is formed by a multispectral pixel of a multispectral sensor of said multispectral camera, wherein each multispectral pixel of said sensor comprises a group of sensor pixels configured for measuring an intensity of received light in a corresponding spectral range, and wherein said neighborhood to which the regressor or classifier is applied by said machine learning module corresponds to a number of adjacent multispectral pixels of said multispectral sensor.

In a preferred embodiment, said regressor or classifier devised for applying to said neighborhood is trained or obtainable by training using a simulated neighborhood, which is derived from copies of a simulated image region or pixel collectively covering said neighborhood, wherein said copies are subjected to individual noise and/or modifications accounting for tissue inhomogeneities.

In a preferred embodiment, said multispectral image comprises a number of k color channels, wherein said machine learning module is configured for carrying out said step of applying the regressor or classifier to the multispectral image by inputting k reflectance values obtained from the color channels of the multispectral image to the regressor or classifier.

In a preferred embodiment of the system, said machine learning module is configured for obtaining said reflectance values from readings of said a sensor of said camera by subtracting a dark image recorded in complete darkness from the multispectral image, and preferably further normalizing the image by the difference of a white image obtained or obtainable from a standard white target and the dark image.

In a preferred embodiment of the system, said machine learning module or a separate module is configured for deriving an RGB image from the multispectral image.

In a preferred embodiment of the system, said regressor or classifier employed by said machine learning module is trained based on a forward model, which comprises a tissue model, a simulation of spectral reflectance that is characteristic for tissue modelled by said tissue model, and an adaption of said spectral reflectance to an imaging system which is used for recording the multispectral images, wherein said simulation of the spectral reflectance is preferably a Monte Carlo simulation.

Herein, said tissue model is preferably a layered tissue model comprising a plurality of layers, wherein each layer is characterised by a set of optically relevant tissue parameters, wherein said optically relevant tissue parameters preferably comprises one or more of a blood volume fraction, an oxygenation, the presence of a tumor, the presence or concentration of gall, the presence or concentration of fat, the presence or concentration of melanine, the presence or concentration of bile, the presence or density of collagen or elastin, the presence or concentration of water, or the presence of artificial dyes, in particular methylene blue.

In addition, said set of optically relevant tissue parameters preferably further comprises one or more of a parameter quantifying an amount of scattering, a scattering power, which characterizes an exponential wavelength dependence of scattering, an anisotropy factor characterizing a directionality of scattering, a refractive index, and a layer thickness.

In addition or alternatively, said adaption of said spectral reflectance to the imaging system preferably comprises calculating, from the spectral reflectance of the modelled tissue, an estimate of an intensity associated with each color channel of said imaging system.

Herein, said calculating of said estimate of intensity associated with each color channel is preferably based on one or more of a quantum efficiency of a camera or optical sensor used, information about the spectral composition of the illumination light, transmittance of optical components used, a nonlinear camera response function, and camera noise for each color channel.

In a preferred embodiment of the system, said regressor or classifier has been trained for a given task, wherein the training was based on a subset of simulations from a larger set of simulations, wherein said subset of simulations was selected by comparison with measurements on real tissue, wherein the subset of simulations matched the measurements better than the remainder of the simulations.

In a preferred embodiment of the system, said data processing unit is suitable for applying plural regressors or classifiers to the one or more multispectral images, leading to plural results for possible tissue parameters, and for obtaining the tissue parameters associated with the region or pixel of the image of the tissue by combining or selecting from said possible tissue parameters.

In a preferred embodiment, said machine learning based regressor or classifier is suitable for providing a confidence value together with said prediction of said one or more tissue parameters, indicating a measure of confidence in the accuracy of the one or more tissue parameters.

Herein, in case the confidence value fails to meet a predefined confidence criterion, the data processing unit is preferably configured to carry out one or more of the following: not visualising the tissue parameters in the augmented image, visualising the tissue parameters in the augmented image, but together with an indication of the confidence, deriving tissue parameters to be used in the augmented imaging by a selection or a combination of values from one of
- different regions within the same image,
- same regions within different multispectral images of the same tissue obtained with different imaging setups, in particular with a different illumination spectrum and/or with different bands selected for the multispectral imaging,
- same regions within the same multispectral to which different regressors or classifiers are applied.

In a preferred embodiment of the system, said regressor or classifier is capable of deriving a probabilistic distribution of possible tissue parameters.

Herein, in case said probability distribution of possible tissue parameters exhibits plural modes and/or is broader than a predetermined threshold, the system is preferably further configured for generating at least one new multispectral image with a different imaging set up, in particular with a different illumination spectrum and/or different bands selected for the multispectral imaging.

In a preferred embodiment of the system, said tissue parameter is related to oxygenation or blood volume fraction, and wherein said multispectral image comprises at least three, preferably at least four spectral components whose center wavelengths fall into one of the following wavelength intervals: 495-505 nm, 535-545 nm, 550-570 nm, 575-585 nm, and 590-610 nm.

In a preferred embodiment of the system, said computing device, or an additional computing device associated with the system is configured for carrying out an out of distribution detection (OoD), wherein said OoD detection comprises a step of determining information about the closeness of the multispectral image or parts of said multispectral image to a given training data set. In other words, the OoD detection can be carried out by the same computing device that also comprises said machine learning module, or it can be carried out by another computing device. The another computing device can be formed by one or more microprocessors, which is programmed to carry out the OOD detection.

In a preferred embodiment, said computing device or additional computing device is configured for carrying out said OoD detection using an OoD detection algorithm configured for assigning a numerical closeness value to multispectral information associated with said multispectral image or parts thereof, in particular associated with individual pixels or pixel groups, said numerical value indicating the closeness of said spectral information to the corresponding spectral information in said given training data set.

In a preferred embodiment, said OoD detection algorithm comprises an ensemble of neural networks, in particular invertible neural networks (INN), wherein each of said neural networks of the ensemble has been trained, on said given training data set, to transform a training data sample to a transformed data sample, such that the transformed training data matches a predetermined statistical distribution, and wherein said OoD detection algorithm is configured to determine the numerical closeness value for a data sample by transforming said data sample with each neural network of said ensemble of neural networks to obtain an ensemble of transformed data samples, and determining said numerical closeness value as a measure indicative of the variance of said ensemble of transformed data sets.

In a preferred embodiment, said OoD detection algorithm uses the "widely applicable information criterion" (WAIC) to determine said numerical closeness value, and wherein in particular, the WAIC, or a value derived therefrom, is used as said numerical closeness value, wherein said WAIC is defined as $$\mathrm{WAIC}(x) = \mathrm{Var}_\theta[\log p(x|\theta)] - E_\theta[\log p(x|\theta)],$$

wherein x is a data sample, $\theta$ are the parameters of the neural networks of said ensemble of neural networks, log $p(x|\theta)$ corresponds to said predetermined statistical distribution, and $E_\theta$ [log $p(x|\theta)$] is an expectation term used for normalization purposes.

In a preferred embodiment, said predetermined distribution is a multivariate standard Gaussian defined as $$\log p(x|\theta) = -\tfrac{1}{2}\|f_\theta(x)\|^2 - n/2\, \log(2\pi) + \log|\det Jf_\theta(x)|,$$

where $f_\theta$ represents a network of said ensemble of neural networks with corresponding network parameters $\theta$, x is a data sample and $Jf_\theta$ denotes the Jacobian of the distribution.

In a preferred embodiment, said OoD detection algorithm is based on a variational autoencoder.

In a preferred embodiment, prior to or along with applying a regressor or classifier that has been trained with a given training data set, said computing device or additional computing device is configured for carrying out said OoD detection to determine the closeness of the multispectral image or part of said multispectral image to said given training data set, or to a related training data set, and to not determine the functional tissue parameter or to mark it as unreliable, if the closeness is found to be insufficient, wherein, in case the closeness is found to be insufficient, the computing device or additional computing device is further configured to check whether the closeness with a training dataset associated with another regressor or classifier is better, and given the case, to apply said another regressor or classifier to said multispectral image or parts of said multispectral image, wherein in particular, said training dataset associated with said another regressor or classifier corresponds to different illumination conditions or to a different tissue type.

In a preferred embodiment, prior to applying a regressor or classifier to a multispectral image or part thereof, said computing device or additional computing device is configured for using the OoD detection for selecting among a plurality of regressors or classifiers, each associated with a corresponding training data set, the regressor or classifier whose training data the multispectral image or part of said multispectral image is closest to, and for applying said selected regressor or classifier to the multispectral image or part thereof, wherein said training datasets associated with said plurality of regressors or classifiers preferably correspond to different illumination conditions or different tissue types.

The computing device or additional computing device is preferably configured for carrying out said OoD detection repeatedly over time, to thereby detect a change in conditions, in particular illumination conditions, by means of a change in closeness of the multispectral image with a given set of training data.

SHORT DESCRIPTION OF THE FIGURES

Figure 6:
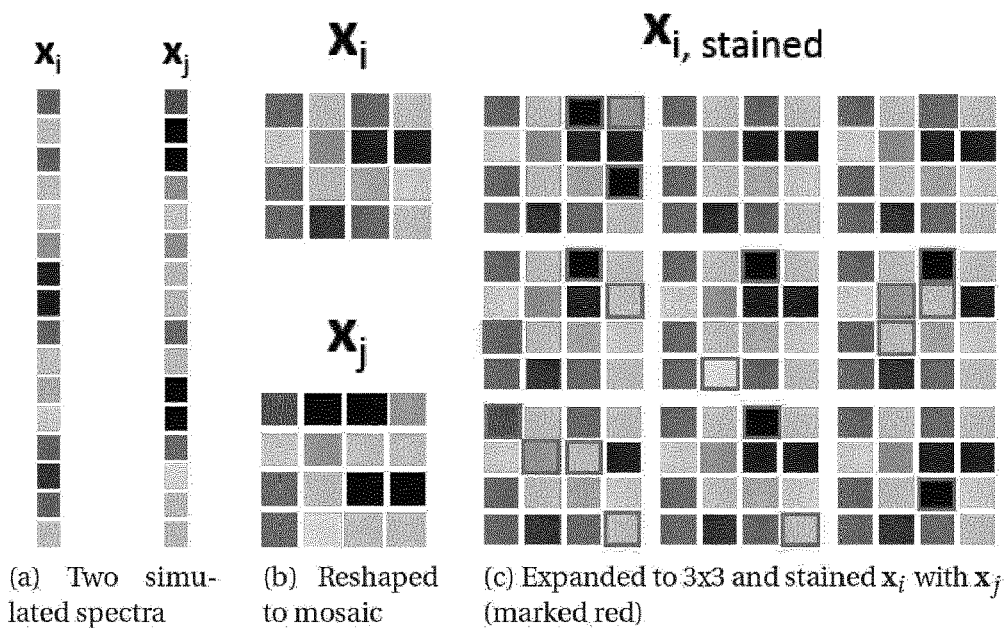
FIG. 6(a) shows a schematic representation of two simulated spectra.
FIG. 6(b) shows the two spectra of FIG. 6(a) reshaped to a mosaic.
FIG. 6(c) shows the mosaic of FIG. 6(b) expanded to 3×3, in which one simulated spectrum is stained with the other.
FIG. 6(d) shows a 4×4 mosaic and a corresponding evaluated neighborhood, to which the trained regressor is applied.
Figure 6D:
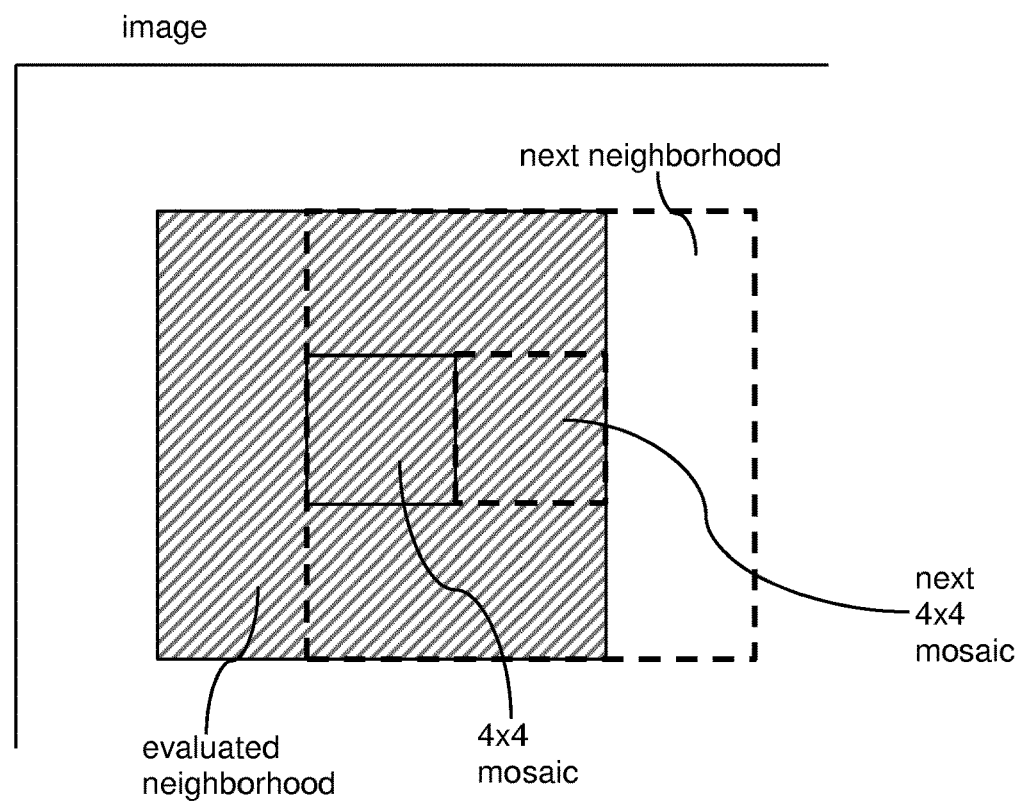
Figure 6E:
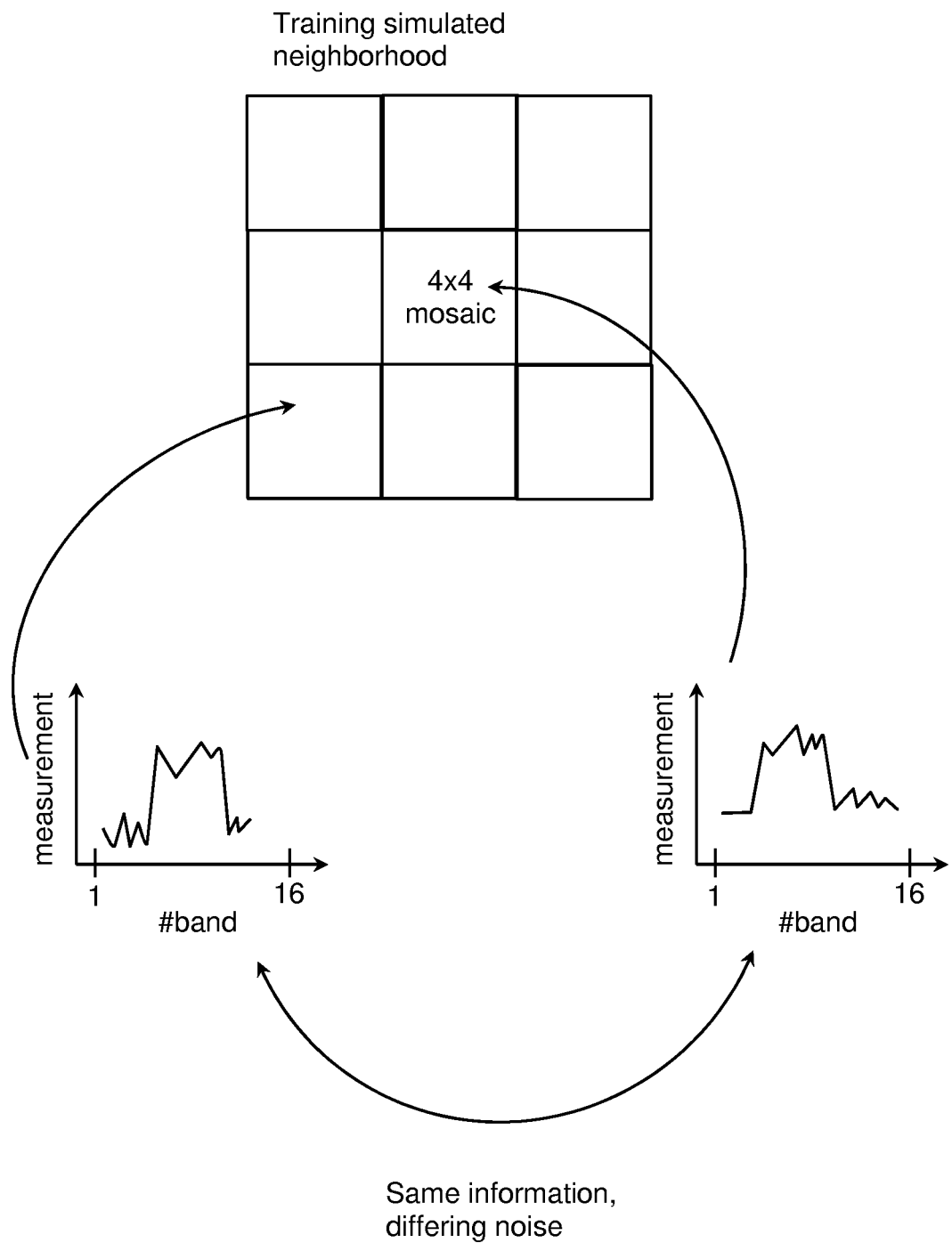

FIG. 6(e) illustratively shows how a neighborhood for training purposes is generated using the same information but different copies of a simulated spectrum for a 4×4 mosaic.

Figure 6F:
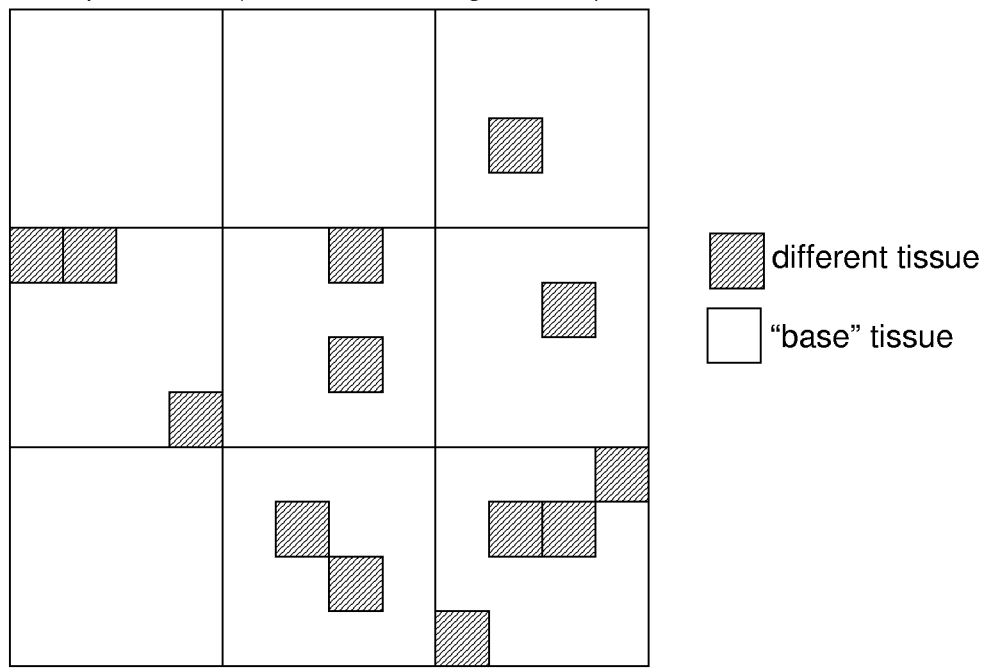
Figure 6F:
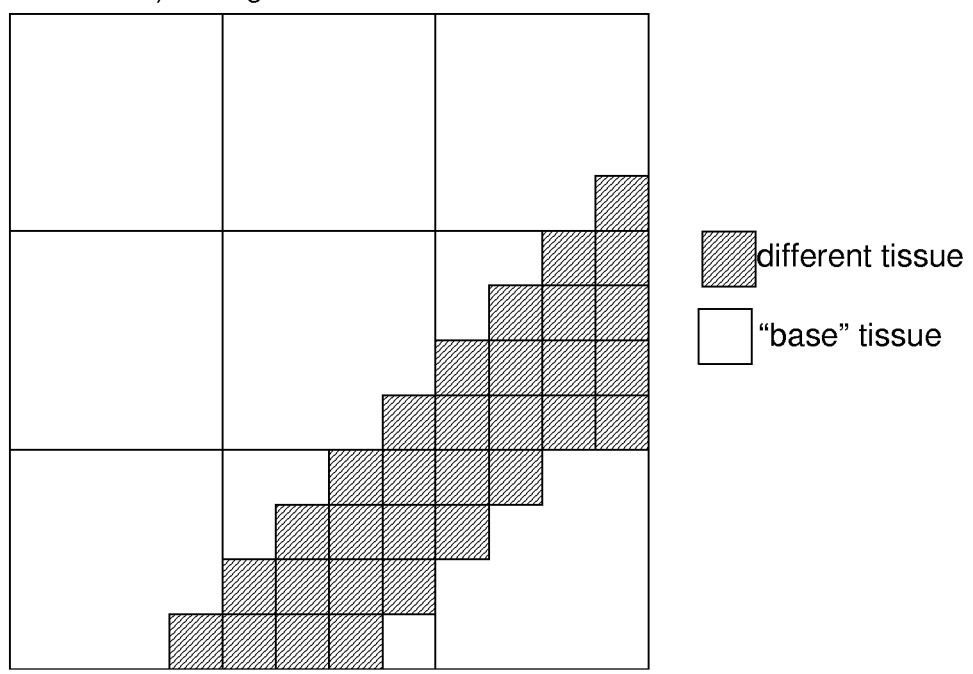

FIG. 6(f) shows two examples of neighborhoods for training purposes employing different models for tissue inhomogeneities (random inhomogeneities (top) and inhomogeneities due to a vessel (bottom)).

Figure 7:
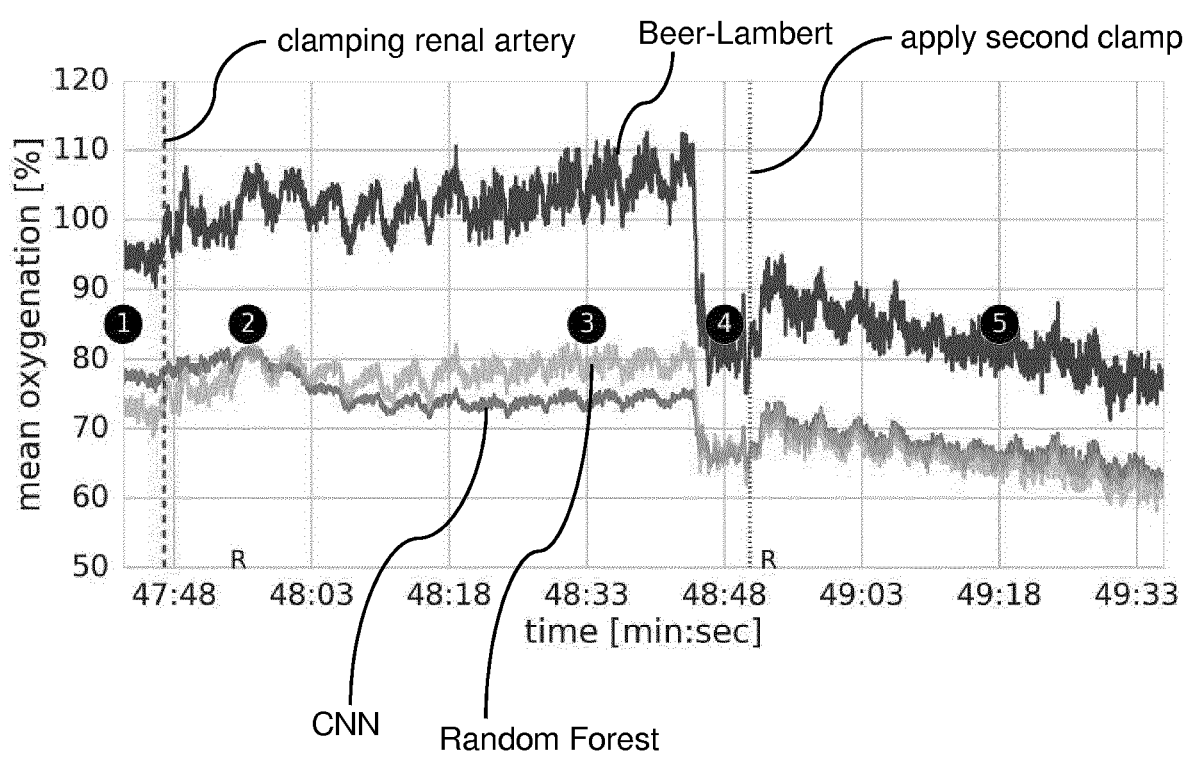

FIG. 7 shows mean oxygenation values obtained using a CNN regressor, a random forest regressor and the standard Beer-Lambert approach as a function of time.

Figure 8:
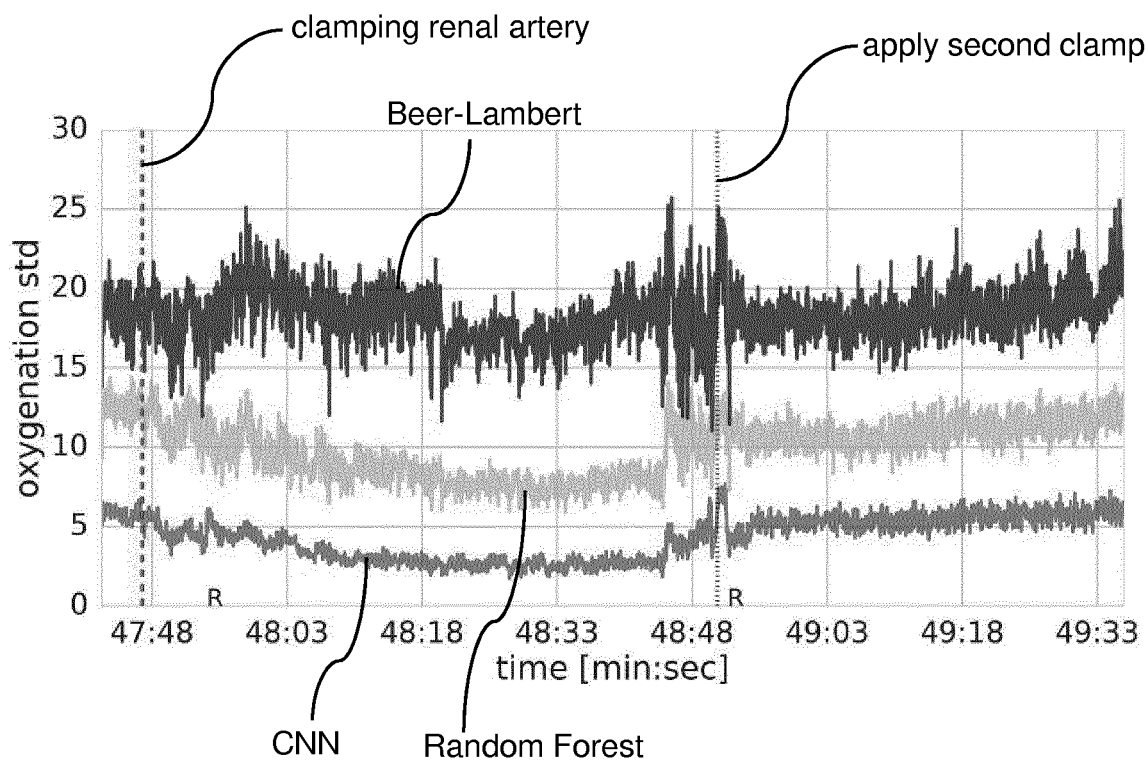

FIG. 8 shows the corresponding standard deviations of the oxygenation values shown in FIG. 7.

Figure 9:
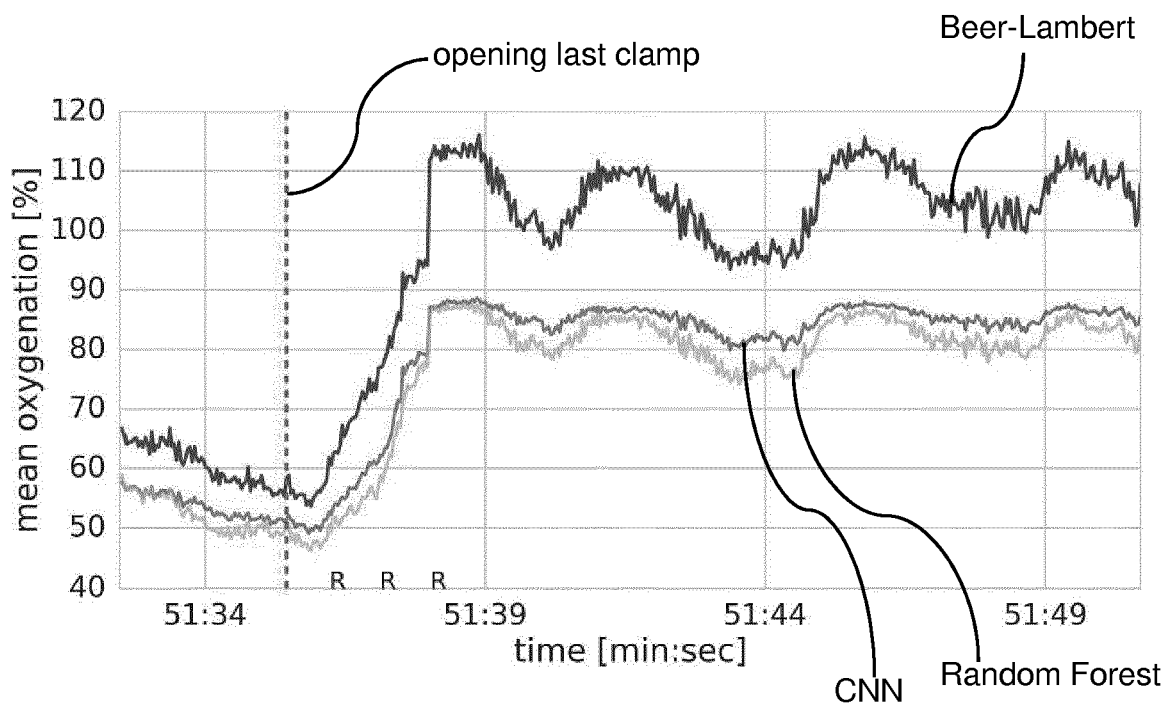

FIG. 9/10 show similar oxygenation values as FIGS. 7 and 8, but for a situation after the last clamp is open, leading to a recovery of oxygenation.

Figure 11:
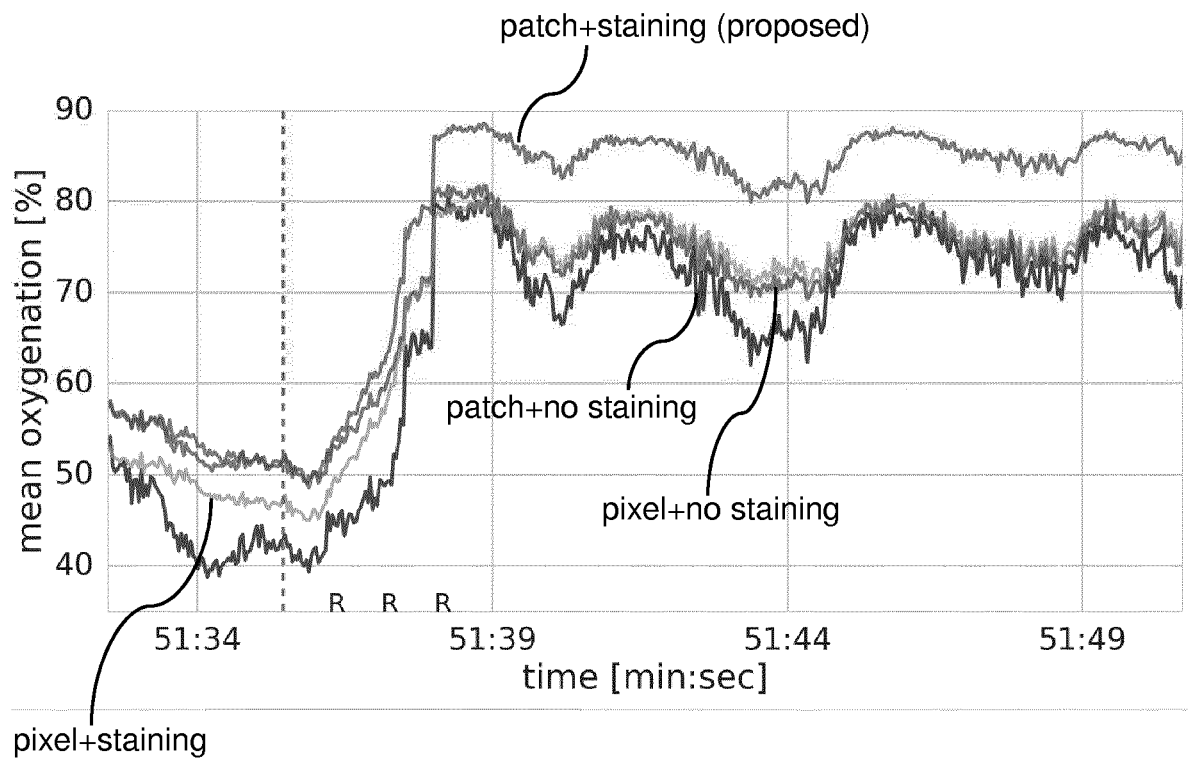

FIG. 11 shows mean oxygenation as a function of time determined with different training methods for a CNN.

Figure 12:
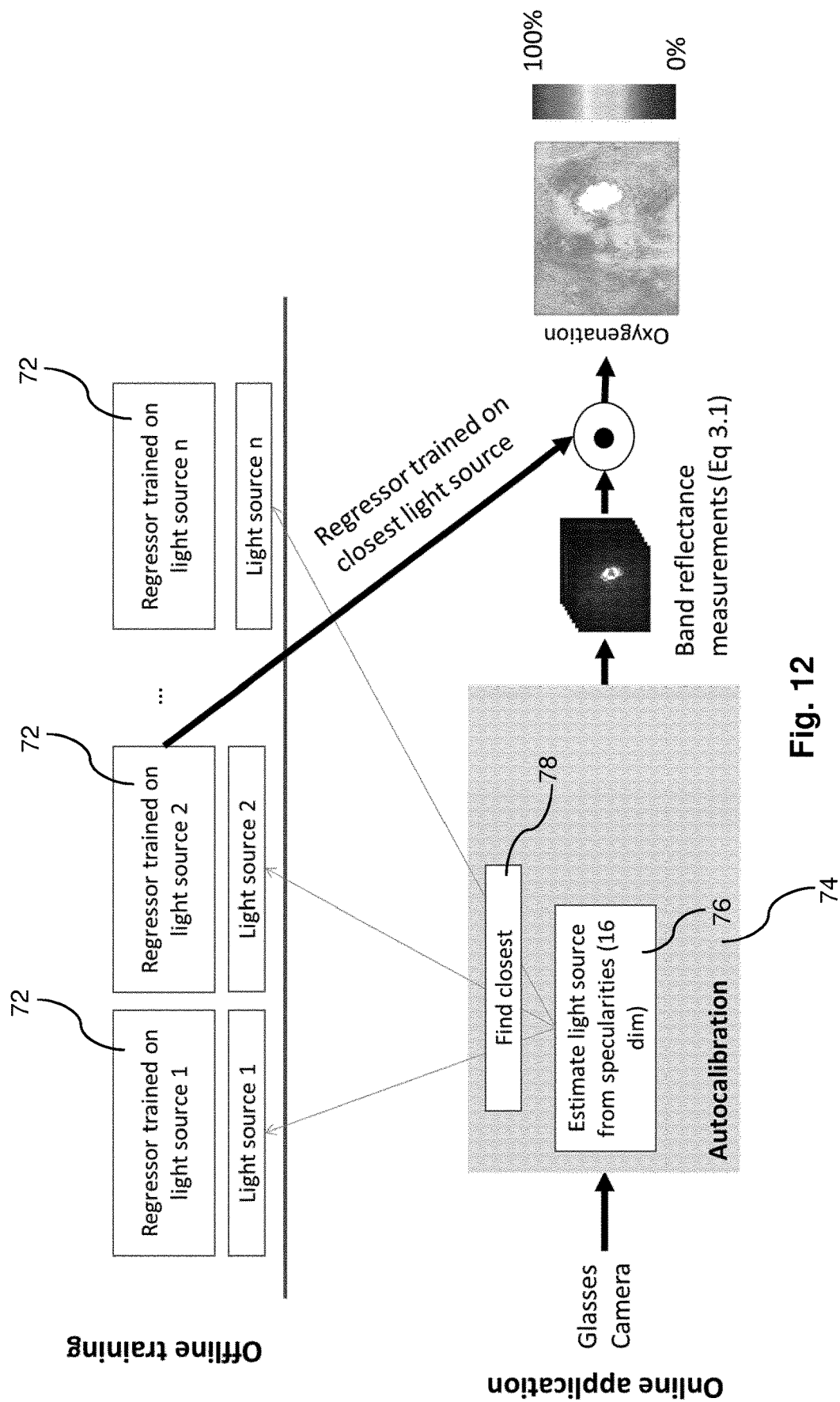

FIG. 12 is a schematic diagram illustrating a first variant of autocalibration of measured multispectral images.

Figure 13:
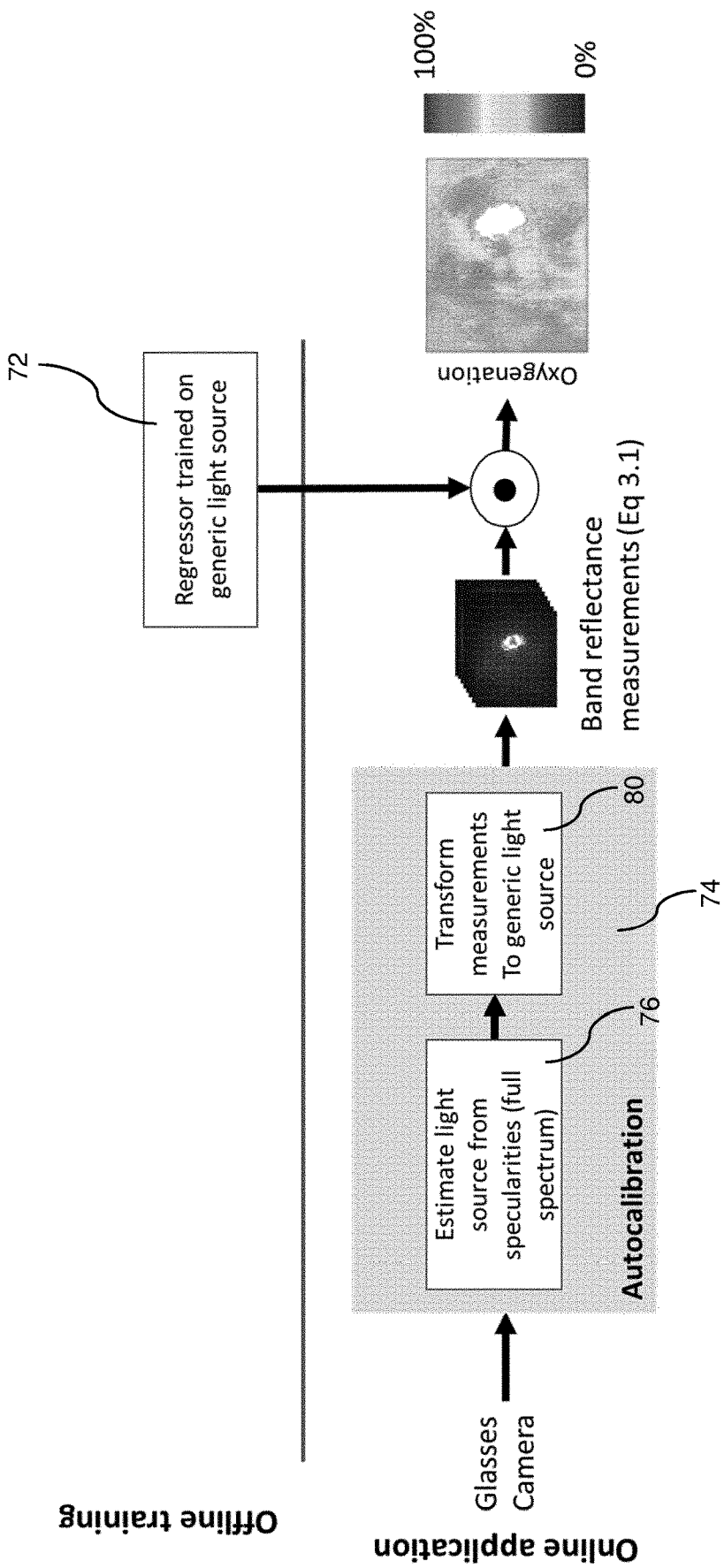

FIG. 13 is a schematic diagram illustrating a secondary variant of autocalibration of measured multispectral images.

Figure 14:
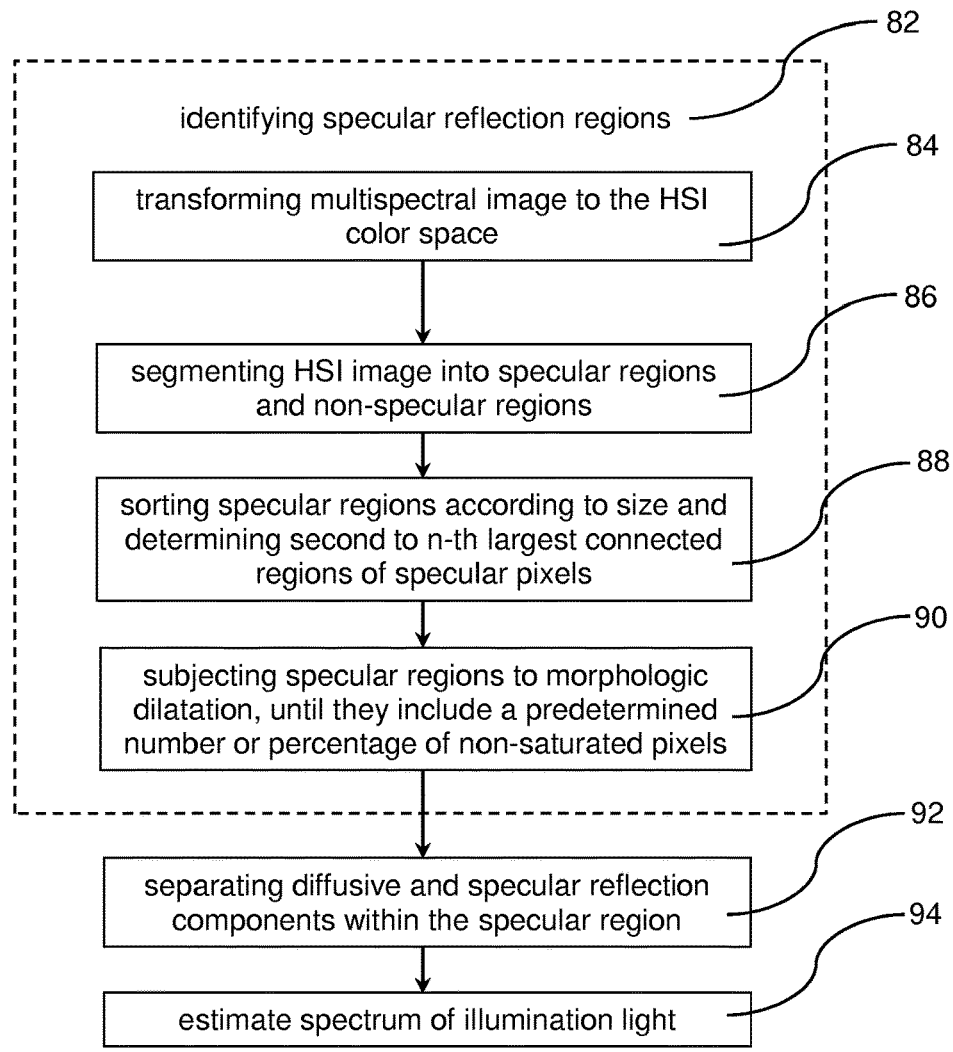

FIG. 14 is a flow diagram illustrating the estimation of the spectral composition of an illumination light source.

Figure 15:
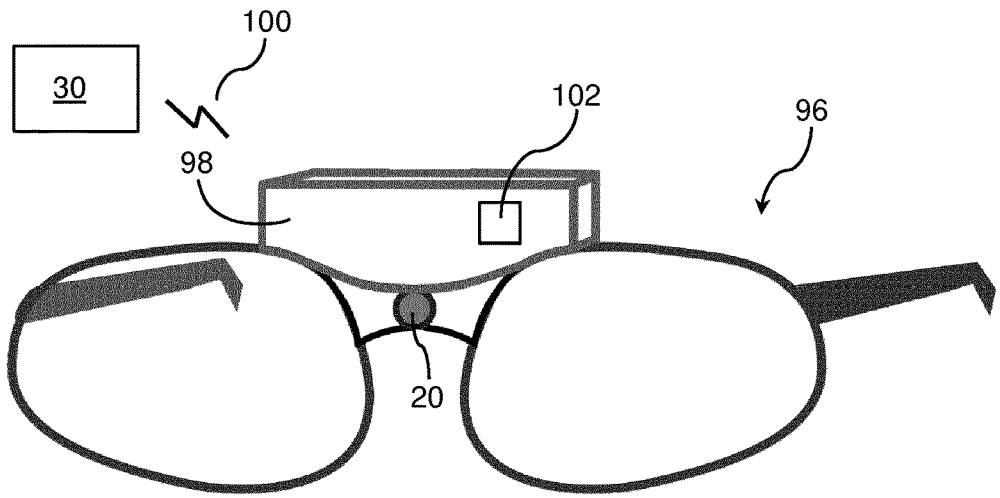

FIG. 15 schematically shows goggles for use in a MSI-based augmented imaging method according to an embodiment of the invention.

Figure 16:
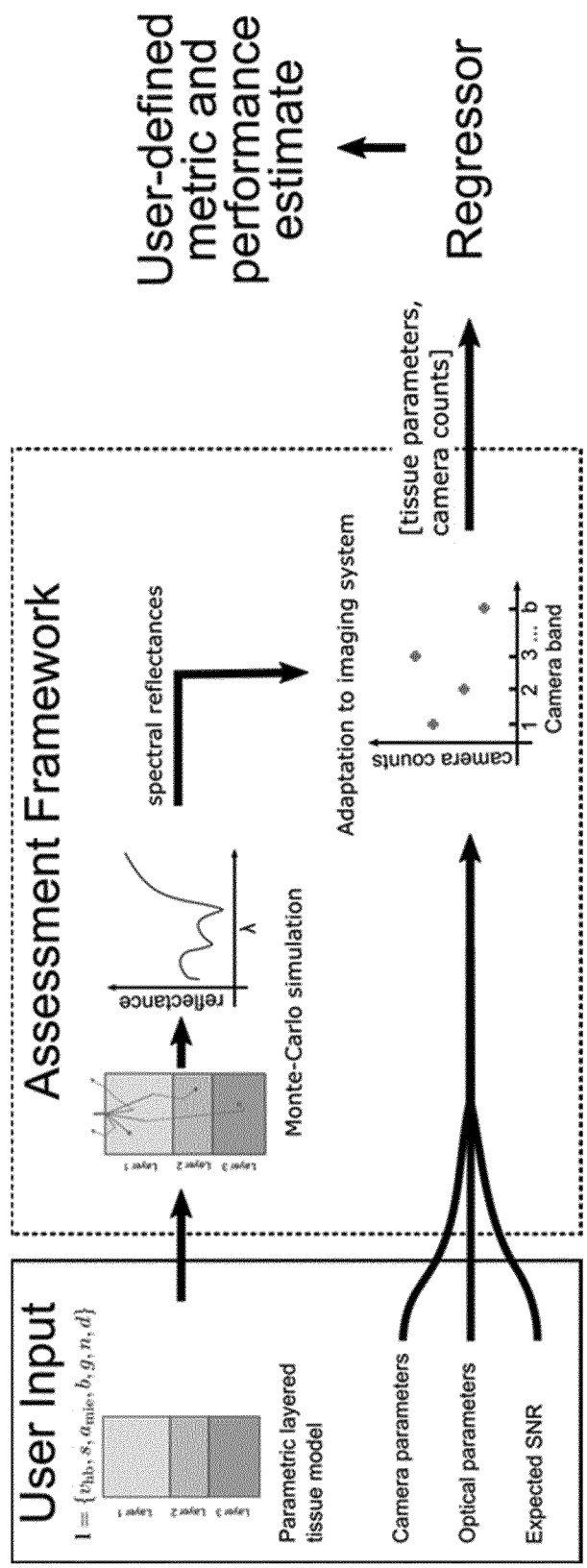

FIG. 16 schematically shows a simulation framework for characterizing performance of custom designed multispectral filter bands for medical applications.

Figure 17:
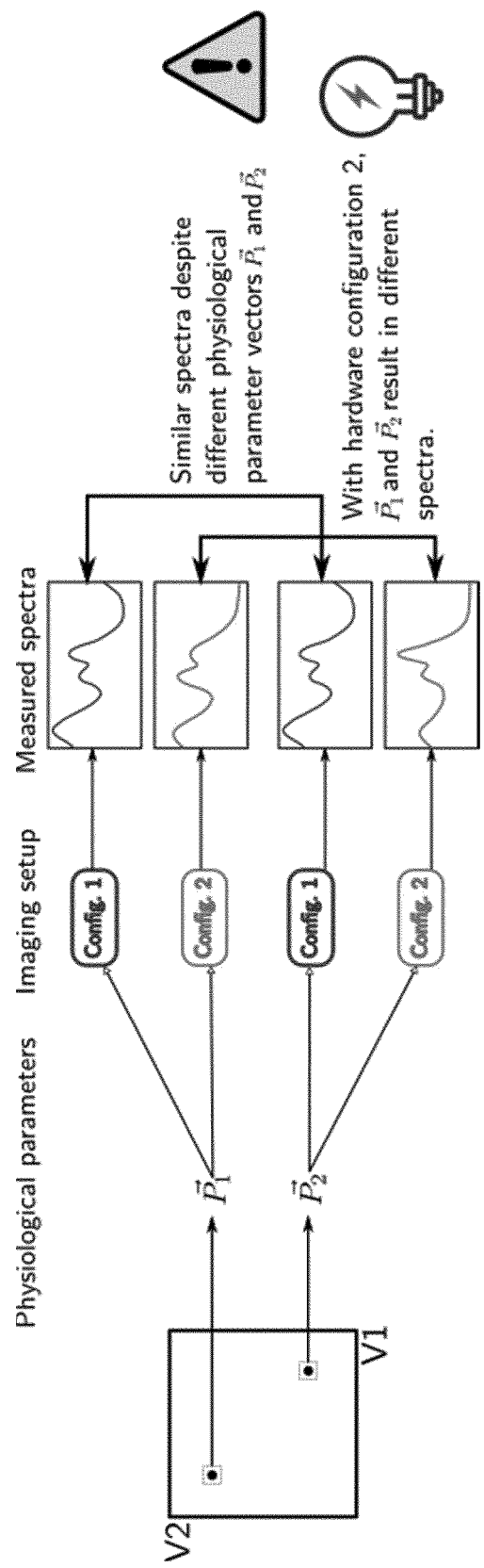

FIG. 17 illustrates a situation where different tissue parameters are found to yield almost identical spectra, when a first hardware configuration is used, and distinguishable spectra, when a second hardware configuration issues.

Figure 18:
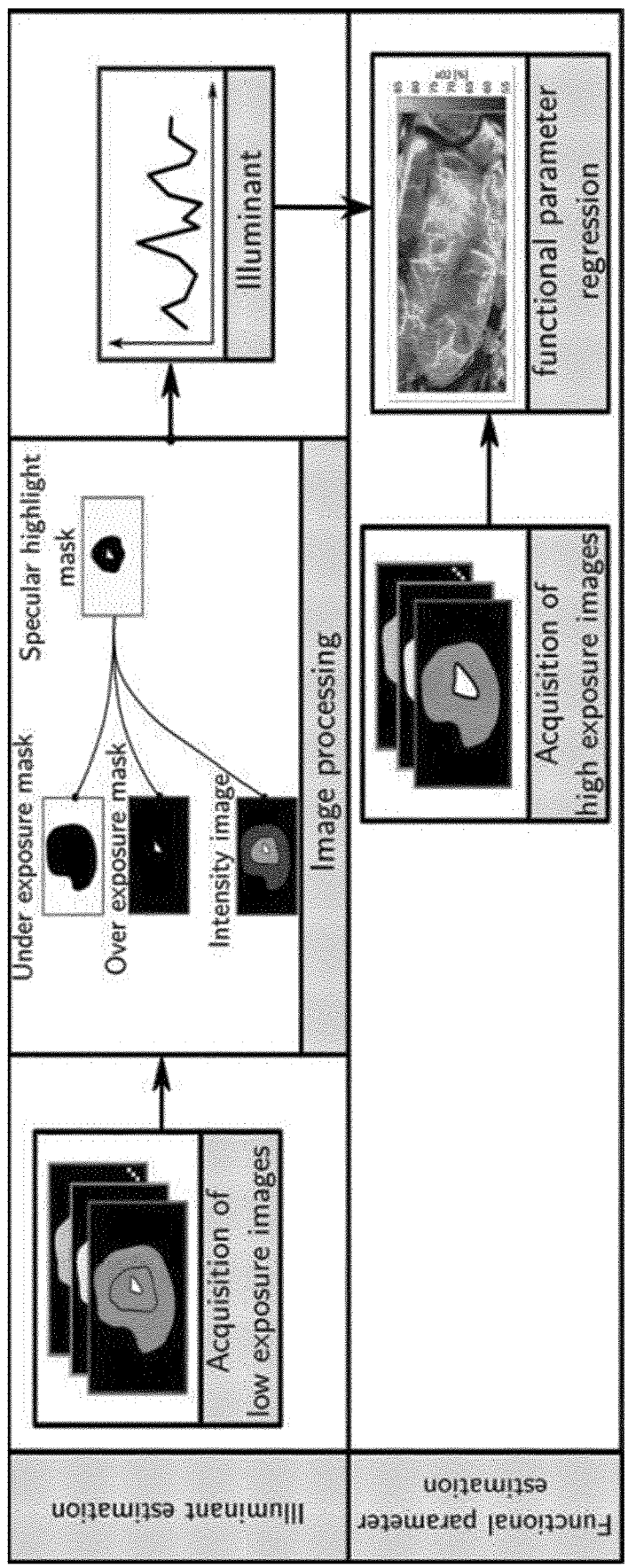

FIG. 18 is a diagram illustrating a process of estimating a spectral composition illuminating a region of interest based on low exposure images.

Figure 19:
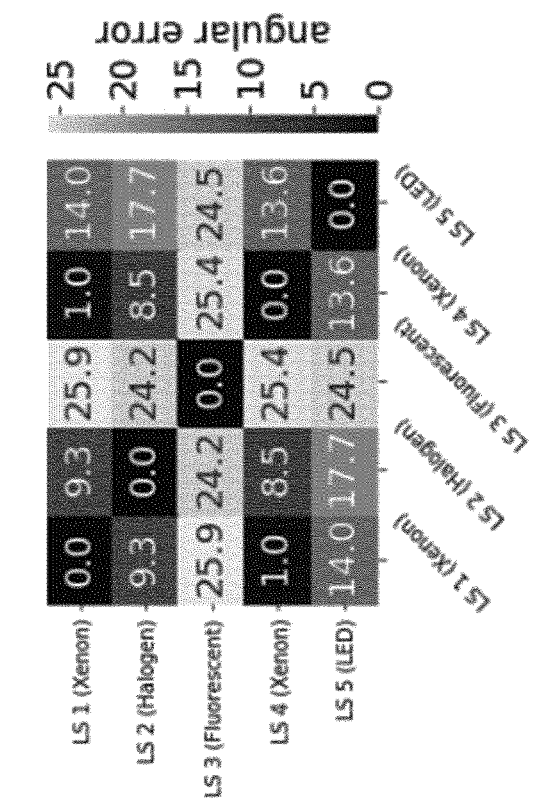
Figure 19:
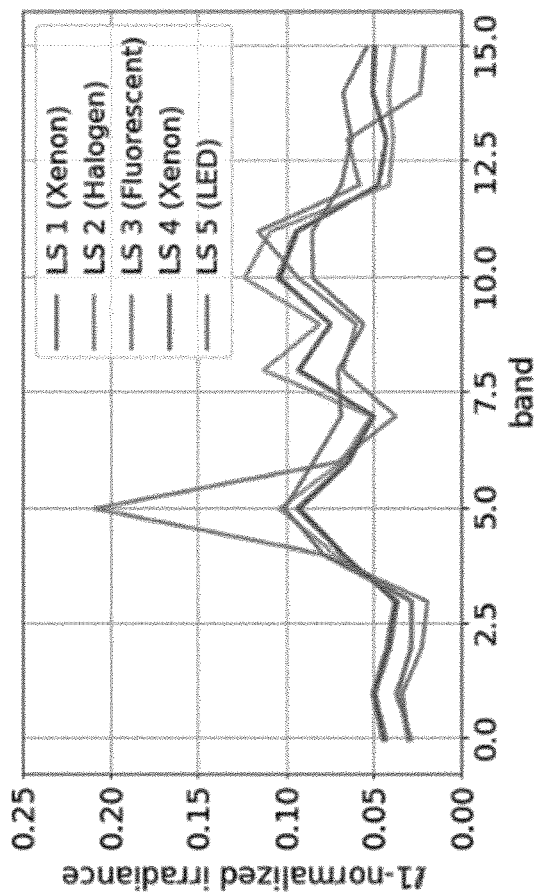

FIG. 19 shows the spectra of five exemplary light sources and their mutual angular distances in a confusion matrix.

Figure 20A:
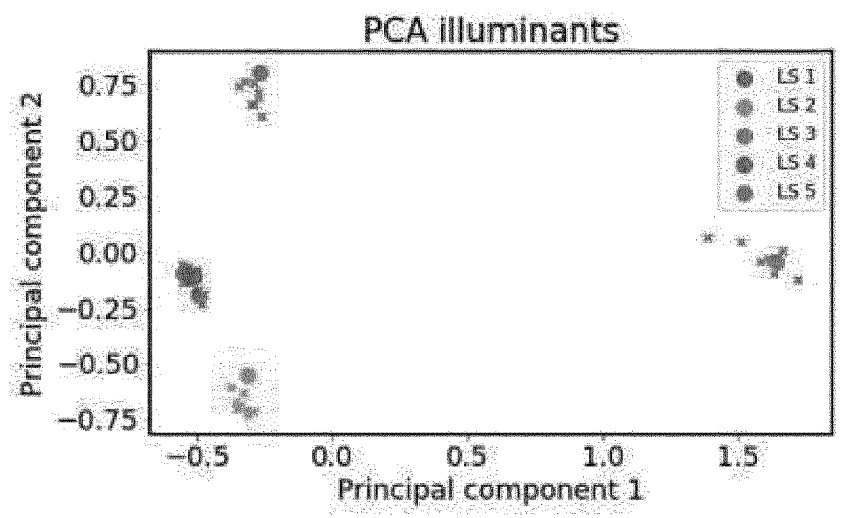

FIG. 20a shows reference illuminant spectra along with their estimations.

Figure 20B:
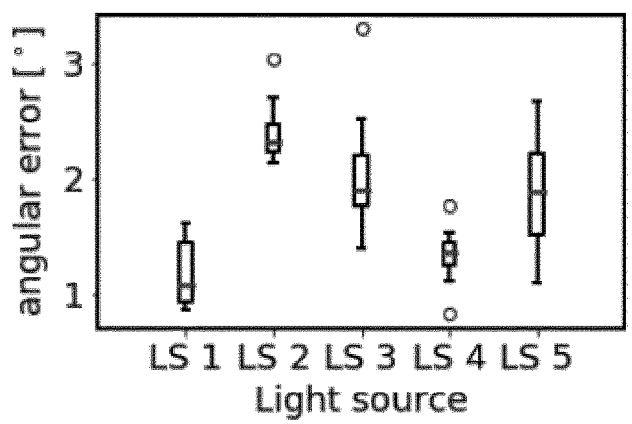

FIG. 20b is a diagram illustrating the performance of the illuminant estimation method according to an embodiment of the invention.

Figure 21A:
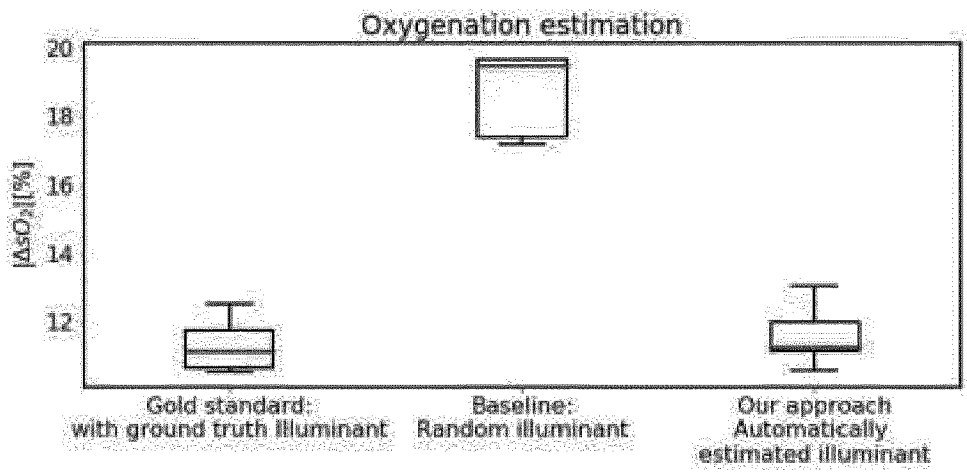

FIG. 21a is a diagram showing a mean error in oxygenation estimation when using the ground truth illuminant for training ranges, when using a random illuminant, and when using the illumination spectrum estimation according to an embodiment of the invention.

Figure 21B:
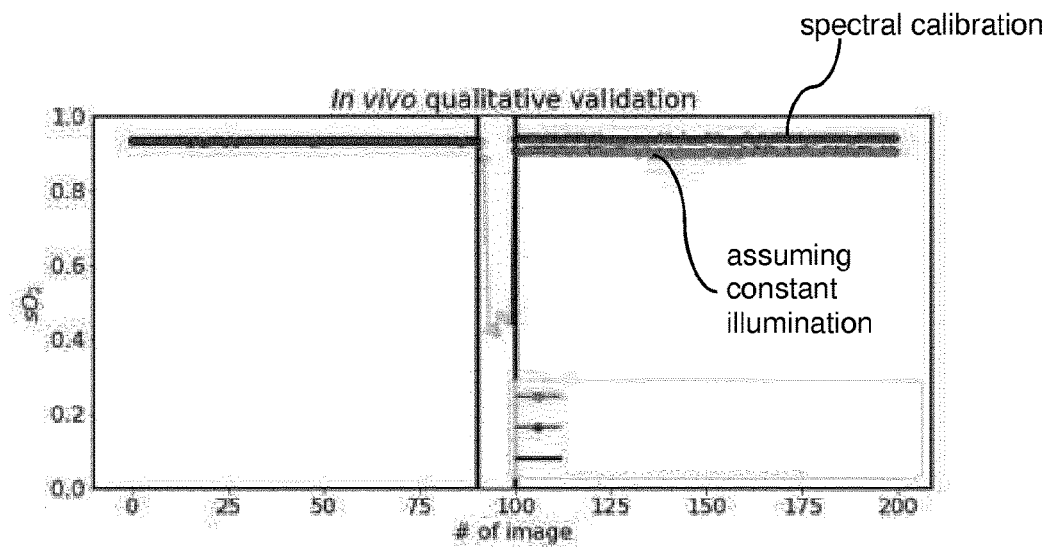

FIG. 21b shows the time of evolution of an oxygenation value when the illumination light source is exchanged, when using the corresponding spectra calibration as compared to the assumption of a constant illumination.

Figure 22:
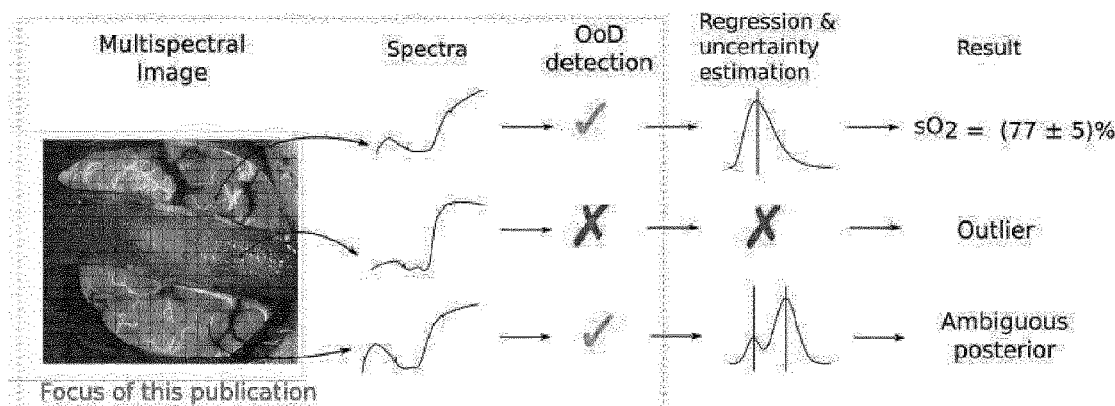

FIG. 22 is a diagram illustrating a multistage process for uncertainty handling including out of domain (OoD) detection.

Figure 23:
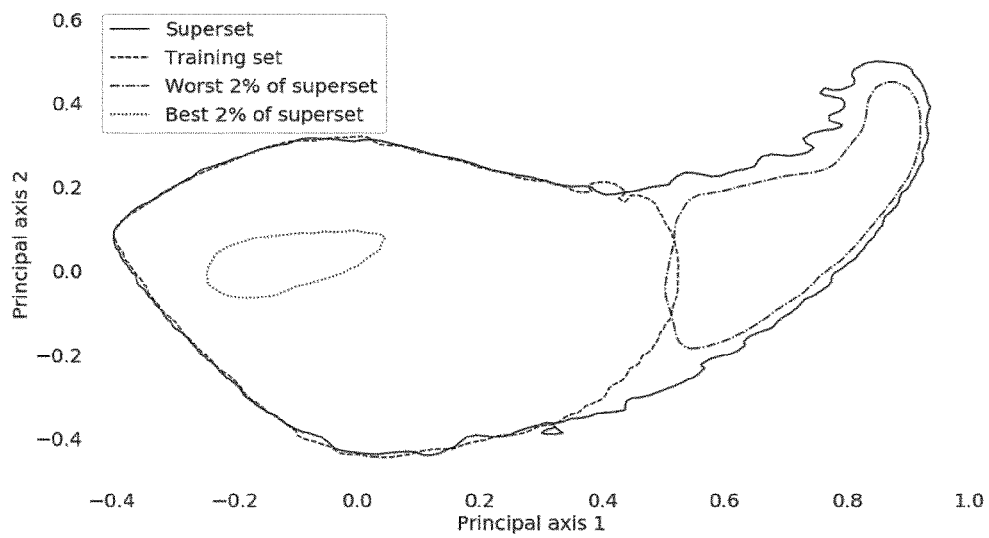

FIG. 23 FIG. 23 shows the results obtained with the WAIC method—trained on the small training set—when applied to a superset. The small training set is projected onto the first two principal components (PCA) of the complete training set and lies within the dashed contour. The 2% percentile of best superset spectra according the WAIC value lie within the dotted contour, and the 2% percentile worst spectra according to the WAIC-value lie within the chain dotted contour.

Figure 24:
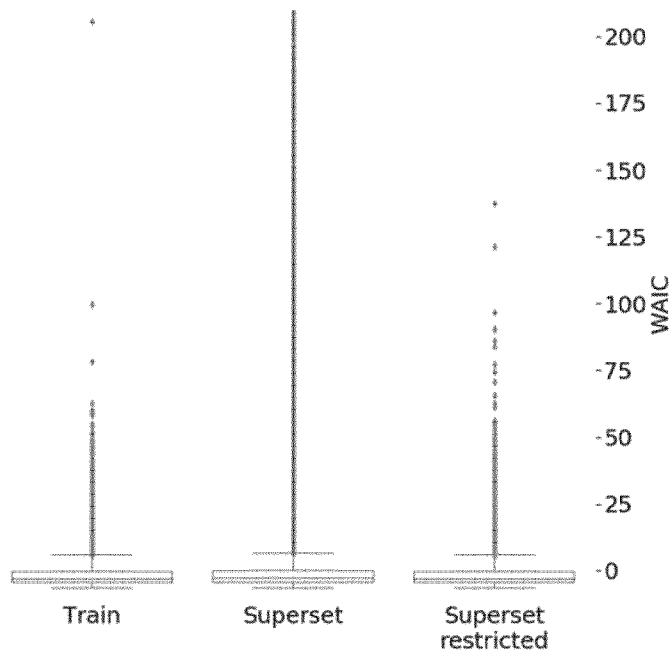

FIG. 24 shows box plots of WAIC-values obtained for training set, a superset and a restricted superset.

Figure 25:
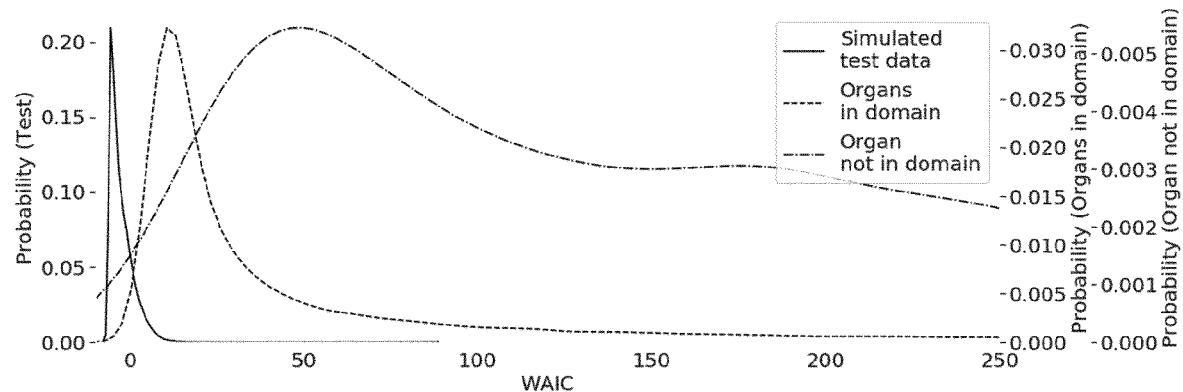

FIG. 25 shows the WAIC distribution for simulated test data, the in-domain-organs and an out-of-domain organ.

Figure 26:
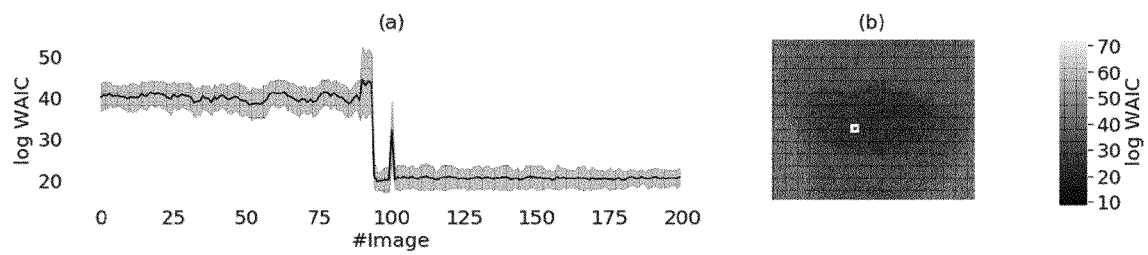

FIG. 26 shows a WAIC image image of the lip of a healthy human volunteer on the left and a corresponding WAIC time series for a region of interest is shown during which the light source is changed.

DESCRIPTION OF THE PREFERRED EMBODIMENTS

For the purposes of promoting an understanding of the principles of the invention, reference will now be made to a preferred embodiment illustrated in the drawings, and specific language will be used to describe the same. It will nevertheless be understood that no limitation of the scope of the invention is thereby intended, such alterations and further modifications in the illustrated apparatus and such further applications of the principles of the invention as illustrated therein being contemplated as would normally occur now or in the future to one skilled in the art to which the invention relates.

As was indicated above, multispectral imaging (MSI) has the potential to monitor intricate changes in tissue perfusion, which are quantified by blood volume fraction and oxygenation and cannot easily be seen by the human eye. Deciphering this information, i.e., estimating the molecular composition of tissue on the basis of multispectral images, remains challenging.

Figure 1:
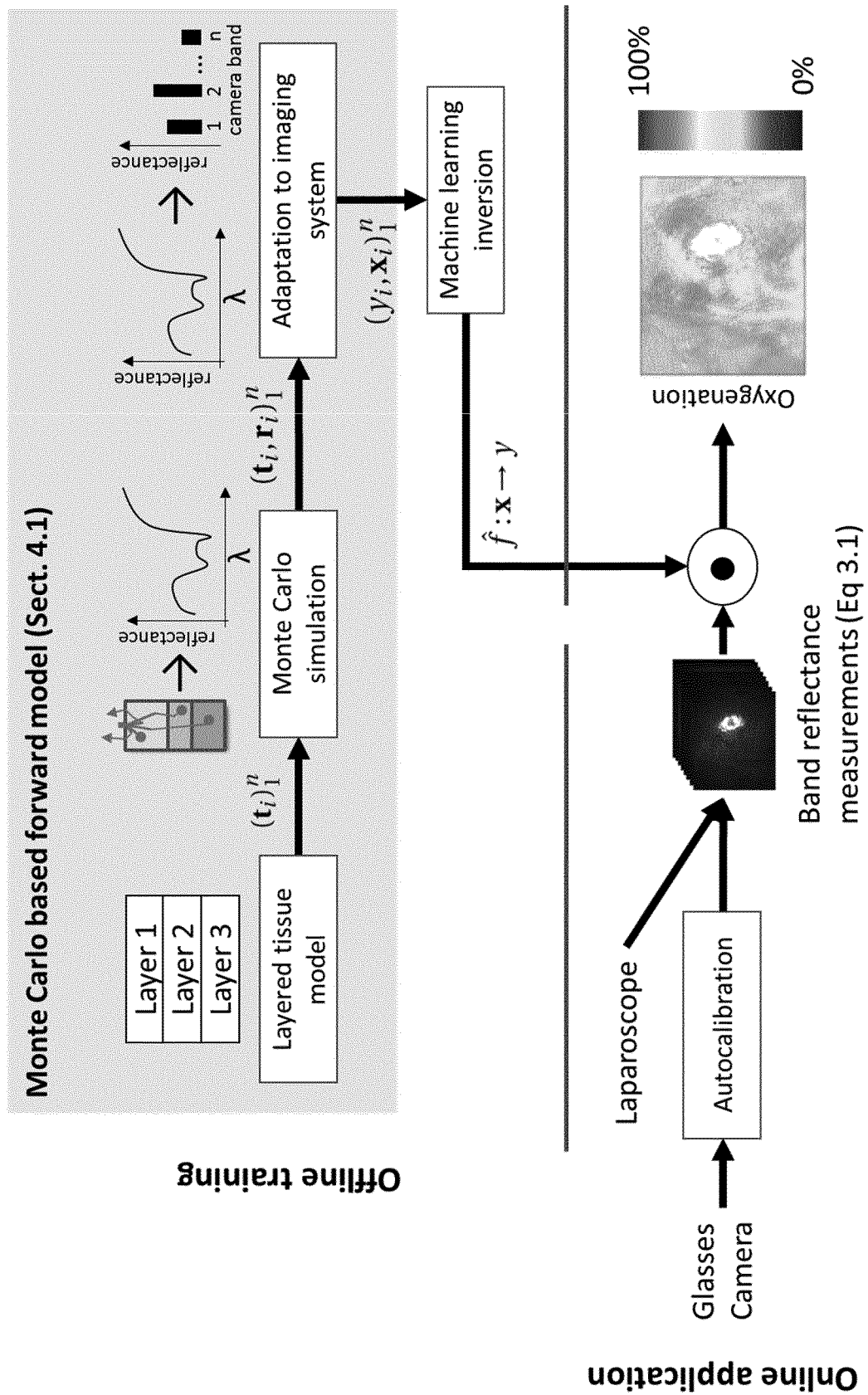
FIG. 1 is a schematic overview over a augmented imaging method according to an embodiment of the invention.

Embodiments of the invention are capable of video-rate estimation of physiological parameters during minimally invasive interventions as well as open surgery by combining the accuracy of Monte Carlo based approaches with the speed of state-of-the-art machine learning (ML) algorithms, as is schematically indicated in FIG. 1.

FIG. 1 gives a schematic overview over a augmented imaging method according to an embodiment of the present invention. As is seen from FIG. 1, the procedure comprises an "off-line" part, also referred to as "training part", which is carried out prior to the actual intervention during which augmented imaging is desired, and an "online part" in which the augmented imaging is carried out in real time. As seen from FIG. 1, in the offline phase, n examples $(t_i)^{n,1}$ are drawn from a point-wise model of artificial tissue to be described in more detail below. For each of these samples, highly accurate simulations calculate a spectral reflectance $r_i$. Herein, the index i denotes a voxel of the tissue that leads to a pixel in the image, and the bold font indicates that the reflectance $r_i$ is a vector, since it comprises as its components reflectance values for different wavelengths. Note that throughout this disclosure, vectors are indicated by bold font. In a next step, spectral reflectance $r_i$ is transformed to a space, which indicates the reflectance in each band that will be measured with the actual imaging system, i.e. the camera and the corresponding optics. The result of the learning is a regressor $\hat{f}$, which indicates the reflectance in each band that will be measured with the actual imaging system, i.e. the camera and the corresponding optics. Accordingly, this transformation is referred to as "adaption to imaging system" in FIG. 1 above. The band reflectances $x_i$ are then ready to serve as input for a machine learning algorithm. The algorithm learns how to relate the reflectance measurement of a pixel i to a functional tissue parameter $y_i \in t_i$, by establishing a corresponding regressor $\hat{f}$. This tissue parameter can e.g. be tissue oxygenation or blood volume fraction, but other function parameters are likewise possible, provided that they are represented by the tissue model.

In the online application, shown in the lower half of FIG. 1, the trained machine learning based regressor $\hat{f}$ is then applied to real multispectral images and within milliseconds generates an estimate $y_i$ for each (multispectral) pixel in the image. As is indicated in FIG. 1, these real multispectral images can be generated by cameras employed by different types of devices. One application would be a camera associated with a laparoscope. A second application considered herein relates to a camera that is installed in an operating room, for example associated with an operating room light device, and a third application relates to a camera associated with glasses or goggles to be worn by a surgeon. While in the laparoscope the illumination of the tissue is solely due to the illumination light source of the laparoscope itself, which has a precisely known spectral composition, in open surgery applications, where the other two applications would typically find use, one would usually have to deal with uncontrolled and varying illumination conditions. Various ways to cope with this situation are summarized under "auto calibration" in FIG. 1 and will be described in more detail below. From the multispectral images, true band reflectance measurements are derived, to which then the off-line trained regressor $\hat{f}$ is applied, to derive the tissue parameters $y_i$ (in the example of FIG. 1 "oxygenation") of the tissue encoded in the reflectance measurements. Since the functional parameters $y_i$ are associated with corresponding image pixels i, they can be displayed on a suitable display device as an image, as is shown in the lower right of FIG. 1 for the case of oxygenation. For laparoscopic applications, the display could be the same display on which the ordinary RGB images are displayed, and the augmented images could be additionally presented, next to the RGB image, or in an overlaid fashion. However, the augmented images or the information contained therein could also be presented in a chart or the like, for example a chart showing the oxygenation over time for a given region of interest. That is to say, the term "augmented image" implies that there is a tissue parameter associated with a certain region or pixel of an image of the tissue of interest, but it does not necessarily mean that it is represented to the user as an image.

For applications in open surgery, the display could be a display provided in the operating room, or the lenses of goggles to be worn by a surgeon into which functional information or any other type of additional information can be projected as per se known from augmented reality or so-called mixed reality applications.

As is apparent from the above, the input to the machine learning regression in the shown example is generated by a "forward model" that consists of three parts: (1) a layered tissue model that formally describes the composition of possible tissues, (2) highly realistic simulations of spectral reflectances that are computed using tissues drawn from the model, and (3) a transformation of the simulation to the camera space, which is referred to as "adaption to imaging system" in FIG. 1. This process of sample creation and transformation is represented by the box in the offline training part of FIG. 1. The term "forward model" indicates that the model follows the forward direction of causality. Namely, starting out from a model of the tissue, the interaction of light with the tissue is simulated, to obtain the reflectance of the tissue. In the preferred embodiment, this simulation is carried out by the Monte Carlo method. Herein, the tissue exhibits certain tissue parameters of interest, such as oxygenation, which will have an influence on its reflectance spectrum. Next, the reflectance of the tissue is adapted to the imaging system to predict the reflectivity image for each frequency band or color channel at each pixel of the multispectral camera under the specific optical setup that is to be used in operation. What needs to be solved in practice, however, is the reverse problem: For augmented imaging, the task is to determine, from the multispectral image, the relevant information of interest concerning the tissue, i.e its tissue parameters. This inverse problem is solved by the machine learning regressor $\hat{f}$ that is trained with the data obtained by the forward model. Both, the details of preferred embodiments of forward models and of the machine learning will be described in more detail in the following sections.

Layered Tissue Model

In embodiments of the invention, the tissue t inspected during surgery is modeled as a layered structure. Each layer l is characterized by a set of optically relevant tissue properties: $l=\{v_{hb}, s, a_{mie}, b, g, n, d\}$, where the parameters describe the following:

$v_{hb}$ blood volume fraction [%], the amount of blood occupying a unit volume of tissue s the ratio [%] of oxygen-bound hemoglobin to total hemoglobin, also referred to as oxygenation $a_{mie}$ a parameter quantifying the amount of scattering [cm$^{-1}$] by the reduced scattering coefficient at a given wavelength, here at 500 nm b the scattering power, a term which characterizes the exponential wavelength dependence of the scattering g an anisotropy factor, characterizing the directionality of scattering n the refractive index d the layer thickness [μm]

The optical and physiological parameters $a_{mie}$, b, g, $v_{hb}$ and s influence the optical absorption and scattering coefficients. As in D. Hidovic-Rowe and E. Claridge. *Modelling and validation of spectral reflectance for the colon. PhysMed Biol,* 50(6):1071-1093 (2005), the absorption coefficient $\mu_a$ at wavelength λ may be calculated by $$\mu_a(w_{hb},s,\lambda)=v_{hb}c_{hb}(s\cdot\epsilon_{HbO2}(\lambda)+(1-s)\cdot\epsilon_{Hb}(\lambda))\ln(10) \\ (64,500 \text{ g mol}^{-1})^{-1}. \tag{1}$$

$\epsilon_{HbO2}$ and $\epsilon_{Hb}$ are the molar extinction coefficients of oxygenated and de-oxygenated hemoglobin and $c_{hb}$ is the molar concentration of hemoglobin in human blood. Herein, hemoglobin, the oxygen transporter in human blood, can be assumed to be the only notable absorber at least for visceral applications. Another notable absorber of visible light in human tissue is melamine, which however is mainly contained in the skin. Clearly, the model allows for easy integration of further absorbers (if necessary) by modifying the above equation (1). In this model, oxygenation is assumed to be constant across layers, which is a reasonable assumption if the layers share a common blood supply. The reduced scattering coefficient $\mu_s'$ is calculated by an empirical power law $$\mu_s'(a_{mie}, b, \lambda) = a_{mie}\left(\frac{\lambda}{500 \text{ nm}}\right)^{-b}. \tag{2}$$

This simple heuristic approximation to measurements of reduced scattering was proposed in S. L. Jacques. *Optical properties of biological tissues: a review. Physics in Medicine and Biology,* 58(11):R37-R61 (2013) for the visible wavelength range. The anisotropy factor g is assumed constant over the wavelength range. With g and $\mu_s'$, the scattering coefficient $\mu_s$ can be calculated by $$\mu_s(a_{mie}, b, \lambda) = \frac{\mu_s'(a_{mie}, b, \lambda)}{1-g}.$$

Pixel independence is implicitly assumed, by modelling tissue as homogeneous, infinite slabs. This leads to less assumptions on the 3D composition of tissue as e.g. vessels, but prevents modelling cross-talk between pixels.

Calculation of Spectral Reflectance

The spectral reflectance denotes the portion of light returning to the surface after interaction with the tissue for each wavelength. This quantity is a property of the tissue and as such independent on the measurement system. To generate such a reflectance spectrum r from a tissue drawn from the layered model, a function $r_{sim}$ is evaluated at wavelengths λ

$$r(\lambda,t)=r_{sim}(\lambda,t)=r_{sim}(\lambda,l_1,\ldots,l_k). \quad (3)$$

In this embodiment, a multi-layered MC (MCML) approach can be chosen for evaluation of $r_{sim}$, because MC models are widely considered to be the gold standard for calculating how light travels through biological tissue. The MC tissue optics simulation irradiates multi-layered tissue with photon packets as disclosed in L. Wang and S. L. Jacques. *Monte Carlo modeling of light transport in multi-layered tissues in standard C.* The University of Texas, MDAnderson Cancer Center, Houston (1992). Depending on the properties of the layers, the photons will be probabilistically reflected, scattered and absorbed. Among other attributes, the photons reflected at the tissue surface due to (possibly multiple) scattering events can then be determined in the simulation.

Adaptation to Imaging System

The simulations described in the previous paragraph yield spectral reflectances at specific wavelengths. The spectral reflectance is an inherent property of the tissue and as such independent on the measurement system and lighting. As a third step in the generation of the forward model, as shown in FIG. 1 ("adapting to imaging system"), the camera independent spectral reflectances are converted to values proportional to image intensities measured by the specific camera that will be used during the intervention in the online application. As indicated in FIG. 1, the camera can e.g. be associated with a laparoscope, a camera installed or movably provided in an operating room, or a camera associated with glasses worn by a surgeon, in particular glasses adapted for augmented reality applications, as will be described in more detail below. The invention is not limited to any specific type of camera. However, in preferred embodiments of the invention, the specific camera to be used in online application is explicitly accounted for in establishing the forward model used for training the machine learning regressor, by what is referred to herein as "adapting to imaging system" in FIG. 1. In the embodiment considered here, the camera comprises a multispectral sensor which integrates the reflectance over the spectral bands $b_j \in b$, where j is an integer number indicating the respective band, and b is a vector formed by the individual bands. The camera intensity measurement $i_j$ for the j-th band is assumed to be dependent on the following factors:

- r(λ,t) the spectral reflectance for the tissue.
- $l_j(\lambda,p)$ linear factors subsuming the response of $b_j$, the quantum efficiency of the camera, the irradiance of the illuminant (e.g., Xenon or Halogen) and other components in the imaging system like the transmittance of the optic set used. It will generally be dependent on the position in the image p.
- τ(•) the camera response function, which is often intentionally non-linear to cover a higher range of irradiances within the possible image intensities
- $\omega_j$ camera noise for band j, which is mainly formed by shot noise due to the particle nature of light and so-called dark noise, which is dependent on sensor temperature and linear in integration time For large image intensities, the typically Poisson distributed noise sources can be approximated by multiplicative Gaussian noise (see G. E. Healey and R. Kondepudy. *Radiometric CCD camera calibration and noise estimation. Pattern Analysis and Machine Intelligence, IEEE Transactions on,* 16(3):267-276 (1994), J. Katrarnik, F. Pernur, and B. Likar. *Radiometric calibration and noise estimation of acousto-optic tunable filter hyperspectral imaging systems. AppliedOptics,* 52(15):3526-3537 (2013) and A. Mansouri, F. S. Marzani, and P. Gouton. *Development of a protocol for CCD calibration: application to a multispectral imaging system. International Journal of Robotics and Automation,* 20(2):94-100 (2005)). Because the analysis is carried out on pixel level, geometric distortions caused by lens effects are not relevant. Based on the above ingredients, an image intensity can be simulated by $$i_j(t)=\tau(\int_{\lambda_{min}}^{\lambda_{max}}l_j(\lambda,p)\cdot r(\lambda,t)\cdot \omega_j d\lambda). \quad (4)$$

Assuming τ(•) is linear and that the spatial inhomogeneities of the light source are independent of wavelength $l_j(\lambda,p)=\alpha(p) l_j(\lambda)$, the model simplifies to $$i_j(t)=\alpha(p)\int_{\lambda_{min}}^{\lambda_{max}}l_j(\lambda)\cdot r(\lambda,t)\cdot \omega_j d\lambda \quad (5)$$

The factor α(p) accounts for constant multiplicative changes in intensity, which can be regarded as an "overall brightness". The reason for these changes are differences in distance or angle of the camera to the tissue and the internal scaling of electrical current to values measured by a camera, as further described in E. Claridge and D. Hidovic-Rowe. *Model based inversion for deriving maps of histological parameters characteristic of cancer from ex-vivomultispectral images of the colon. IEEE TransMed Imaging* (2013).

Machine Learning Based Inversion With the method described so far, simulated image intensities depend on the image brightness α(p) and the spectral distribution of light reaching the sensor $l_j(\lambda)$. To make the data more robust to changes in $l_j(\lambda)$, each band intensity may be divided by its volume $1_j=\int_{\lambda_{min}}^{\lambda_{max}} l_j(\lambda)\, d\lambda$. The results is referred to as "band reflectance" herein:

$$r_j(t) = \frac{i_j(t)}{1_j} = a(p)\cdot \int_{\lambda_{min}}^{\lambda_{max}} \frac{l_j(\lambda)}{\int_{\lambda_{min}}^{\lambda_{max}} l_j(\lambda)d\lambda} \cdot r(\lambda, t)\cdot w_j d\lambda. \quad (6)$$

This corresponds to a calibration with a white target as one would do for real measurements. The multiplicative α(p) is accounted for by normalizing with the sum of all bands, transforming the data to what is further referred to as normalized reflectance:

$$r_{j,n}(t) = \frac{\alpha(p)r_j(t)}{a(p)\Sigma_k r_k(t)} = \frac{r_j(t)}{\Sigma_k r_k(t)}. \quad (7)$$

This way, dependence on α(p) is removed. As a final transformation −log is taken from the normalized reflectance s and the resulting values are divided by their $\ell^2$ norm, transforming the data to what is called normalized absorbance $x_j$:

$$x_j(t) = \frac{-\log r_{j,n}(t)}{\sqrt{\Sigma_k(-\log(r_{k,n}(t)))^2}}. \quad (8)$$

This last transformation is strictly speaking not necessary, but is found to lead to better experimental results in regression. Given a noise model W and a tissue t, the training input data for the regressor $X=(x(t_1), \ldots, x(t_m))^T$ can be simulated.

Any machine learning regressor can be trained for specific tissue parameters y∈t, such as oxygenation and blood volume fraction. A machine learning regressor is a function $f_\Theta$, parametrized by parameters Θ. It maps input features, in this case the described x, to labels y, in this case tissue parameters. Machine learning methods generally aim to find the parameters which minimize the expected risk R:

$$\hat{f} = \underset{f_\theta}{\mathrm{argmin}}\, R(f_\theta, X_{train}, y_{train}, l(\cdot, \cdot)) = \frac{1}{|X_{train}|} \sum l(f_\theta(x_{train}), y_{train}) \quad (9)$$

Machine learning hence tries to determine the function which maps the training features $X_{train}$ closest to the training labels $y_{train}$. The notion of closeness is provided by the real valued loss 1, which is often amended by a regularizing term to prevent overfitting to the training data. The functions, often also called hypotheses, and minimization technique may differ substantially depending on method.

In the example of random regression forests, which may be employed in one embodiment, the functions are defined by an ensemble of decision trees. The path a feature traverses in a tree depends on comparisons taking place in the nodes. The output of the function is calculated from the leafs the feature landed in. Because the determination of the optimal trees is NP-complete (where NP stands for nondeterministic polynomial time), learning the trees is usually done by a greedy algorithm, which iteratively adds nodes, as further described in L. Breiman. *Random Forests. Machine Learning*, 45(1):5-32 (2001). For a more detailed description of machine learning, reference is made to M. Mohri et al. *Foundations of Machine Learning. The MIT press* (2012). ISBN 978-0-262-01825-8.

Random forest regressors were chosen in this embodiment because they are capable of near real-time regression of megapixel multispectral images. A further advantage is that random forest regressors are inherently multi-variate and thus allow joint oxygenation and blood volume fraction estimation. However, as will be demonstrated below, neural networks are likewise suited for the task, and advantageous in some respects.

Application to In Vivo Recordings

The trained regressor can be applied to each pixel of an in vivo acquired multispectral image, as indicated in the schematic representation of FIG. 1. This image should undergo the same transformations as the simulations. In the preferred embodiment, first the images I are transformed to normalized reflectance by correcting by a dark D and white image W:

$$X_I = \frac{I - D}{W - D}$$

and dividing by the mean in the spectral dimension. Similar to the transformations to the simulations in Equation (8), the actual multispectral measurement data is further transformed to absorbance and normalized by an additional $\ell^2$ norm. This ensures that real recordings and simulations are in the same space, which is independent of multiplicative changes in illumination.

Video Rate Analysis

Figure 2:
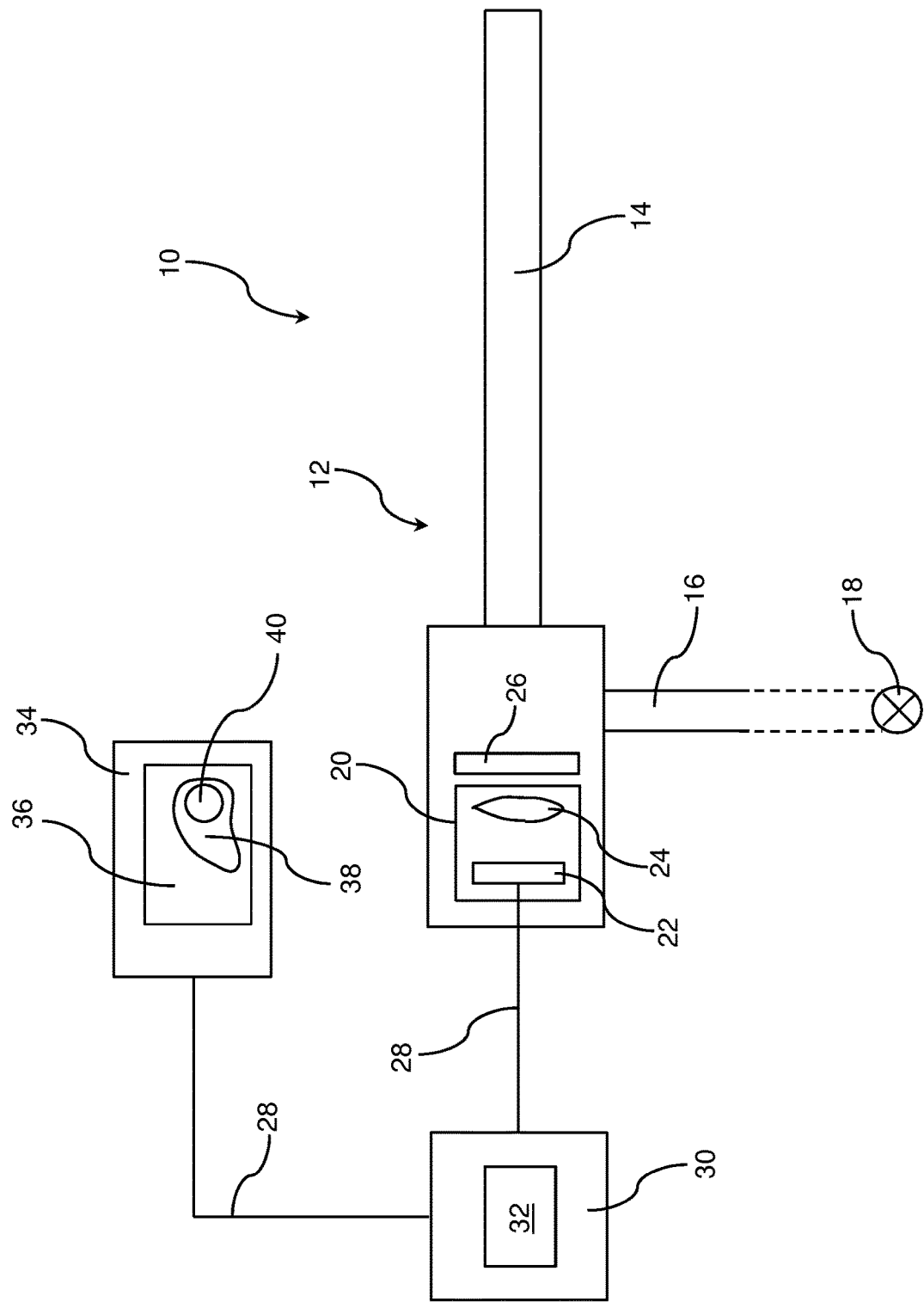
FIG. 2 is the schematic representation of a laparoscopic system configured for MSI-based augmented imaging.
Figure 3:
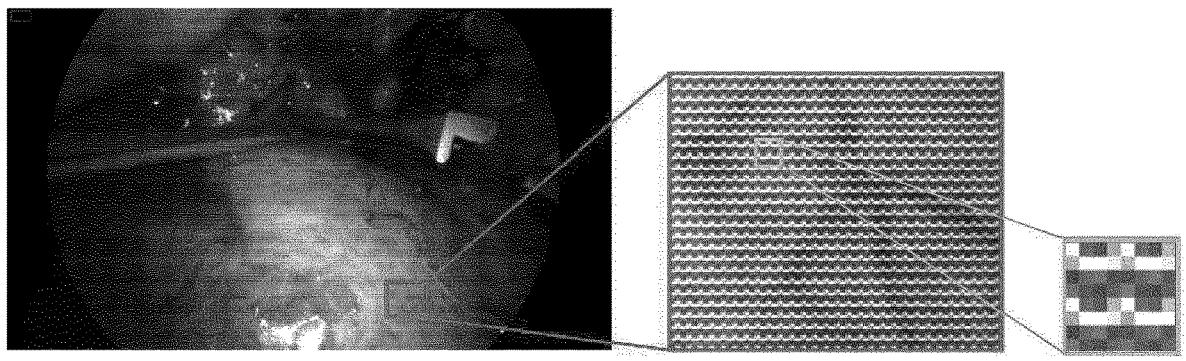
FIG. 3 shows a mosaic pattern visible when zooming twice into a single image.

In order to allow for augmented imaging at video rate, in one embodiment, a laparoscopic system 10 has been provided which is schematically shown in FIG. 2. The laparoscopic system 10 comprises a laparoscope 12 having a shaft portion 14 and a light guide 16 connected with an illumination light source 18. The laparoscope 12 is different from prior art laparoscopes in that it comprises a small and lightweight multispectral snapshot camera 20 comprising a multispectral snapshot image sensor 22 and suitable imaging optics 24. In preferred embodiments, the multispectral snapshot camera 20 allows for live imaging at video frame rates of higher than 25 Hz. In one embodiment, the Ximea (Muenster, Germany) MQ022HG-IM-SM4X4-VIS multispectral snapshot camera 20 has been combined with a commercially available laparoscope. The Ximea camera includes a mosaic snapshot sensor 22 with a frame rate of up to 170 Hz for image cubes of 512×272×16 resolution, where the third dimension resembles 16 available color channels. The sensor is made by the Interuniversity Microelectronics Centre (IMEC) in Leuven, Belgium and has a bit depth of 10. The sensor acquires the complete multispectral image at a single snapshot, using a 4×4 repeating mosaic pattern. FIG. 3 shows the mosaic pattern when zoomed twice into a single image.

In the system 10 of FIG. 2, a blue/green filter 26 is placed in front of the camera 20. As the tissue reflects red brighter than blue, by using the blue/green filter 26, information from red and from blue are recorded at more balanced camera counts, and at similar noise levels. A suitable blue/green filter is a filter that has an average transmissivity in a wavelength range between 400 and 600 nm that is higher than the average transmissivity in a wavelength range between 600 and 750 nm.

The camera 20 is connected via a data link 28 with a computing device 30 comprising a machine learning module 32. The data link 28 may be a wired or wireless connection. The machine learning module 32 may be a software module installed on the computing device 30. The computing device 30 can be a PC or workstation and preferably has a graphics processing unit (GPU) suitable for rapid processing of the machine learning based processes. However, in other embodiments, the computing device 30 could be an FPGA, which is particularly suitable for incorporating into commercially available platforms, such as platforms currently used by laparoscope manufacturers or the like. The machine learning module 32 receives the sensor data from the multispectral snapshot image sensor 22, subjected to suitable processing by the computing device 30 to determine the tissue parameters needed for the augmented imaging. A display device 34 is connected with the computing device 30 by a further wired or wireless data link 28. The display device 34 can be an ordinary display arranged in an operating room. In FIG. 2, an image 36 is schematically shown on the display 34, including an RGB image 38 of an organ on which an augmented image 40 indicating tissue parameters such as oxidization or blood volume fraction is overlaid.

With the random forest approach proposed above, it was found difficult to generate the augmented images for this camera at a required speed for fulfilling the 25 Hz requirement. To match the fast recording with equally fast analysis, the random forests were replaced with convolutional neural networks (CNN) known e. g. from Y. Lecun, L. Bottou, Y. Bengio, and P. Haffner. *Gradient-based learning applied to document recognition. Proceedings of the IEEE*, 86(11): 2278-2324 (1998) which allowed for the desired processing speed with reasonable hardware efforts. A further advantage of CNN is that image demosaicing and calibration can naturally be formulated as (convolutional) operations within the CNN architecture and that CNNs can operate on whole images and image patches, thus taking advantage of neighborhood information for contextual information processing.

Figure 4:
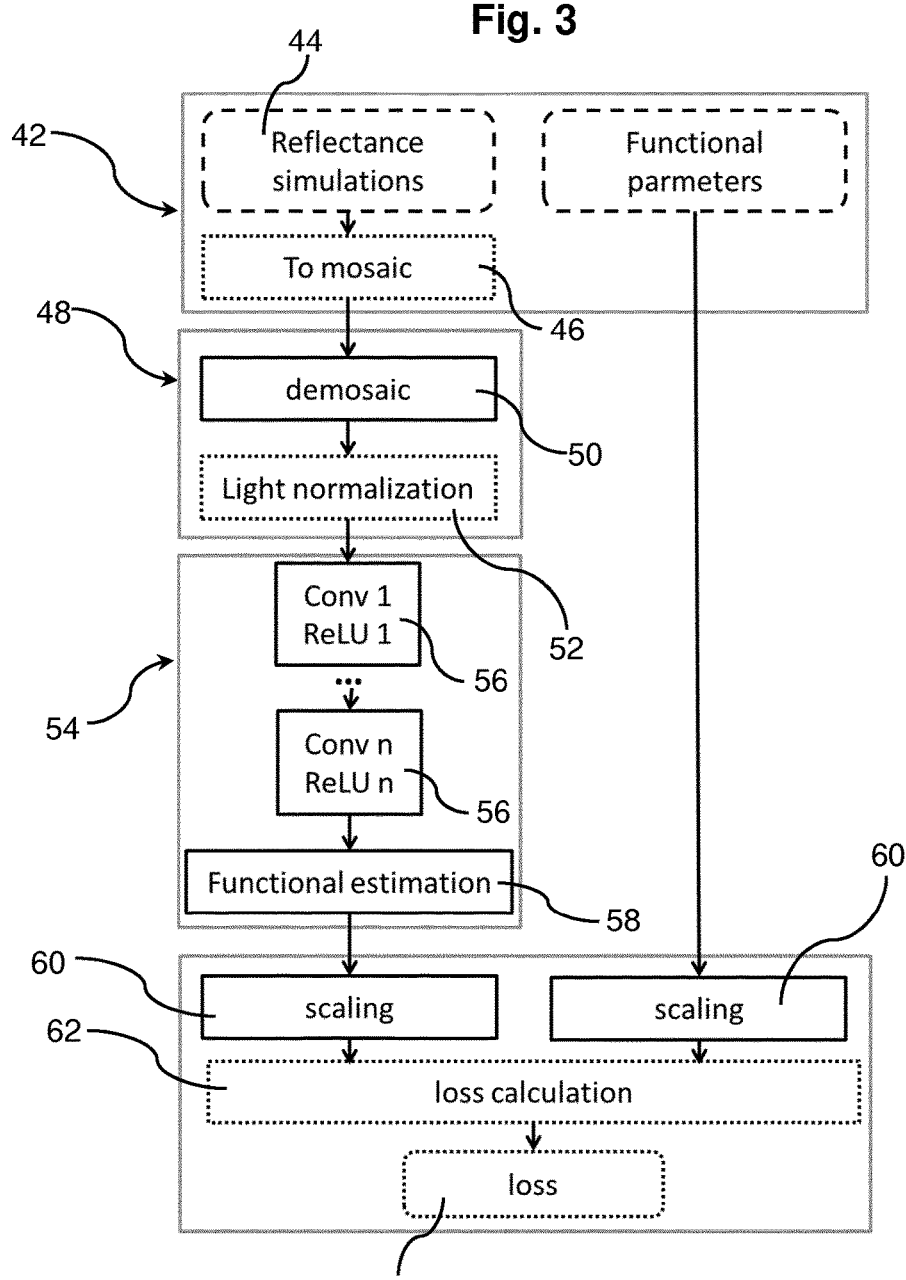
FIG. 4 is a schematic representation of an offline training network.
Figure 5:
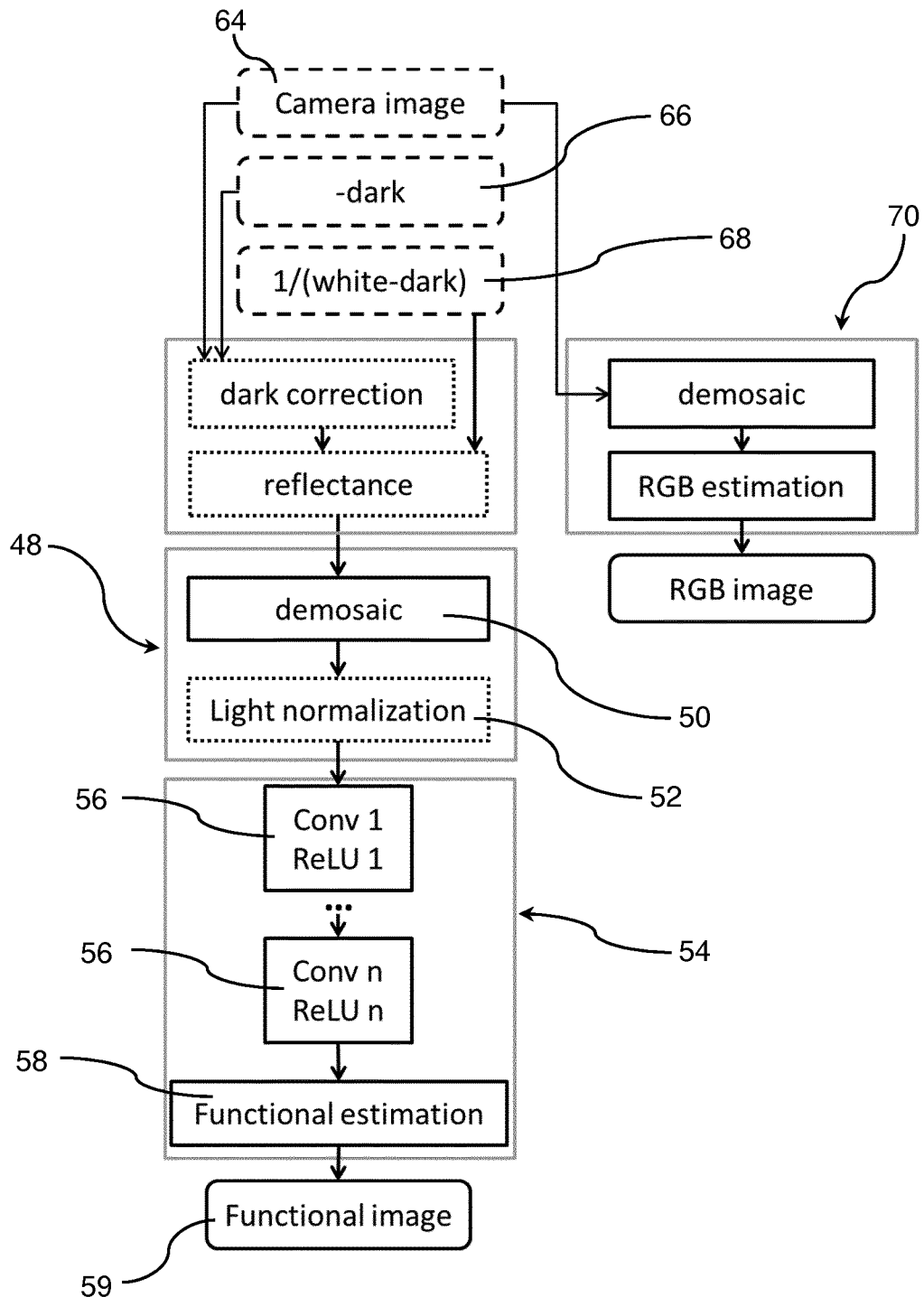
FIG. 5 is a schematic representation of a live evaluation network which processes new images in real time during an intervention.

In one embodiment, two networks are created. The offline training network shown in FIG. 4 determines weights and biases for functional estimation. The trained weights and biases are put into the live evaluation network shown in FIG. 5, which processes new images in real time during the intervention. The networks can be separated into several modules, explained in the following. In FIGS. 4 and 5, for easy reference, blocks related to input are indicated by dashed frames, blocks related to convolution are indicated by solid frames, and other blocks are indicated by dotted frames.

Data Preparation

The spectral reflectance of tissue is an intrinsic property of tissue, which is independent of the imaging system employed. Nonetheless, the recorded reflectance can be influenced mainly by: camera filter responses, camera quantum efficiency, illuminant relative irradiance, etc. Hence, adaptation of simulated spectra to the corresponding imaging hardware is needed.

With reference to FIG. 4, data preparation module 42 is provided for training only and serves to convert the simulations of spectral reflectance into data which as closely as possible resembles measurements from the multispectral imaging camera used. However, the adaption of simulations may also happen outside of the network during the training.

The same type of spectral reflectance simulations described above can be used for this purpose and are carried out in block 44. Through camera quantum efficiency and filter transmission measurements provided by the manufacturer and light source relative irradiance, laparoscope transmission and glass filter transmission measurements from a spectrometer, the spectral reflectance simulations are transformed to normalized reflectance space.

These pixel-wise normalized reflectance simulations are used as basis for functional estimation as described above. However, the mosaic pattern of the specific single snapshot sensor 22 used has a certain spatial extent. The present embodiment simulates local neighborhoods as captured by the sensor. In case of a snapshot multispectral sensor, each spectrum already has a spatial extent (for example 4×4 for a 16 band measurement using the snapshot sensor 22 of FIG. 2, called "mosaic" below). In this case, spectra are presented to the CNN as mosaics. Changes in tissue composition within the mosaic could thus lead to abrupt changes of the measured spectra at these locations. To account for this effect, in this embodiment mosaics are simulated by augmenting rearranging the simulated normalized reflectances $x_i$ in a mosaic pattern (see block 46), to thereby account for small neighborhoods within which the tissue can change. A second, randomly drawn staining sample $x_j$, also referred to as "disturbing simulation", is arranged in the same manner. The original simulated sample $x_i$ and the randomly chosen staining sample or disturbing simulation $x_j$ are shown in FIG. 6(a), and the rearrangement in the mosaic pattern is shown in FIG. 6(b). The pixels of the original mosaic are exchanged with pixels of the "disturbing mosaic" with a certain probability (e.g. 20%). To make the results more robust, a small patch of 3×3 mosaics was simulated, so that one training sample consists of 9=3×3 mosaics with the same base $x_i$ and staining $x_j$ reflectances, as shown in FIG. 6(c). In FIG. 6(c), pixels or elements of $x_i$ that were replaced by pixels/elements of the disturbing simulation $x_j$ are indicated by a thick border.

In this embodiment, it is exploited that CNNs provide the possibility to incorporate regions with a spatial extent into the estimation process. In this embodiment, the system can base functional estimation (or the estimation of other types of tissue parameters) not only on one spectral measurement, but on a neighborhood. Given homogeneous tissue, moving from a single (noisy) spectral measurement to an area is advantageous because this provides multiple (noisy) measurements to base further reasoning on. Disadvantages of moving from (almost) point based region to a larger area are disturbances such as tissue and lighting inhomogeneities.

In the embodiment shown in FIG. 6, a spatial neighborhood is incorporated. That is to say, the fully trained regressor is not applied to a single "multispectral pixel" or "mosaic" within the real multispectral image, but to a neighborhood of the real image, as is schematically shown in FIG. 6(d). FIG. 6(d) shows a 4×4 "mosaic", for which the tissue parameters are to be determined by means of the trained regressor. Incorporating neighborhood here means that the regressor is actually applied to some "evaluated neighborhood" around the 4×4 mosaic, which in this case also includes the eight closest mosaics surrounding the mosaic for which the tissue parameters are to be determined. In FIG. 6(d), the evaluated neighborhood is indicated by hatching. After the trained regressor is evaluated on this evaluated neighborhood, the regressor is moved one mosaic further and evaluated again, which is indicated as "next neighborhood" in FIG. 6(d). This procedure can be regarded as "convolutional sliding of regression window".

For the purpose of training the regressor, the "evaluated neighborhood" is provided by copying the same mosaic several times until the desired spatial extent is matched, i.e. in the given example, eight times. Noise is added to all measurements independently, as is schematically shown in FIG. 6(e). This brings the advantage of processing regions, namely to be able to base reasoning on multiple measurements. To also model the disadvantages, especially tissue inhomogeneities, several means of varying model complexity may be chosen.

One simple model for tissue inhomogneity assumes that these occur randomly in the simulated neighborhood. Precisely this assumption has been made in the FIG. 6(c), where random inhomogeneities were simulated by replacing, with a certain probability (in FIG. 6(c) 20%), each pixel within each mosaic of a "base tissue" (see FIG. 6(f)) by a randomly chosen measurement from a different tissue.

Other embodiments can employ more complex models for tissue inhomogeneities, such as modeling typical shapes like tissue borders or vessels with differing orientation, as is schematically shown in FIG. 6(f), which shows for comparison a situation where the inhomogeneity is random (top), and a situation where typical shapes, in this example a vessel is modelled (bottom).

To model sensor noise, zero mean Gaussian noise may be added to the simulations as explained above. In the embodiment shown, both oxygenation and blood volume fraction were selected to be the tissue parameters for regression, but it is understood that other tissue parameters could likewise be chosen. They were set to the mean values within the first 250 μm within the artificial tissue. The simulated mosaic patches served as input to the normalization module 48, which is part of the training (FIG. 4) and of the live evaluation network (FIG. 5).

Normalization

In the normalization module 48, mosaic images are demosaiced (block 50) to separate spectral and spatial domains into individual axes. This can for example be achieved using a bilinear interpolation as described in R. Zhen and R. L. Stevenson. *Image Demosaicing. In Color Image and Video Enhancement*, pages 13-54. Springer, Cham (2015). ISBN 978-3-319-09362-8 978-3-319-09363-5 or by learning the interpolation within the CNN framework, cf. M. Gharbi, G. Chaurasia, S. Paris, and F. Durand. *Deep Joint Demosaicing and Denoising. ACMTrans. Graph.*, 35(6):191:1-191:12 (2016). In this embodiment, demosaicing 50 is implemented by stacking each mosaic of 4×4 to a 16 dimensional vector. This operation may be implemented by shifting a 4×4 kernel with 16 output channels and a stride of four over the image. Each of the 16 kernel channels then has a 1 entry in the extracted mosaic pixel and zeros elsewhere. It is to be noted that this simple way of demosaicing introduces a small spatial misalignment due to the spatial extent of each mosaic, which however still allowed to receive very good results.

In the present embodiment, both real measurements and simulations are normalized to account for constant changes in illumination. These changes are caused by varying light source intensities or illuminating conditions, such as poses of a laparoscope or the distance of an operating room light from the tissue of interest. In this embodiment, this is done in block 52 by dividing each of the demosaiced reflectances by its $\ell^2$ norm. The normalized reflectances then serve as input for the functional estimation module 54.

Functional Estimation

The functional estimation module 54 could be regarded as the heart of the network, in which the relationship between input data and tissue parameters is established. In the embodiment shown, it is composed of several convolution/rectified linear units (ReLU) blocks 56 of a type further described in V. Nair and G. E. Hinton. *Rectified linear units improve restricted Boltzmann machines. In Proceedings of the 27th international conference on machine learning (ICML-10)*, pages 807-814 (2010). In the most simple embodiment, all blocks 56 are 1×1 convolutions, denoting the same result as a fully connected, pixel-wise network applied to each image pixel. If patch-wise 3×3 mosaic input is generated as described above, the first two layers are 2×2 convolutions, followed by 1×1 feature transformations. Because of the fully convolutional architecture, patches and images of arbitrary sizes can serve as input to the network. The number of convolutional layers and filters depends on the implementation, weights and biases are learned with respect to the loss described next. The result of the operations, representing an estimate for the tissue parameter image or images (in case more than one tissue parameter is determined, such as oxygenation and blood volume fraction) is then obtained in block 58.

During training, the obtained functional estimation in block 58 is compared with the true tissue parameters of the tissue. Since in the present embodiment, the tissue is simulated using a tissue model of the type described above, the "true tissue parameters" are known, and sufficient datasets can be generated to carry out an efficient training. The comparison with the true tissue parameters of the tissue may be carried out by means of a loss calculation as described in the next section. In the live evaluation network shown in FIG. 5, the same functional estimation module 54 is employed, but in this case, the underlying CNN has been sufficiently trained using the training network of FIG. 4. Accordingly, in this case the "augmented image estimation" 58 is actually expected to be a very good representation of the tissue parameter image of the tissue represented by the camera image 64, and is outputted as the functional image in block 59. Note that carrying out the functional estimation by means of the machine learning based functional estimation module 54 is an example of what is referred to as "applying a machine learning based regressor" to a multispectral image herein. Note that while specific reference has been made to functional parameters herein, this embodiment is likewise applicable to other types of tissue parameters as referred above.

Loss

The loss is the objective function to be minimized during training. In the embodiment shown, an Euclidean loss was chosen and employed in block 62, defined as $$\frac{1}{2N}\sum_i^N \|y_{true,i} - y_{pred,i}\|_2^2, \quad (10)$$

with N being the elements in the training batch, and the result of the loss calculation is obtained in block 63. Tissue parameters come in differing ranges. In the employed data set, oxygenation varied from 0-100%, while blood volume fraction only ranged from 0-30%. To ensure that different ranges of the estimated parameters do not influence the loss, the real $y_{true}$ and estimated $y_{pred}$ were scaled in block 60. This scaling was determined on the training data so that the training labels range from 0 to 1 for each parameter. The trained weights and biases were copied to the in vivo evaluation network.

Calibration

With reference to FIG. 5, before the normalization and functional estimation are applied to the in vivo network, the camera images 64 are transformed to reflectance. Two images were recorded before the intervention for this purpose: a dark image with no light and a white image, taken from a white reflectance standard, such as a standard white reference. The reflectance can then be computed as: R=(I−D)/(W−D) where "R" represents the reflectance and "I" the image. This normalization can be incorporated into the network as addition and multiplication operations that can then be highly parallelized in order to speed up computations. Therefore, white and dark recordings were stored in the network to be simply added (−dark) and multiplied (1/(white−dark)), see blocks 66 and 68.

RGB Estimation

To also show the physician a familiar image as a reference during the intervention, an RGB image is simultaneously estimated.

As indicated in FIG. 5, this calculation takes place in a separate path 70 and aimed to reconstruct an idealized RGB filter response $F_{RGB} \in R^{3 \times m}$ from the multispectral systems response $F_{multispectral} \in R^{|b| \times m}$ using a linear transformation $T \in R^{3 \times |b|}$:

$$F_{RGB} = T \cdot F_{multispectral}$$

with m being the number of parsed wavelengths and |b|, the number of multispectral bands. Filter matrix $F_{multispectral}$ can incorporate light source irradiance and transmission of the optics employed to make the estimation inherently white balanced. The linear transformation T may be found by least squares regression and put into the network. Here the transformation was represented by three 1×1 filters, one for each R, G and B, with no biases.

Practical Implementation: Video Rate Laparoscope

One target application is partial nephrectomy, in which a kidney tumor is surgically removed. During these interventions, often the renal artery has to be clamped to prevent bleeding. Verification of correct clamping is not straightforward; especially if the preferable selective clamping of a segmental artery is performed, in which ischemia is induced only in the cancerous part of the kidney. One possibility to ensure correct clamping according to prior art is to check perfusion with indocyanine green (ICG) fluorescence: after ICG is injected in the blood stream, it binds to the plasma. The bound ICG travels through the blood stream and accumulates in the internal organs, especially in the kidney and liver within a minute. No fluorescent signal thus corresponds to no perfusion. Due to long washout periods of about 30 minutes, this test is not repeatable if the wrong segment has been clamped.

Multispectral imaging (MSI) methods of the present invention are capable of substituting for the only once applicable fluorescence method. With reference to FIG. 7 to 11, results demonstrating the performance of the approach are shown. FIG. 7 shows mean oxygenation values obtained by different methods for comparison, namely by using a CNN regressor, a random forest regressor and the standard Beer-Lambert approach. In each case, the oxygenation is shown as a function of time, while consecutively two clamps were applied to the renal artery. FIG. 8 shows the corresponding standard deviation of the different methods within the region of interest. All three measurements reveal a considerable drop in oxygenation with time. However, a small dip of oxygenation within the first minute after the first clamping could only be measured with the CNN approach. Note that the Beer-Lambert approach gives impossible oxygenation values greater than 100%. It is seen that the CNN regressor gives the best performance.

Figure 10:
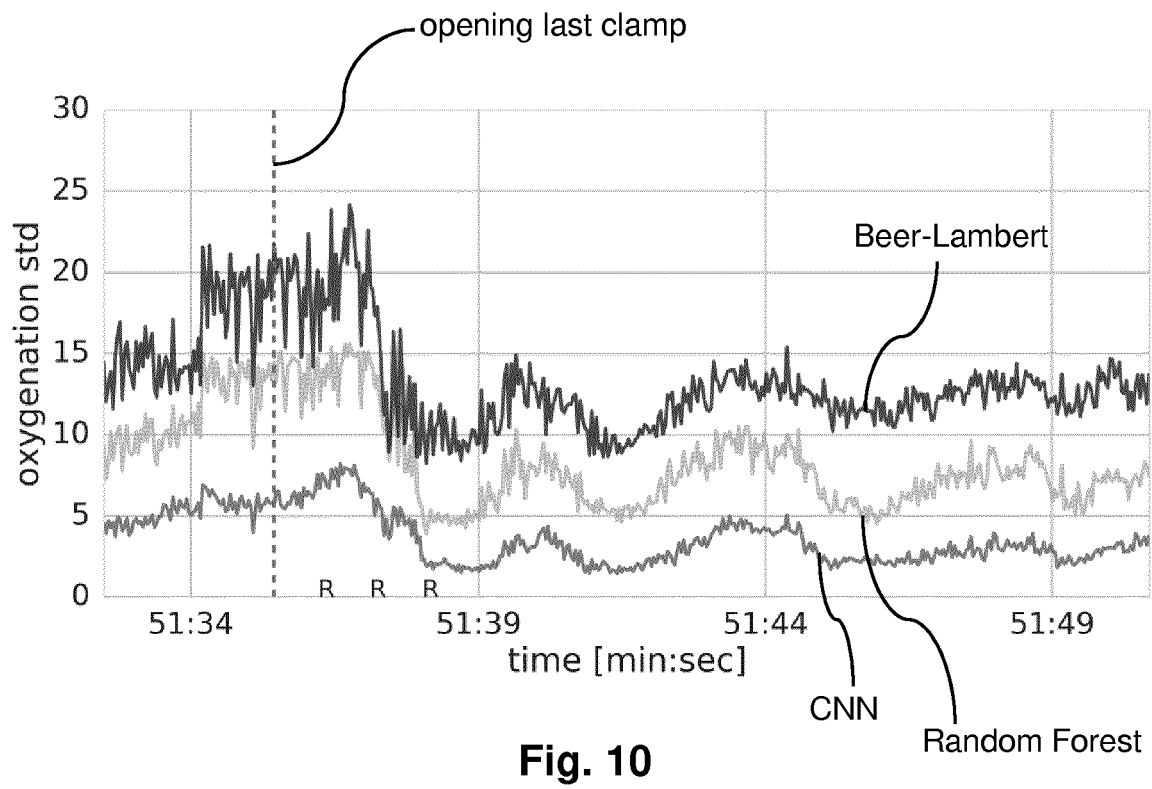

FIGS. 9 and 10 show the mean oxygenation and the standard deviation in a similar manner as FIGS. 7 and 8, but for a situation after the last clamp is opened, leading to a recovery of the oxygenation. It is again seen that both of the machine learning-based approaches are superior over the simple Beer-Lambert approach, and that again the CNN regressor has superior performance over the random forest-based regressor.

Finally, FIG. 11 shows the mean oxygenation as a function of time determined with different training methods for the CNN. The four datasets show the possible combinations of whether the training is based on a small neighborhood ("patch") or a single pixel ("pixel"), and whether additional noise coming from nearby tissues was simulated ("staining") or not ("no staining"). All methods show the same general trend. The preferred approach which combines both, the patch and the staining estimates higher non-ischemic oxygenation, which is physiologically more plausible, and is also substantially less noisy. In each of FIG. 7 to 11, the letters "R" indicate a re-initialisation of the region of interest. A template matching based region of interest tracker was developed to follow a region of interest through the videos. Due to substantial movement and thus perspective change, the region of interest was initiated at approximately the same position after applying the first clamp, applying the second clamp and before releasing the clamps.

As was explained above, as part of the adaption of the simulations in the forward model to the imaging system, the spectral composition of the illumination light used is accounted for. This can in fact be quite easily done if the MSI-based augmented imaging is used in a minimally invasive scenario, e.g. in endoscopic or laparoscopic interventions, where the illumination light is solely provided by the instrument used and hence known and well controlled. However, if the MSI-based functional imaging is carried out in open surgery, the spectral composition of the illumination light is not easily controlled, because it will depend on the various light sources used in the operating room. Moreover, since the patient and/or the light sources will be moved under surgery, the composition of the illumination light may constantly change.

To deal with this situation, during the online application (cf. lower half of FIG. 1), an autocalibration step is carried out which is explained in more detail with reference to FIGS. 12 and 13. The autocalibration 74 comprises two steps, namely a step 76 of estimating a spectral composition of the light currently illuminating a region of interest of the tissue, and a step that ensures that the machine learning based regressor 72 indeed matches the estimated spectral composition of the illumination light. In the embodiment of FIG. 12, the spectral composition of the light source is estimated from specular reflections, also referred to as "specularities" herein, which will be explained in more detail below. Moreover, in this embodiment the spectral composition is determined based directly on the 16 color channels of the MSI sensor for simplicity, since these values are readily available.

Regarding the second step, two different variants may be employed. In the first variant shown in FIG. 12, a plurality of regressors 72 are provided, which were each trained on different model light sources (light source 1, light source 2 and so on). These different model light sources are also referred to as "training illuminations" above. The different model light sources 72 have different spectral compositions, covering the most typical spectral compositions that can occur in operation room lighting conditions. The autocalibration comprises a step 78 in which the regressor is selected among the plurality of previously trained regressors 72 that is associated with the model light source that is the most similar to the "estimated light source". In the example shown in FIG. 12, the spectral composition of the model light source 2 is the closest to the spectral composition of the estimated light source, such that the corresponding regressor 72 is used in the online application for determining the tissue parameters. This way, highly reliable tissue parameters can be determined in spite of the fact that the actual illumination spectrum of the region of interest is not previously known. Moreover, the autocalibration 74 can be repeated at comparatively short intervals of as little as one minute, 30 seconds or even less, such that the MSI-based augmented imaging can constantly adapt to changing illumination conditions.

In the second variant, schematically shown in FIG. 13, only a single regressor 72 is provided, which was trained based on a "generic light source". Herein, the "generic light source" is a light source having a spectral composition that is typical to occur at the patient site in the operating room, and provides an illumination that is referred to as the "standard illumination" above. In this variant too, a step 76 of estimating the spectral composition of the actual light source from specularities is employed, but in this case, a full spectrum is estimated, in a manner described in more detail below. Then, in a step 80, the measurements are "transformed to generic light source". This means that the obtained multispectral image is transformed, based on information derived from the estimated spectral composition in step 76, to a transformed multispectral image to which then the regressor 72 trained on the generic light source is applied. The transformation applied in step 80 is capable of compensating a change in the multispectral image due to a deviation of the spectral composition of the actual light source from that of the generic light source. In other words, after the transformation, the multispectral image "looks" like or at least similar to a multispectral image that would have been obtained of the same region of interest if it had been illuminated with the generic light source.

In exemplary embodiments, the transformation applied in step 80 may be performed by defining a standard optical system F1, which is a n×m matrix, with each row representing one filter and each column representing transmission in one wavelength (e.g. 300 to 1000 nm in 2 nm steps). F1 could for example be composed by taking the filter transmission of the multispectral camera and multiplying a Xenon light source irradiance spectrum. A second matrix F2 of size 1×m represents the actual knowledge about the current optical system.

Note, that the number of filters 1 in the second matrix F2 could equal n, but this is not a necessity as F1 represents a fictional, idealized system. F2 comprises the filter transmission, the estimated light source spectrum and all other knowledge about the optical system, such as a glass filter or the like. A transformation T [1×n] may then be determined by linear regression to match F1 and F2: F1=T*F2.

In a third variant, the regressor could be retrained with the simulation data adapted to the current estimate of the light source. The CNN parameters of the original regressor may serve as a starting point for training (transfer learning) which greatly reduces training time of the regressor.

Next, with reference to FIG. 14, an embodiment of the method for estimating the light source from specular reflections according to step 76 is described in more detail.

In step 82, specular highlights, i.e. regions of specular reflection are identified in the MSI. In one embodiment, this step 82 comprises the following substeps:

A substep 84 in which the multispectral image is transformed to the HSI (hue, saturation, intensity) color space. The HSI color space is particularly suitable for determining specular highlights, as it separates color from intensity and saturation. The corresponding transformation matrix can again be determined using linear regression, in a similar manner as described above with respect to the RGB estimation. In particular, the transformation to HSI color space may be based on the RGB estimate of the multispectral image described above. Suitable formulas for the final step of transforming from RGB to HSI color space are e.g. suggested in J. Serra, *Espaces couleur et traitement d'images*, Centre de Morphologie Mathématique, Ecole des Mines de Paris, Paris, France, Tech. Rep. N-34/02/MM, 2002, as follows:

$Int=(R+G+B)/3;$ $Sat=(2R-G-B)/2$ if $(B+R)>=2G;$ $Sat=(R+G-2B)/2$ if $(B+R)<2G;$

Color information is contained in both hue and saturation. The saturation describes the 'purity' of the color—a specular reflection of a white light source will have R, G as well as B-component and thus a low saturation, whereas the diffusely reflected light from the red tissue will have less G and B contribution, corresponding to a higher saturation. Accordingly, by transforming the multispectral image, or the RGB image derived from the multispectral image, to HSI space allows for a more reliable detection of specular regions as compared e.g. to looking for matching high intensity zones in R, G and B histograms. Indeed, determining specular highlight pixels from these histograms would typically require histogram post-processing/denoising, as described in Stephane Tchoulack et al., *A video stream processor for real-time detection and correction of specular reflections in endoscopic images*, Joint 6th International IEEE Northeast Workshop on Circuits and Systems and TAISA Conference, 2008, which can be avoided when operating in the HSI color state.

Step 82 further comprises a substep 86, in which the HSI image is segmented into specular regions and non-specular regions, for example using statistics-based thresholding. The result of the segmentation can for example be a binary image having a value of 1 for a specular reflection and a value of 0 for non-specular reflection.

Finally, step 82 further comprises a substep 88, in which the thus identified specular regions are sorted according to size. Some of the "specular regions" may be formed by single pixels or a region of only a few adjacent pixels, which tend to be outliers and not suitable for estimating the illumination light source spectrum. Moreover, the largest connected region in the segmented image is often actually formed by a diffusive background, and is therefore likewise discarded. Accordingly, the first to n-th largest connected regions of specular pixels are determined, where n is a suitably chosen integer number, wherein it is to be noted that the largest connected region of specular pictures is usually the second largest connected region in the segmented image.

In practice, it turns out that the specular regions may contain overexposed or saturated pixel values. An overexposed pixel value has a maximum intensity value for a given pixel, for example a value of 256 in an 8-bit camera. These overexposed pixel values do not give useful information regarding the spectrum because part of the spectrum is truncated by the saturation of the corresponding pixel sensor element. In order to deal with such overexposed pixels, in step 90, the specular regions are subjected to morphologic dilatation, until they include a predetermined number or percentage of non-saturated pixels. In mathematical morphology, "dilation" is an operation that uses a structuring element for expanding shapes contained in an input image. In preferred embodiments, a 3×3 pixel large structuring element is used for morphology—dilating the specular region in the demosaiced image. The rationale behind this dilation is that in the neighborhood of a specular region, diffuse and specular components are mixed, such that the additional pixels incorporated by the dilation would still include specular information. The morphological expansion of the specular region will preserve the general shape of the specular region.

In subsequent step 92, within the specular region, diffused and specular reflection components are separated. In one embodiment, this is carried out using a principal component analysis (PCA). PCA is a statistical procedure that uses an orthogonal transformation to convert a set of observations of possibly correlated variables into a set of values of linearly uncorrelated variables called principal components. If there are n observations with p variables, then the number of distinct principal components is min (n−1,p). This transformation is defined in such a way that the first principal component has the largest possible variance (that is, accounts for as much of the variability in the data as possible), and each succeeding component in turn has the highest variance possible under the constraint that it is orthogonal to the preceding components. The resulting vectors are an uncorrelated orthogonal basis set. Under the reasonable assumption that the tissue properties are to a certain degree similar within the specular region, it can be assumed that the specular component s contributes an additive component to the measured spectrum m: m=s*l+ad$_1$+ bd$_2$+ . . . . Herein, l resembles the spectrum of the light source, which is preserved in the specular reflection, and d1 and d2 are diffusive components which may likewise vary (according to coefficients a and b). However, it is assumed that these variations are smaller than the variations caused by the specularly reflected light. The purpose of the PCA is now to determine the linear projection of the (centred) data which includes the maximum variance. Since it is assumed that the illumination light source causes the largest variations, i.e. largest variance in the specular region, this projection corresponds to the light source, and resembles the first principal component of the PCA. In another embodiment, the light source could be determined by independent component analysis (ICA), which is a summarizing term for methods which find statistically independent components in data. ICA is suited for this task because the light source illumination spectrum is independent on the tissue.

In step 94, based on the specular component of the light extracted from the specular region in preceding step 92, the spectrum of the illumination light source is estimated. In the simplest case, it is sufficient to determine the relative intensities of the individual color channels of the MSI sensor. When using the MSI camera 20 of FIG. 2 including the 16 channel multispectral snapshot image sensor 22 for an open surgery application, the intensities for the 16 color channels or bands that are attributable to specular reflection can be determined. This can be sufficient for the embodiment of FIG. 12, where it is only necessary to select the most suitable previously trained regressor 72.

However, particularly in case of the embodiment of FIG. 13, where the obtained multispectral image is to be transformed to match that of a standard illumination or "generic light source", it is advantageous to derive a quasi-continuous spectrum of the actual light source based on the limited number of color channels of the MSI sensor. In one embodiment, this is carried out by deriving a linear transformation matrix which transforms the k-dimensional measurement (with k being the number of color channels, i.e. 16 in the present embodiment) into a high dimensional, quasi-continuous frequency space. The "quasi-continuous" frequency space can for example span a frequency region of about 300 nm to 700 nm in steps of between 1.5 and 4 nm, for example 2 nm. This may for example be done using the Wiener estimation method disclosed in Izumi Nishidate et al., *Visualization of hemodynamics and light scattering in exposed brain of rat using multispectral image reconstruction based on Wiener estimation method, SPIE Proceedings (Optical Society of America*, 2015), paper 95360Z.

Note that the variant of FIG. 13 can be regarded as an application of the so-called "color constancy method". Color constancy methods seek to keep the perceived color of a surface constant despite changes in the spectrum of the Illumination. In other words, color constancy methods aim at producing "illumination-invariant". This is a challenging task, as neither the spectral reflectance of a surface nor the spectral irradiance of the illumination can be immediately derived from the reflectance spectrum.

Several approaches for color constancy methods have been suggested in the art, which shall not be discussed in detail here. Instead, reference is made to the overview given in Vivek Agarwal et al., *An Overview of Color Constancy Algorithms, Journal of Pattern Recognition Research* 1, 2006. While the prior art algorithms were developed for RGB Images, some of them allow for being adapted for multispectral Imaging.

Next, with reference to FIG. 18, a further and simpler variant for estimating the spectral composition of light illuminating a region of interest of a tissue is illustrated. Herein, the general idea is to frequently capture low exposure images, from which the illuminant can again be estimated via specular highlight analysis. In other words, based on low exposure multispectral images, specular highlight masks can be computed, which represent regions in the image that are not overexposed (due to the low exposure chosen). These regions are assumed to contain a dominant specular component yielding a direct reflection from which the spectral composition of the light source can be obtained when the signal is no longer in saturation. Note that in high exposure images, specular highlights tend to be saturated in which case they are not well suited for direct estimation of the light source's spectral composition). The estimation of functional tissue parameters is still performed on standard high exposure images with a machine learning method adapted to the illuminant parameters estimated from the low exposure specular highlights.

The procedure illustrated in FIG. 18 comprises the following three main steps:

(1) Acquisition of Low Exposure Images

While it is in principle possible to recover spectral information about the illuminant directly from the specular highlights of standard (i.e. high exposure time) multispectral images, in practice, specular reflections usually saturate the detector, leading to "invalid" pixels. Other parts of the image, on the other hand, are typically substantially affected by underlying tissue properties and thus not well-suited for the recovery of the illuminant. To overcome this problem, in this embodiment, the acquisition of low exposure time multispectral images for calibration is proposed. Note that in the present embodiment, "low exposure" always refers to a comparatively short exposure time. However, the disclosure is not limited to this, and low exposures could also be established using a small diaphragm opening, or the like. While these low exposure images are generally associated with a low signal-to-noise-ratio (SNR), the guiding hypothesis in this embodiment is that in these images, "valid" specular highlight pixels contain maximum spectral information about the illuminant. To determine the optimal exposure time for these low exposure images, several experiments were carried out as detailed below.

(2) Image Processing (Specular Highlight Segmentation)

In this embodiment, the low exposure images are processed using a specular highlight segmentation approach which involves removing overexposed and underexposed pixels by selecting pixels with intensities $I_{ms}$ in a specific range $I_{min} < I_{ms} < I_{max}$. Herein, $I_{min}$ is set to the level of dark current for a given exposure time, which only needs to be determined once for a given multispectral camera. $I_{max}$ accounts for the non-linearity in the camera response at high intensities and is set according to manufacturer specifications. This results in a set of pixel indices corresponding to a set of valid pixels $Idx_{valid}$. Based on this index set, specular highlight pixels are identified as follows. Initially, the lightness $(I_L)_{i,j}$ is computed for all $(i, j) \in IdX_{valid}$ by averaging the reflectance over all bands:

$$(I_L)_{i,j} = \sum_{k=1}^{n} \frac{(I_k)_{i,j}}{n}$$

where n is the number of bands and $(I_k)_{i,j}$ is the intensity corresponding to band k at pixel (i, j). From the "lightness image", a number of $N_P$ highlight pixels with the highest values of $(I_L)_{i,j}$ are selected. The corresponding indices are represented by $Idx_{hl} \subseteq Idx_{valid}$. Based on an empirical analysis described below, we choose $N_P=100$.

(3) Estimation of Illuminant

The illuminant in this embodiment is computed based on the idealized assumption that the diffusely reflected light from tissue can be neglected in specular highlight pixels chosen in the above manner. For each $(i,j) \in Idx_{hl}$ an estimate of the illuminant is computed by normalizing the acquired spectra $$I_{i,j} : \hat{L}_{i,j} = \frac{I_{i,j}}{|I_{i,j}|_1}$$

$\hat{L}$ is then set to the mean of all illuminant estimations from single pixels.

In this embodiment, the XIMEA (Münster, Germany) MQ022HG-IM-SM4X4-VIS mosaic camera was used which records multispectral images at 16 bands in the visible range at video framerates. Five different light sources (LS) representing commonly used illumination conditions were used to validate the described approach: LS 1: Xenon (Storz D-light P 201337 20, Tuttlingen, Germany); LS 2: Halogen (Osram light bulb, Munich, Germany); LS 3: Fluorescent Light (desk lamp); LS 4: Xenon (Wolf Auto LP 5131, Knittlingen, Germany); and LS 5: LED (Wolf Endolight LED 2.2, Knittlingen, Germany). The reference illuminant spectra of all LS were obtained with the Ocean Optics HR2000+ (Largo, Florida, USA) spectrometer over a white reference, as described in Antonio, R. K, Cong, P. H.: *Imaging spectroscopy for scene analysis*. chap. 3.2.2, pp. 24-25 (2013). The irradiance of LS 1-5 normalized as described below is shown in FIG. 19a.

To quantify the difference between two LS spectra, their illuminant spectra may be considered as vectors and the Euclidean angle between them may be computed, in the manner described in Khan, H. A. e.a.: *Illuminant estimation in multispectral imaging. Journal of the Optical Society of America A* 34(7), 1085 (2017). The angular distance for the five LS used in this study ranges from 1.0° (LS1 and LS4; both Xenon) to 25.9° (LS1 and LS3; Xenon and fluorescent) as depicted in a confusion matrix shown in FIG. 19b.

To generate in silico data for a quantitative validation, a multispectral imaging pixel is generated from a vector t of optical tissue properties as described in the section "layered tissue model" above, which are assumed to be relevant for the image formation process. To convert a vector of tissue properties to a simulated reflectance spectrum $r_{sim}(\lambda, t_i)$ (where a corresponds to the wavelength), the Monte Carlo method is applied. Intensity in band j of a pixel for a given LS and camera is then computed as $$i_j(t_i) = \alpha(p) \cdot w_j \int_{\lambda_{min}}^{\lambda_{max}} \xi_j(\lambda) \cdot r_{sim}(\lambda, t_i) d\lambda \forall j \in [1, B]$$

where $\xi_j(\lambda)$ represents the irradiance of the illuminant (e.g., Xenon or Halogen) and other components in the imaging system, such as transmittance of optical systems. $\omega_j$ is the camera noise for band j, B is the number of camera bands, and $\alpha(p)$ accounts for constant multiplicative changes of reflectance. By drawing samples $t_i$ from the layered tissue model and generating corresponding measurements, a data set of simulated multispectral measurements with corresponding ground truth oxygenation can be generated.

The inventors carried out experiments to assess how accurate and robust this approach to estimating the spectrum based on specular highlight analysis is. Moreover, the effect of errors in the estimation of the spectrum of the LS on the accuracy of functional parameter estimation was analysed.

For this purpose, multispectral images of an ex vivo pig liver illuminated with the five LS described in FIG. 19 were obtained. To determine the robustness of the described approach to illuminant estimation, images corresponding to a total of eight different poses of the camera relative to each LS (at different angles and distances) were taken. Images were recorded at different exposure times (5-150 ms), which were used for hyperparameter optimization.

The inventors determined empirically appropriate values for two hyperparameters, namely exposure time $T_{exp}$ for the calibration images (i.e. low exposure images) and number of highlight pixels $N_P$ per image. The inventors performed initial experiments using three of the five LS summarized in FIG. 19 namely LS1-LS3. These LS are referred to as validation LS herein, while we LS 4-5 are referred to as test LS. It was observed that varying $N_p$ in the range of 75-200 had a negligible influence on performance and thus a choice of $N_p=100$ was made. When analyzing the low exposure images in the validation set (exposure times between 5 ms and 150 ms), the inventors further found that the angular error of illuminant estimations decreases as the SNR increases, where the SNR is defined as:

$$SNR(T_{exp}) = median_{(i,j)}\left(\frac{(I_L)_{i,j}(T_{exp}) - \overline{D}(T_{exp})}{\overline{D}(T_{exp})}\right),$$

$$(i, j) \in Idx_{hl}(T_{exp})$$

with $\overline{D}(T_{exp})$ corresponding to the mean lightness value obtained for dark current (lights turned off), and $Idx_{hl}(T_{exp})$ representing the indices of the highlight pixels for exposure time $T_{exp}$. Note that the SNR does not necessarily increase with exposure time due to overexposed specular highlight pixels.

Based on these findings, in one embodiment, multiple low exposure images were acquired in a range of 5 ms to 150 ms (in steps of 5 ms), and then $T_{exp}$ was set to that (low exposure) image with the maximum SNR. Note that the inventors also investigated acquiring multiple images of the same $T_{exp}$ and averaging the corresponding results but did not find an improvement with this approach.

To quantitatively assess the performance of this embodiment of the method for illuminant estimation, the method was applied to a total of 40 (number of LS times number of poses per LS) images. Consequently, descriptive statistics for the angle between the reference spectrum and the estimated spectrum was computed.

To quantify the impact of the error in illuminant estimation on a resulting oxygenation estimation error, the inventors used the simulation pipeline presented above to simulate a set of ground truth optical properties $O_{train}$ with $|O_{train}|=15000$. These were used to generate 45 training sets, each corresponding to one of the five light sources $LS_i$ or their estimates $L\hat{S}_i$ (n=40; one for each of the eight poses for each LS) and each set comprising 5000 tuples of tissue properties and corresponding measurements. Note that the training sets for the different illuminants correspond to the exact same ground truth tissue parameters (including blood oxygenation, which in this example is the functional parameter to be recovered). For each training data set, a regressor for oxygenation estimation was trained using the approach described above. For testing the performance of the regressors, a test set for each of the five reference LS was generated, following the approach presented in the previous paragraph. Then descriptive statistics was computed for the quality of oxygenation estimation (1) using the reference illuminant for training ($LS_{train}=LS_{test}$; n=5), (2) using another illuminant for training ($LS_{train} \neq LS_{test}$; n=20) and (3) using the described approach to illuminant estimation to estimate the LS ($LS_{train}=L\hat{S}_{test}$; n=40).

For qualitative validation, a multispectral imaging stream was acquired from the lips of a human subject, and the LS was switched from LS 1 to LS 5 during recording. Automatic light source calibration was carried out to continuously update the regressor to one tailored to the (estimated) light source. As baseline method, the inventors applied a regressor trained on LS 1 (the first LS used) throughout the whole acquisition process. Qualitative analysis was performed by visual inspection of the oxygenation results in a region of interest (ROI).

FIG. 20a shows the reference illuminant spectrum (circles) along with the estimations (crosses).

The true illuminant is consistently the nearest neighbour to the estimates, with the exception of LS 1 and LS 4, which are both Xenon LS from different manufacturers and have an angular distance of only 1°. The performance of the described illuminant estimation method is summarized in FIG. 20b. It can be seen that the angle between the estimate and the reference is always below 3.0°. The performance for the test light sources LS4 and LS5 is similar to that of the validation light sources LS1-LS3, which were used to tune the two hyperparameters.

As shown in FIG. 21(a), the mean error in oxygenation estimation when using the ground truth illuminant for training ranges from 10.5% (LS 1) to 12.5% (LS 3), with a mean of 11.3% (averaged over all five LS). The mean, median and maximum value of the mean blood oxygenation error was 11.6%, 11.3% and 13.1% when applying the described approach (n=40). The results were similar for the validation LS (mean: 11.3%) and the test LS (mean: 12.0%). Compared to using an arbitrary LS (no calibration performed), the method according to the present embodiment reduced the mean blood oxygenation error by an average of 47%.

FIG. 21 (b) illustrates the benefit of the presented approach in vivo. When assuming a constant LS, the estimated blood oxygenation changes when illumination conditions alter (and do no longer match the training conditions). Herein, the changing illumination takes place between images 90 and 100. If the change in illumination is not accounted for, or in other words, if a "constant illumination" is assumed, this will lead to an error in blood oxygenation estimation, as is seen for images 100 to 200. The approach presented herein, however, compensates for the changing illumination spectrum by automatic LS calibration, such that even under the different illumination spectrum, the same blood oxygenation value is produced.

The guiding hypothesis that specular highlights extracted from low exposure multispectral images can be processed to recover the illumination spectrum with high accuracy, has been therefore been confirmed in the presented experimental analysis. It was further shown that the high quality of the estimations results in a high accuracy for recovering functional parameters, such as blood oxygenation in the presented example.

While the inventors optimized the hyperparameters $T_{exp}$ and $N_P$ on a subset of the LS used in the study, they did not observe a decrease in accuracy on the test LS. This can be attributed to the fact that the estimation results were robust to changes in these parameters.

Note that in the described embodiment, it is assumed that the illuminant spectrum is homogenous in the field of view of the camera. While initial experiments in a surgical environment suggest this to be good approximation, in preferred embodiments the method is extended such that different illuminants for different image patches are computed. Secondly, while in the described embodiment, the machine learning algorithm for oxygenation estimation is adapted by choosing a pretrained regressor from a discrete set of regressors, each corresponding to a different LS, in other embodiments, the other two variants described in the summary of the invention can be likewise employed. In other words, it is likewise possible to transform the obtained multispectral image based on information derived from the estimated illuminant spectrum and apply a standard regressor to the transformed multispectral image, which has been trained under standard illumination, where the transformation again compensates a change in the multispectral image due to a deviation in the spectral composition of the illumination from the standard elimination, and it is further possible to retrain an already trained regressor using simulation data that is adapted to the estimated illuminant spectrum.

While in the embodiment of FIG. 2 the MSI-based augmented imaging system 10 is associated with a laparoscope 12 which includes a multispectral camera 20, a multispectral camera 20 could also be directly provided in an operating room. In various embodiments, the camera 20 could be associated with an operating room light source which is used to illuminate the surgical site. For example, the camera 20 could be attached to an overhead surgical light source. This has the advantage that the illumination light of the tissue at the region of interest will be dominated by the light of the surgical light source having a known spectral composition, which makes it easier to provide a suitable regressor.

Similar to what is shown in FIG. 2, the camera 20 may be connected to a suitable computing device 30 including a machine learning module 32, and the computing device 30 may be connected to a display device 34 for displaying an RGB image 38 and a augmented image 40, possibly in an overlaid manner. The display device 30 could be installed in the operating room for the surgeon to turn to when additional information, such as functional information is needed.

FIG. 15 shows a yet further embodiment, where the multispectral camera 20 is associated with goggles 96. The multispectral camera 20 can be of the same type as the one discussed with reference to FIG. 2, including the mosaic multispectral snapshot sensor 22 (not shown in FIG. 15) that allows for recording multispectral images at a frame rate of 25 Hz are above, typically even 100 Hz and above. The goggles 96 comprise a data processing unit 98 which assumes the functionality of the computing device 30 of FIG. 2. In other words, the data processing unit 98 may apply the suitable regressor to the multispectral image data recorded by the multispectral camera 20 to thereby derive the tissue parameters to be displayed in a augmented image. If the data processing is too involved to be carried out by the comparatively small data processing unit 98, at least part of the computation can be carried out in an additional computing device 30 which is connected with the data processing unit 98 by a wireless link indicated by reference sign 100. Since the goggles 96 are typically worn in environments with varying illumination conditions, the autocalibration schemes described above with reference to FIGS. 12 and 13 are particularly useful in combination with the goggles 96.

In the embodiment shown, the augmented image will be displayed in the field of view of the goggles 96 in a manner per se known from augmented reality (AR) or "mixed reality" (MR) applications. This requires what is known as "hand-eye" calibration in the art. Accordingly, the augmented images can be overlaid the actual scenery seen through the goggles by the surgeon. In a preferred embodiment, the goggles 96 may further comprise a light source (not shown) for illuminating the tissue in the region of interest. Also, the goggles 96 are configured for recognizing gestures. For example, the processing unit 98 of the goggles 96 may include program code for recognizing a gesture of a surgeon pointing to a region of interest, which triggers the generation and displaying of the augmented image in the goggles field of view. In some embodiments, the user can "draw" a more complex region of interest using his or her finger that could indicate the boundaries of the organ or organs for functional or physiological parameter estimation. In yet further embodiments, the goggles 96 may use eye tracking to determine the location to with the user is looking to provide the corresponding tissue parameter estimation. Note that the term "eye tracking" as used herein has a broad meaning, and shall cover any way to determine the location to which the user is looking. In case of the goggles 96, this would mainly be determined by the movement of the head of the person wearing the goggles 96, but the term "eye tracking" is nevertheless used herein, it being understood that it also comprises "head tracking" or the like.

The goggles 96 further comprise a microphone 102 connected with the data processing unit 98 for enabling speech control. For example, the surgeon could point to an organ and say "show oxygenation" or "show blood volume fraction", which would trigger the generation and display of the corresponding augmented image.

Note that the various components described could be rearranged differently according to practical considerations. For example, the multispectral camera 20 need not be provided at the goggles, but could be installed at another place in the operating room and transmit the multispectral image information to the processing unit 98 via wireless link 100, or to a further computing device 30 for applying the regressor to the multispectral image data and for transmitting only the augmented image data to the data processing unit 98 of the goggles 96. Similarly, the microphone 102 need not be attached to the goggles 96 themselves, as long as the audio information or its content is conveyed one way or the other to the data processing unit 98 of the goggles 96.

In a particularly preferred embodiment, the goggles 96 are connected with an external database, for example a database in which preoperative data is stored, or with the PACS database, to provide additional information to be displayed in the goggles field of view. Also, the goggles 96 may be configured for carrying out teaching programs for medical students.

For example, the user could point to an organ and ask "which organ is this?", or "where is the liver?", and the answer is presented by visual or audio output of the goggles 96.

In preferred embodiments, the method and system of the invention can be combined with an anatomic structure classification, which is based on the same multispectral images, or parts thereof, that are also used for augmented imaging. In one embodiment, the method may include a step of automatically classifying the anatomic structure, and in particular the organ, to which the region of interest belongs, and to select the regressor among a plurality of available regressors that has been specifically trained for this type of organ. Another application is to use the organ classification in the additional information presented to the user in the goggles 96.

Various ways of automatic classification of anatomic structures have been suggested in the art, and the embodiment is not limited to any specific one of them. However, a new approach to anatomical structure classification and image tagging, which is particularly suitable for use in embodiments of the present invention, was recently proposed by some of the present inventors, which employs an intrinsic measure of confidence to estimate its own performance with high reliability. This measure was applied to both RGB and multispectral imaging data with drastic improvement of image tagging performance in both cases. Organ recognition was performed by:

1. Grouping similar regions using a superpixels
2. Calculating textural (Local binary patterns) and spectral (average spectrum) features for each superpixel.
3. Training a SVM classifier to estimate organ for each superpixel
4. Determining confidence of classification by analyzing the dispersion of class probabilities Note that the "superpixels" are an example of the "image regions" mentioned above, with which a tissue parameter could be associated. The assessment of confidence estimate was performed through a comprehensive in vivo study with seven pigs. When applied to image tagging, mean accuracy in the experiments increased from 65% to 90% (for RGB) and 80% to 96% (for multispectral), when including the confidence measure. This approach hence significantly improves over the current state of art on automatic labeling of endoscopic videos by introducing the use of the confidence metric, and by being the first study to use MI data for in vivo laparoscopic tissue classification. For more details, reference is made to S. Moccia et al., *Uncertainty-Aware Organ Classification for Surgical Data Science Applications in Laparoscopy*, DOI 10.1109/TBME 2018.2813015, which is incorporated herein by reference.

When multispectral imaging has been used in medical applications in prior art, imaging times have been very long, such that it has not been possible to exploit multispectral images in medical applications at a video rate, i.e. with frequencies of say 25 Hz or above. Usually, multispectral cameras would employ filter sets, often arranged in filter wheels, and for every color channel of the multispectral image, a new filter position has to be set, which obviously slows down the multispectral imaging considerably.

An important improvement has been presented herein above, where a multispectral sensor, shown in FIG. 2 under reference sign 22 allowing for imaging rates beyond 100 Hz was used. This was combined, in one embodiment, with a CNN based regressor, which allowed for deriving augmented images at the same high frequency and hence to the knowledge of the inventors for the first time allowed acquiring multispectral image based augmented images at video rates. However, since the multispectral sensor 22 employed multispectral pixels each composed of 4×4 single pixel sensors, for providing 16 color channel simultaneously, this comes at the price of a somewhat decreased spatial resolution.

One way of combining both, high processing speed and a high spatial resolution conceived by the present inventors is to try to devise an apparatus with a lower number of frequency bands in the multispectral imaging which, when properly chosen, would still permit deriving tissue parameters, and in particular physiological or functional information with high accuracy. However, the lack of tools in prior art to quantify performance of systems make it rather expensive to design a MSI systems for medical applications. In view of these deficiencies, the inventors developed a generic framework for quantitative and application-specific performance assessment of multispectral cameras and their optical system, which is presented below. Such a framework can be utilized for building and fine-tuning the various components virtually. Based on some user input on camera characteristics and properties of the target domain, such a framework would quantify the performance of the given camera configuration with large amounts of Monte-Carlo generated data and a user-defined performance metric.

The proposed workflow of the simulation framework for characterizing performance of custom designed multispectral filter bands for medical applications is shown in FIG. 16. The framework leverages simulation of light transport in multi-layered tissue to generate tissue-specific spectral reflectances. The framework developed by the inventors relies on Monte Carlo modeling of light transport in multi-layered tissues (MCML), as described in Wang L, Jacques S L. *Monte Carlo modeling of light transport in multi-layered tissues in standard C*. The University of Texas, MD Anderson Cancer Center, Houston. 1992:4-11, or the GPU accelerated version that has been described in Alerstam E, Lo W C, Han T D, Rose J, Andersson-Engels S, Lilge L. *Next-generation acceleration and code optimization for light transport in turbid media using GPUs. Biomedical optics express*. 2010 Sep. 1; 1(2):658-75.

These can then be combined with previously mentioned user input to obtain realistic camera measurements.

For band selection, within such a framework, custom band configurations for images can be compared by brute-force, considering all the possible band combinations. However, band selection approaches can be further refined using domain knowledge. Such techniques are inspired by feature selection methodologies for reducing the feature space. Possible approaches that have been tested by the inventors are:

Wrapper methods: Such methods rely on the regression function and—as the name suggests—wrap the regressor within an optimization function, while iteratively selecting bands that minimize a criterion such as 'mean absolute error'. Within this context the search for optimal bands can be modeled as a sequential search selection (SFS), as described in Whitney A W. *A direct method of nonparametric measurement selection. IEEE Transactions on Computers*. 1971 September; 100(9):1100-3, or a best first search (BFS) approach, as described in Kohavi R, John G H. *Wrappers for feature subset selection. Artificial intelligence*. 1997 Dec. 1; 97(1-2):273-32. Other possible search strategies can also be incorporated.

Methods relying purely on the input (X) and target data (Y): Such methods are also termed as "filter" methods. They are independent of the kind of regressor being employed. Different metrics can be employed for methods in this domain such as Conditional Mutual Information Maximization (CMIM) as described in Fleuret F. *Fast binary feature selection with conditional mutual information. Journal of Machine Learning Research*. 2004; 5 (November):1531-55); Interaction Capping (ICAP), as described in Jakulin A. *Machine learning based on attribute interactions* (*Doctoral dissertation, Univerza v Ljubljani*), and Joint Mutual Information (JMI) as described in Yang H, Moody J. *Feature selection based on joint mutual information. In Proceedings of international ICSC symposium on advances in intelligent data analysis* 1999 June (pp. 22-25), to name a few. Filter methods are typically used in discrete domain problems such as classification. To extend it to regression, which is a continuous domain problem, for the computation of conditional Mutual information with a continuous target variable, Kraskov's nearest neighbor mutual information estimator (Kraskov A, Stögbauer H, Grassberger P. *Estimating mutual information. Physical review E*. 2004 Jun. 23; 69(6):066138) is used instead of the typically employed histogram binning.

Using the workflow described above and schematically shown in FIG. 16, several band selection methods were compared for finding bands best suited. SFS was identified as the best method in this context. Specifically for oxygenation estimation, five bands were identified as the best suited, which are summarized in the table below.

| # | Central wavelength (nm) | FWHM |
|---|---|---|
| 1 | 495-505 | <20 nm |
| 2 | 535-545 | <20 nm |
| 3 | 550-570 | <20 nm |
| 4 | 575-585 | <20 nm |
| 5 | 590-610 | <20 nm |

In this table, the central column designates corresponding wavelength regions, in which the center of the band should lie. If all five wavelength bands are employed in the multispectral imaging, oxygenation results with excellent accuracy can be obtained. This compares favorably with the embodiments described above, in which, 16 wavelength bands were employed. Further analysis of the inventors revealed that in fact any combination of 4 out of the 5 proposed bands would give excellent results for oxygenation estimation. This allows e.g. for designing a multispectral sensor where each multispectral pixel is formed by 2×2 single color pixel sensors, detecting light in corresponding four out of the above five bands. This allows for increasing the resolution as compared to the multispectral sensor 22 described above by a factor of four, while still allowing for obtaining similarly good oxygenation results.

Surprisingly, the inventors could confirm that good oxygenation estimates can even be obtained when only three of the above five wavelengths are chosen. This allows for an even higher resolution, if the multispectral image sensor comprises only three single color pixel sensors. However, in the multispectral image sensor, three types of single color pixel sensors located in respective three out of the above five bands could be combined with pixel sensors detecting light within different bands that are provided for other imaging purposes.

For clinical applications, robustness of methods is typically of crucial importance. In preferred embodiments, it is therefore proposed to integrate methods for uncertainty quantification and compensation into the machine learning based algorithms used with the embodiments of the present invention. Main sources of uncertainty can be categorized in aleatoric uncertainty and epistemic uncertainty, cf. Kendall A, Gal Y. *What Uncertainties Do We Need in Bayesian Deep Learning for Computer Vision?* arXiv:170304977 [cs] [Internet]. 2017 Mar. 15. The former may e.g. describe the inherent noise introduced by the imaging modality, whereas the latter represents the model uncertainty mainly introduced e.g. by invalid assumptions or the lack of training data, for example.

Given the spectrum of a pixel along with the inferred tissue parameters, there are multiple ways to determine the uncertainty of an estimation:

Measures of confidence provided by machine learning algorithm: The uncertainty of an inference can be determined in an algorithm-specific manner. For support vector machines, for example, the posterior probability certainty index (PPCI) and the Gini coefficient (GC) can be used, as described in previous work by some of the present inventors, Moccia, S., Wirkert, S. J., Kenngott, H., Vemuri, A. S., Apitz, M., Mayer, B., . . . & Maier-Hein, L. (2018). *Uncertainty-aware organ classification for surgical data science applications in laparoscopy. IEEE Transactions on Biomedical Engineering*. In the case of random forests, the standard deviation of the individual trees may be used, as described in *Breiman L. Random forests. Machine learning*. 2001; 45(1):5-3. In convolutional neural networks (CNNs), several methods have been proposed including the estimation of conditional probability densities (Feindt M. *A Neural Bayesian Estimator for Conditional Probability Densities*. arXiv:physics/0402093 [Internet]. 2004 Feb. 18), the estimation of both model-based and image-based uncertainties (Kendall A, Gal Y. *What Uncertainties Do We Need in Bayesian Deep Learning for Computer Vision*? arXiv: 170304977 [cs] [Internet]. 2017 Mar. 15), and the so-called dropout sampling, as described in Kingma D P, Salimans T, Welling M. *Variational Dropout and the Local Reparameterization Trick*. In: Cortes C, Lawrence N D, Lee D D, Sugiyama M, Garnett R, editors. *Advances in Neural Information Processing Systems* 28 [Internet]. Curran Associates, Inc.; 2015 [cited 2018 Jul. 27]. p. 2575-2583. measures quantifying aleatoric uncertainty include a signal-to-noise-ratio and/or a contrast-to-noise-ratio.

Probabilistic inference: Traditional machine learning methods generate a single "hypothesis" given a measurement (e.g. one plausible parameter configuration given a measured spectrum). However, in preferred embodiments of the machine learning algorithms of the present disclosure, the machine learning is directed to deriving multiple plausible hypotheses instead, in a manner described e.g. in Simon A. A. Kohl, Bernardino Romera-Paredes, Clemens Meyer, Jeffrey De Fauw, Joseph R. Ledsam, Klaus H. Maier-Hein, S. M. Ali Eslami, Danilo Jimenez Rezende, Olaf Ronneberger *A Probabilistic U-Net for Segmentation of Ambiguous Images,* 2018, arXiv:1806.05034v1.

Other probabilistic approaches (e.g. approximate Bayesian computation) may be used to tackle inverse problems, whose forward process is well-understood. In such embodiments, a distribution of plausible parameter configurations (rather than one single estimate) is outputted for a given spectrum. If the distribution is uni-modal (and not too broad), the inversion of the acquired spectrum can be regarded a well-posed problem. Otherwise, the problem is ambiguous and the different modes of the distribution are outputted as alternative hypotheses, or in other words, "multiple plausible solutions".

In various embodiments, the uncertainty associated with a pixel or region may be used in multiple ways:

Visualization of uncertainty: The uncertainty can be made explicit by only visualizing estimations with high certainty and/or providing a quantification of confidence along with each measurement.

Confidence-based value aggregation: In such embodiments, confidence values may be used for an uncertainty-based aggregation of values, e.g. a weighted mean of inferred values taken from a region of interest, or the like.

Mode-based post-processing: Substantially different tissue parameter configurations may—in theory—yield similar spectra. Probabilistic methods of the types mentioned above have found to be able to recover the distribution representing the set of plausible parameter configurations that could have produced a specific spectrum. If the distribution features multiple modes, the ambiguity can potentially be resolved by taking additional measurements with a different hardware setup, for example different filter responses and/or a different illumination spectrum. This is schematically shown in illustrated in FIG. 17.

FIG. 17 illustrates a situation where different tissue parameter vectors (P1 and P2; here projected onto the first two principal components V1 and V2 in tissue parameter space) are found to yield almost identical spectra, when a first hardware configuration ("config. 1"), i.e. a first "imaging setup" is used. However, the ambiguity can be resolved by taking additional measurements with a different hardware configuration ("config. 2"). In preferred embodiments, the different hardware configuration or "imaging setup" may refer to different spectra of the illumination light and/or a different selection of bands recorded in the multispectral image.

In the preceding sections, it has been shown how machine learning algorithms can be used to convert pixel-wise reflectance measurements to tissue parameters, such as oxygenation. However, the accuracy of these algorithms can only be guaranteed if the spectra acquired during surgery match the ones seen during training. In machine learning, a regressor or classifier can only give meaningful results for datasets which are similar or related to datasets for which it has been trained. Datasets lacking such relational similarity are also referred to as "out of distribution" (OoD) datasets in the art. In order to address this issue, the inventors developed methods for detecting so-called out of distribution (OoD) spectra to prevent the machine learning algorithms from presenting spurious results for the tissue parameters. This is an important improvement on the path towards reliable functional imaging in medical treatment.

Herein, a multi-stage process for uncertainty handling as illustrated in FIG. 22 is proposed. As shown in FIG. 22, for each pixel or image region of the multispectral image, a spectrum can be defined, which could form the input to the regressor. However, before the regression is carried out, it is checked in an OoD detection whether the spectrum or spectra are "close" to the training data, or whether they are "out of distribution". If it is confirmed that the spectrum is "valid", i.e. close enough to the training data, as is the case for the first line in FIG. 22, the regression can be carried out, to provide one or more functional parameters. In the example shown in FIG. 22, this functional parameter is an oxygenation value. In the preferred embodiment, not only the regression, but also the uncertainty estimation is carried out, based on a full posterior probability distribution schematically likewise shown in FIG. 22. In the first line of FIG. 22, the posterior probability distribution has a single peak and a moderate width, which allows for estimating not only an oxygenation value (77%), but also an uncertainty of ±5%.

The second line of FIG. 22 shows a case where the spectrum deviates significantly from spectra that had been considered during training, such that the OoD detection determines the spectrum to lie "out of domain". In this case, the regression cannot give meaningful results, and is therefore not carried out.

Finally, in the third line of FIG. 22, the spectrum was found to be sufficiently close to the training data, but the posterior probability distribution established in the regression has two peaks, indicating that the result is ambiguous. For situations like this, it is advantageous that a full posterior probability distribution is established rather than just a point estimate for each tissue parameter.

While the inventors are not aware of any previous work in OoD detection in the field of optical imaging, the topic has gained increasing interest in the machine learning community for other purposes. To implement the proposed multistage process for uncertainty handling in multispectral image analysis as schematically shown in FIG. 22, the inventors chose an information theory based approach, building upon the work presented in Choi, H., Jang, E., Alemi, A. A.: *Waic, but why? generative ensembles for robust anomaly detection*. CoRR (2018). In this work, Choi et al. propose the "widely applicable information criterion" (WAIC) as a means to measure the closeness of a new sample to the training distribution. The advantage of this method lies in the fact that it outperforms many other ensemble based unsupervised learning methods while still being fairly easily computable. An unsupervised approach is highly advantageous as it would be an overwhelming task to generate enough labeled negative samples to train a discriminator between in- and outliers. The extra effort associated with applying WAIC is due to the fact that it is an ensemble based method, hence requiring to train a model multiple times. Depending on the data dimensions, this can be rather demanding both in terms of time and hardware requirements. In the present embodiment, invertible neural networks (INN) as described in Ardizzone, L., Kruse, J., Rother, C., Kothe, U.: *Analyzing inverse problems with invertible neural networks*. In: International Conference on Learning Representations (2019) are used to estimate WAIC on multispectral medical imaging data.

The Definition of of WAIC

In the original work of Watanabe, S.: *Algebraic geometry and statistical learning theory*. Cambridge University Press (2009), WAIC was defined as $$\text{WAIC}(x) = \text{Var}_\theta[\log p(x|\theta)] - E_\theta[\log p(x|\theta)];$$

where WAIC(x) quantifies the proximity of a sample x to the distribution of the training data $X^{tr}$, and is distributed according to $p(\theta|X^{tr})$. In the very recent publication of Choi et al. cited above, it was suggested to use WAIC as a means for OoD in the setting of neural networks. Note that the sign convention of the WAIC as used by Choi and by Watanabe are opposite, and in this disclosure, the definition of Watanabe has been adopted. The variance term in the above equation measures 'how certain' the posterior distribution $p(*|\theta)$ is about a sample x, the heuristic being that it should be more certain about samples that are close to what it has seen before. The second term in the above equation, which is an "expectation term", is used for normalization. The rationale behind this expectation term is that if the expectation of log $p(x|\theta)$ is high, then the spread measured by the variance might also be larger without actually measuring internal uncertainty of the model. Hence, it is subtracted to account for this effect.

WAIC Computation with Invertible Neural Networks

The WAIC concept only works for parametrized models. To meet this precondition, the inventors used a deep neural network $f_\theta$ to encode the spectra X in a latent space Z following an analytically tractable distribution, which in this embodiment was chosen to be a multivariate standard Gaussian. Note that this neural network $f_\theta$ is per se unrelated to the machine learning based classifier or regressor that is eventually to be used for determining functional parameters, except that it is trained using the same training data. Namely, the neural network $f_\theta$ is not intended for predicting any biologically medically meaningful parameters, but is instead simply trained to map a distribution of spectra X to a multivariate standard Gaussian distribution, and is only used for this OoD analysis.

Let $f_\theta: X \subset R^n \rightarrow Z \subset R^n$ denote the neural network with parameters $\theta$. Then one can use the change of variable formula to compute the log-likelihood log $p(x|\theta)$ for a spectrum x as $$\log p(x|\theta) = -\frac{1}{2}\|f_\theta(x)\|^2 - n/2 \log(2\pi) + \log|\det Jf_\theta(x)|,$$

where $Jf_\theta$ denotes its Jacobian. The above expression for the log-likelihood log $p(x|\theta)$ shows that it is mandatory for the log-Jacobi determinant of the network $f_\theta$ to be efficiently computable. One established architecture permitting this is the one of normalizing flows originally introduced in Dinh, L., Sohl-Dickstein, J., Bengio, S.: *Density estimation using Real NVP*. CoRR (2016), which was refined in the above-mentioned article of Ardizzone et al. under the name of invertible neural networks (INN). For each of the examples described in the next section, an ensemble of INNs was trained to estimate $p(\theta|X^{tr})$. Each network consisted of 10 layers of so called coupling blocks (see Dinh et al.) each followed by a permutation layer. Each coupling block consisted of a 3 layer fully connected network with ReLU activation functions. The networks were trained using Maximum-Likelihood training, i. e. by maximizing the loss L(x)=log $p(x|\theta)$ as given in the above equation using the Adam optimizer is disclosed in Kingma, D. P., Ba, J.: Adam: *A method for stochastic optimization*. arXiv preprint arXiv:1412.6980 (2014).

EXAMPLES

The approach to OoD detection explained above has been validated by the inventors in various examples both in silico as well as in vivo use cases.

An in silico quantitative validation based on simulations is described first. In the simulation framework used, multispectral imaging pixels are again generated from a vector t of tissue properties, which are assumed to be relevant for the image formation process. Plausible tissue samples t are drawn from a layered tissue model as explained in the dedicated section of the same name above. The simulation framework was used to generate a data set $X_{raw}$, consisting of 550,000 high resolution spectra and corresponding ground truth tissue properties. It was split in a training $X_{raw}^{tr}$ and a test set $X_{raw}^{te}$, comprising 500,000 and 50,000 spectra respectively.

For the in silico quantitative validation, the (high resolution) spectra of the simulated data sets were converted to plausible camera measurements using the filter response functions of the 8-band Pixelteq SpectroCam. Herein, a subscript (in this case: SC for SpectroCam) is used to refer to the data set $X_{raw}$ after it was adapted to a certain camera. $X_{SC}^{tr}$ was split into a small training set $X_{SC}^{tr,s}$ and a superset $X_{SC}^{sup}$, such that the support of $X_{SC}^{tr,s}$ lay within the support of $X_{SC}^{sup}$ and $X_{SC}^{sup}$ consisted of a cluster of data points outside of the support of $X_{SC}^{tr,s}$, as illustrated in FIG. 23. This led to a split of $X_{SC}^{tr,d}$ of approximately 49% of $X_{SC}^{tr}$ and $X_{SC}^{sup}$ of approximately 51% of $X_{SC}^{tr}$. An ensemble of five INNs was trained on $X_{SC}^{tr,s}$ and the WAIC value was evaluated on $X_{SC}^{sup}$. $X_{SC}^{sup,r}$ is defined as the reduced or "restricted" data set of $X_{SC}^{sup}$ lying in the support of $X_{SC}^{tr,s}$.

The inventors then investigated
(1) whether the WAIC distribution of the $X_{SC}^{sup,r}$ matches that of the $X_{SC}^{tr,s}$ and whether
(2) the part of $X_{SC}^{sup}$ not in the support of $X_{SC}^{tr,s}$ was correctly classified as outliers by our method.

As is seen from FIGS. 23 and 24, both of the above assumptions could be confirmed. FIG. 23 shows the results obtained with the WAIC method—trained on the small training set $X_{SC}^{tr,s}$—when applied to the superset $X_{SC}^{sup}$. In FIG. 23, the small training set $X_{SC}^{tr,s}$ is projected onto the first two principal components (PCA) of the complete training set $X_{SC}^{tr}$, and lies within the dashed contour. The 2% percentile of best superset spectra according the WAIC value are shown as a kernel density estimation and lie within the dotted contour shown in FIG. 23, which fully lies within the training set $X_{SC}^{tr,s}$. Accordingly, the 2% percentile spectra showing the best WAIC values are clearly "in-distribution-samples". The 2% percentile worst spectra according to the WAIC-value are likewise shown as a kernel density estimation and lie within the chain dotted contour in FIG. 23, and hence clearly outside the small training set $X_{SC}^{tr,s}$. It is therefore seen that the part of $X_{SC}^{sup}$ not in the support of $X_{SC}^{tr,s}$ was correctly classified as outliers.

FIG. 24 shows the WAIC distribution of the training set $X_{SC}^{tr,s}$, the superset $X_{SC}^{sup}$ and the restricted superset $X_{SC}^{sup,r}$. Note that in FIG. 24 the superset box plot needed to be truncated, since it included much larger WAIC values than the training set and the restricted superset. As seen from FIG. 24, the WAIC distributions of the restricted superset $X_{SC}^{sup,r}$ and of the training set $X_{SC}^{tr,s}$ are in excellent agreement. In fact, the superset $X_{SC}^{sup}$ only differs in the regard that there are far more outliers, which can be accounted to the data points outside of $X_{SC}^{tr,s}$.

Next examples directed to in vivo applications are described. In general, there can be various reasons why one would wish to detect a multispectral image, or a part of a multispectral image in which the spectra do not closely match the training data distribution. Possible applications include the detection of abnormal tissue or of artificial objects within the multispectral image, for example surgical or diagnostic instruments.

To demonstrate the working and usefulness of this aspect, the inventors used the complete training set $X_{SC}^{tr}$ to train an ensemble of five INNs. As in vivo test data, the inventors acquired endoscopic images of porcine organs which were classified as organs lying in the simulation domain $X^{iD}$ and organs not lying in the simulation domain $X^{oD}$. These spectra were acquired using a Pixelteq SpectroCam on a 30 Stortz laparascope with a a Stortz Xenon light source (Storz D-light P 201337 20). More particularly, the inventors classified liver, spleen, abdominal wall, diaphragm and bowl as in-domain-organs, as hemoglobin can be assumed to be the main absorber in these. In contrast, the inventors classified gallbladder as an out-of-domain organ, since bile is a notable absorber, but has not been considered in the simulation framework using the layered tissue model described above. The sets $X^{iD}$ and $X^{oD}$ consisted of 50000 spectra and 10000 spectra, respectively. The hypothesis underlying this embodiment was that the WAIC values of $X^{iD}$ should be much lower than those for $X^{oD}$. For reference, the resulting WAIC distributions were also compared to that of the simulated test data $X_{SC}^{te}$.

The WAIC distribution for the simulated test data $X_{SC}^{te}$, the in-domain-organs $X^{iD}$ and the out-of-domain organ $X^{oD}$ are shown in FIG. 25. The distribution of the test data is by far the sharpest with a maximum a posterior probability (MAP) at −4.9. The distribution closely matches that of the training data (MAP=−4.9). The distribution of $X^{iD}$ also possesses a sharp maximum, however with a far heavier tail. The MAP estimate yields 9.3 which indicates a still existent domain gap between the simulation domain and the organ domain. The distribution of $X^{oD}$ is very noisy and has a much heavier tail than $X^{iD}$. The MAP lies at 34. This indicates that the proposed WAIC estimate is suitable to distinguish between in-domain-tissue and out-of-domain tissue based on in vivo images. This is a remarkable result, since it is entirely based on unsupervised learning, and still allows to automatically delete determine whether a certain organ belongs to a trained or untrained domain.

In a further embodiment, the OoD detection can be used for detecting scene changes. As was explained herein, intraoperative image modalities often rely on a careful calibration of the device. For example, when recovering blood oxygenation from multispectral measurements, it is generally required that the regressor employed is trained with the light source that is used during the intervention. In the previously described embodiments, it was indicated how this situation can be handled, for example by estimating a spectral composition of light illuminating a region of interest of the tissue, which need not exactly match the spectral composition on which a given classifier or regressor was trained, and by making the regressor or classifier employed for deriving tissue parameters to match the estimated spectral composition of the illumination light according to one of the possibilities described herein.

One remaining difficulty in this regard is that particularly in open surgery, the illumination conditions may frequently change, for example when an additional surgical light is switched on, or is brought closer to the region of interest. While it has been demonstrated above how one can cope with varying illumination conditions, there remains the task of noticing significant changes in the illumination conditions that would require an adaption of the regressor or classifier.

Of course, as was explained above, the described estimation of the spectral composition of the light illuminating a region of interest can be repeated at predetermined time intervals, such that a change in illumination can be noticed when it arises. Unfortunately, this may amount to extra effort occupying computational resources and cause idle times during the determination of tissue parameters. However, based on the OoD detection described herein, a change in the illumination spectrum can be automatically detected once it occurs, if the illumination changes from an illumination that was considered in the training to an untrained illumination. This is of practical relevance, since unnoticed illumination changes can be harmful, since they may render the tissue parameter estimation results invalid. Note that an "illumination considered in the training" and an "untrained illumination" are of course not absolute criteria, but will depend on the respective application. For example, consider the simple case that there are two regressors, a first regressor that has been trained with first training data associated with a first illumination source and a second regressor that has been trained with second training data associated with a second illumination source, having a different spectral composition as the first illumination source. Then, when using the first regressor, the OoD detection will be based on the WAIC determined based on an ensemble of INNs that has been trained with this first training data. Then, when the illumination is changed to the second illumination, this will be detected as OoD, because this ensemble of INNs has not been trained by training data associated with this second illumination, and the encountered spectra are therefore therefore untrained "from its perspective", although this data has of course been used in training for another ensemble of INNs, that is to be used for detecting OoD with regard to the second regressor.

In a specific embodiment, $X_{raw}$ was adapted to to a xiQ XIMEA (Muenster, Germany) SN m4 4 mosaic camera consisting of 16 bands assuming a Wolf LED light source (Wolf Endolight LED 2.2). An ensemble of five INNs was trained on $X_{Xim}^{tr}$. Furthermore, 200 512×272-pixel images of the lip of a healthy human volunteer were recorded using the xiQ XIMEA camera and a 30 Stortz laparascope, as shown in FIG. 26 on the right. At around image 80, the endoscope was switched from a Stortz Xenon light source (Storz D-light P 201337 20) to a Wolf LED light source (Wolf Endolight LED 2.2). On the left of FIG. 26, a corresponding WAIC time series for the region of interest is shown. It is seen that the changing light source leads to a drastic change in the WAIC. The uncertainty prior to the change of lighting can most likely be explained by the short darkness stemming from the light source switch. The jump at image 100 was due to involuntary movement of the volunteer leading to the image being out of focus. One reason for the generally high WAIC values is the fact that melanin (a chromophore in the skin) was not simulated in the training data.

From FIG. 26, it is demonstrated that by observing the WAIC, a change in illumination can be automatically determined, and this could for example trigger a recalibration of the system to the different spectral composition of the new illumination. Clearly, this OoD detection can be employed to automatically detect various other scene changes as well.

In the present implementation, five INNs were used in the ensembles. According to the current understanding of the inventors, this number is sufficient. the inventors computed the WAIC on the data sets used for the organ detection example for up to 20 ensemble members. For both the simulated test data and the in domain organs the values stabilized below n=10.

The above examples underline the power of WAIC in the setting of medical OoD detection. For practical implementations, it has to be considered that the WAIC is based on "arbitrary units", and that it is therefore not easily possible to define a universal threshold for outlier detection, which would have to be typically determined for each individual application. One approach to deal with this is to devise a suitable normalization. Another possibility could be to just mask the worst n pixels in a certain ROI. Since the estimation of WAIC requires an ensemble of neural networks, the computational effort becomes expensive for larger input dimensions. In view of this, it is suggested to adapt methods for network compression to reduce the computational effort.

Although a preferred exemplary embodiment is shown and specified in detail in the drawings and the preceding specification, these should be viewed as purely exemplary and not as limiting the invention. It is noted in this regard that only the preferred exemplary embodiment is shown and specified, and all variations and modifications should be protected that presently or in the future lie within the scope of protection of the invention as defined in the claims.

The invention claimed is:
1. A method of generating and displaying one or more augmented images of tissue of a patient undergoing open treatment, said method comprising:
estimating a spectral composition of light illuminating a region of interest of the tissue by measurement or by computing said spectral composition based on control parameters controlling said light illuminating the region of interest,
obtaining one or more multispectral images of the region of interest using a multispectral camera,
applying said one or more multispectral images or one or more images derived from said one or more multispectral images to a machine learning based regressor or classifier to thereby derive one or more tissue parameters associated with image regions or pixels of the one or more multispectral images, wherein said machine learning based regressor or classifier has been trained to predict the one or more tissue parameters from the one or more multispectral images under a given spectral composition of illumination, and
generating one or more augmented images and displaying said one or more augmented images on a display device, wherein said one or more augmented images correspond to the one or more multispectral images and include the one or more tissue parameters,
wherein the machine learning based regressor or classifier is made to match the estimated spectral composition of light illuminating said region of interest of the tissue by one of
selecting the machine learning based regressor or classifier from among a plurality of candidate machine learning based regressors or classifiers that have each been previously trained for a different spectral composition of illumination, such that the given spectral composition of illumination for the machine learning based regressor or classifier is the most similar to the estimated spectral composition of said light illuminating said region of interest, or
transforming the obtained one or more multispectral images based on information derived from the estimated spectral composition of the light illuminating said region of interest and applying the transformed one or more multispectral images to a standard machine learning based regressor or classifier, which has been trained under a standard illumination, wherein the transformation is for compensating for a change in the one or more multispectral images due to a deviation in the spectral composition of the illumination from the standard illumination, or
retraining an already trained machine learning based regressor or classifier using simulation data that is adapted to the estimated spectral composition of light illuminating said region of interest.

2. The method of claim 1, wherein said at least one tissue parameter comprises one or more of: an oxygenation, a blood volume fraction, a presence or concentration of lipids, a presence or concentration of melanine, a presence or concentration of bile, a presence or density of collagen or elastin, a presence or concentration of water, a presence of artificial dyes, or a parameter derived from any or any combination thereof,
a tissue classification parameter designating various organs, designating necrotic tissue, designating cancerous tissue, or designating polyps,
a parameter designating different materials and/or tooth decay in dental applications,
a landmark-indicating-parameter designating nerves or important vessels as key landmarks;
an event parameter indicating the presence of bleeding, tissue inflammation, or the presence of smoke,
a neurological parameter representing sensory evoked potentials, or a prediction-of event-parameter, predicting a medical event.

3. The method of claim 1, wherein said estimating a spectral composition of light illuminating a region of interest of the tissue is based on light that is specularly reflected from said region of interest of the tissue, or from a region close to said region of interest of the tissue.

4. The method of claim 3, wherein said method further comprises identifying regions of specular reflection within the one or more multispectral images of said region of interest of the tissue, or a region close to said region of interest of the tissue.

5. The method of claim 3, wherein said method further comprises transforming said one or more multispectral images to a lower dimensional color space.

6. The method of claim 4, further comprising sorting regions of specular reflection according to size, wherein a second to n-th largest connected regions of specular pixels are determined, where n is an integer number that is smaller than the total number of regions of connected specular pixels.

7. The method of claim 4, further comprising subjecting identified regions of specular reflection to morphologic dilation to thereby ensure that the identified regions of specular reflection include a predetermined number or percentage of non-saturated pixels.

8. The method of claim 4, further comprising separating, within an identified region of specular reflection within the one or more multispectral images, contributions from specular reflection from contributions from diffused reflection, using a principal component analysis or an independent component analysis.

9. The method of claim 3, wherein for estimating said spectral composition of the illuminating light, multispectral images of said region of interest are recorded with a lower exposure than the one or more multispectral images applied to which said machine learning based regressor or classifier.

10. The method of claim 9, wherein said multispectral images recorded with the lower exposure are recorded with one or both of a lower exposure time and a smaller aperture opening than the one or more multispectral images applied to said machine learning based regressor or classifier, wherein the exposure time or aperture size is chosen such that the intensity for the multispectral images recorded with the lower exposure is decreased by at least 20% with respect to the intensity obtained for the exposure used for recording the one or more multispectral images applied to said machine learning based regressor or classifier.

11. The method of claim 9, wherein said spectral composition is estimated based on a selected number of pixels or pixel groups, wherein said pixels or pixel groups are selected from said multispectral images recorded with the lower exposure according to a selection criterion ensuring that the pixel or pixel group has a high lightness, under the provision that an image detector used for recording said multispectral images recorded with the lower exposure is not saturated for any of the spectral components of the pixel or pixel group, wherein the lightness is a measure for the average intensity of the pixel or pixel group over all of its spectral components.

12. The method of claim 3, wherein said one or more multispectral images comprises a number of k color channels, and wherein the method further comprises transforming spectral information from said k color channels, or a subset thereof, to a quasi-continuous spectrum, wherein wavelengths within said quasi-continuous spectrum are separated by no more than 10 nm.

13. A system for generating and displaying one or more augmented images of tissue of a patient undergoing open treatment said system comprising:
an apparatus configured to estimate a spectral composition of light illuminating a region of interest of the tissue by measuring or computing said spectral composition based on control parameters controlling said light illuminating the region of interest,
a multispectral camera for obtaining one or more multispectral images of the region of interest,
a computing device comprising a machine learning module for applying the one or more multispectral images or one or more images derived from said one or more multispectral images to a machine learning based regressor or classifier, to thereby derive one or more tissue parameters associated with image regions or pixels of the one or more multispectral images, wherein said machine learning based regressor or classifier has been trained to predict the one or more tissue parameters from the one or more multispectral images under a given spectral composition of illumination,
a display device,
wherein the computing device is configured to generate one or more augmented images and display said one or more augmented images on the display device, wherein said one or more augmented images correspond to the one or more multispectral images and include the one or more tissue parameters,
wherein the computing device is configured to make the machine learning based regressor or classifier match the estimated spectral composition of light illuminating said region of interest of the tissue by one of
selecting the machine learning based regressor or classifier from among a plurality of candidate machine learning based regressors or classifiers that each have been previously trained for a different spectral composition of illumination, such that the given spectral composition of illumination machine learning based regressor or classifier is the most similar to the estimated spectral composition of said light illuminating said region of interest, or
transforming the obtained one or more multispectral images based on information derived from the estimated spectral composition of the light illuminating said region of interest and applying the transformed one or more multispectral images to a standard machine learning based regressor or classifier, which has been trained under a standard illumination, wherein the transformation is for compensating for a change in the one or more multispectral images due to a deviation in the spectral composition of the illumination from the standard illumination, or
retraining an already trained machine learning based regressor or classifier using simulation data that is adapted to the estimated spectral composition of light illuminating said region of interest.

14. The system of claim 13, further comprising goggles, wherein said system is configured to project said one or more augmented images into field of view of said goggles.

15. The system of claim 14, wherein said goggles further comprise one or more of the following components:
the multispectral camera,
a microphone for receiving speech commands,
a wireless data link for exchanging data with computing device or a database, and
a data processing unit suitable for one or more of applying said one or more multispectral images to said machine learning based regressor or classifier, recognizing gestures indicating regions of interest for which the one or more augmented images are to be created, and controlling the display of the one or more augmented images in the field of view of the glasses.

16. The system of claim 13, wherein said one or more tissue parameters comprises one or more of the following: an oxygenation, a blood volume fraction, a presence or concentration of lipids, a presence or concentration of melanine, or a parameter derived from any or any combination thereof,
- a tissue classification parameter designating various organs, designating necrotic tissue, designating cancerous tissue, or designating polyps,
- a parameter designating different materials or tooth decay in dental applications,
- a landmark indicating parameter designating nerves or important vessels as key landmarks;
- an event parameter indicating the presence of bleeding, or a parameter indicating the presence of smoke,
- a neurological parameter representing sensory evoked potentials, or
- a prediction of event parameter, predicting a medical event.

17. The system of claim 13, wherein said apparatus for estimating the spectral composition of the light illuminating region of interest is configured to estimate for carrying out said estimation based on light that is specularly reflected from said region of interest of the tissue, or from a region close to said region of interest of the tissue.

18. The system of claim 17, wherein said apparatus is configured to estimate the spectral composition of the light illuminating the region of interest by identifying regions of specular reflection within the one or more multispectral images of said region of interest of the tissue, obtained with said multispectral camera, or a region close to said region of interest of the tissue.

19. The system of claim 17, wherein said apparatus configured to estimate the for estimating spectral composition of the light illuminating the region of interest is further configured to transform said one or more multispectral images to a lower dimensional color space.

20. The system of claim 18, wherein said apparatus is further configured for subjecting identified regions of specular reflection to morphologic dilation to thereby ensure that the identified regions of specular reflection include a predetermined number or percentage of non-saturated pixels.

21. The system of claim 18, wherein said apparatus is further configured for separating, within an identified region of specular reflection within the one or more multispectral images, contributions from specular reflection from contributions from diffused reflection, using a principal component analysis or an independent component analysis.

22. The system of claim 17, wherein for estimating said spectral composition of the light illuminating the region of interest, the system is configured for recording multispectral images of said region of interest with a lower exposure than the one or more multispectral images applied to said machine learning based regressor or classifier is applied.

23. The system of claim 22, wherein said system is configured for recording said multispectral images recorded with the lower exposure with one or both of a lower exposure time and a smaller aperture opening than the one or more multispectral images applied to said machine learning based regressor or classifier, wherein the exposure time or aperture size is set such that the intensity for the multispectral images recorded with the lower exposure is decreased by at least 20% with respect to the intensity obtained for the exposure used for recording the one or more multispectral images applied to said machine learning based regressor or classifier is applied.

24. The system of claim 22, wherein said system is configured for estimating said spectral composition of the light illuminating the region of interest based on a selected number of pixels or pixel groups, wherein said system is configured for selecting said pixels or pixel groups from said multispectral images recorded with the lower exposure according to a selection criterion ensuring that the pixel or pixel group has a high lightness, under the provision that an image detector used for recording said image multispectral images recorded with the lower exposure is not saturated for any of the spectral components of the pixel or pixel group, wherein the lightness is a measure for the average intensity of the pixel or pixel group over all of its spectral components.

* * * * *

UNITED STATES PATENT AND TRADEMARK OFFICE
CERTIFICATE OF CORRECTION

| | | |
|---|---|---|
| PATENT NO. | : 12,329,491 B2 | Page 1 of 1 |
| APPLICATION NO. | : 17/263850 | |
| DATED | : June 17, 2025 | |
| INVENTOR(S) | : Lena Maier-Hein et al. | |

It is certified that error appears in the above-identified patent and that said Letters Patent is hereby corrected as shown below:

In the Claims

At Column 56, Line 63, "landmarks;" should be -- landmarks, --.

At Column 59, Line 18, "landmarks;" should be -- landmarks, --.

At Column 59, Line 25, "for estimating" should be -- configured to estimate --.

At Column 59, Line 31, "is configured" should be -- configured --.

At Column 59, Line 39, "to estimate the for estimating" should be -- to estimate the --.

Signed and Sealed this
Eighteenth Day of November, 2025

John A. Squires
*Director of the United States Patent and Trademark Office*